(12) United States Patent  
Hattori et al.

(10) Patent No.: US 7,629,366 B2
(45) Date of Patent: Dec. 8, 2009

(54) AMINOALCOHOL DERIVATIVES

(75) Inventors: Kouji Hattori, Osaka (JP); Yasuyo Tomishima, Osaka (JP); Masashi Imanishi, Osaka (JP)

(73) Assignee: Fujisawa Pharmaceutical Co., Ltd., Osaka-shi (JP)

( * ) Notice: Subject to any disclaimer, the term of this patent is extended or adjusted under 35 U.S.C. 154(b) by 570 days.

(21) Appl. No.: 11/304,632

(22) Filed: Dec. 16, 2005

(65) Prior Publication Data

US 2006/0100252 A1 May 11, 2006

Related U.S. Application Data

(62) Division of application No. 10/603,943, filed on Jun. 26, 2003, now Pat. No. 7,037,938.

(30) Foreign Application Priority Data

Jun. 27, 2002 (AU) .................... PS3241
Dec. 30, 2002 (AU) .................... 2002953604

(51) Int. Cl.
*A61K 31/44* (2006.01)
*C07D 211/82* (2006.01)
(52) U.S. Cl. .......... 514/357; 514/567; 546/334
(58) Field of Classification Search ........ 514/357, 514/567; 546/334
See application file for complete search history.

(56) References Cited

U.S. PATENT DOCUMENTS

| 5,232,946 A | 8/1993 | Hurnaus et al. ........... 514/546 |
| 7,417,060 B2 * | 8/2008 | Hattori et al. ........... 514/357 |
| 2004/0106653 A1 | 6/2004 | Sakurai et al. |
| 2005/0137236 A1 | 6/2005 | Hattori et al. |

FOREIGN PATENT DOCUMENTS

| GB | 2 305 665 | 4/1997 |
| WO | WO 90/06299 | 6/1990 |
| WO | WO 02/32897 | 4/2002 |
| WO | WO 03/042164 | 5/2003 |

OTHER PUBLICATIONS

Hurnaus et al. "Preparation of new phenylethanolamines . . . " CA 111:77643 (1989).*
Hattori et al. "Preparation of . . . " CA 140:93927 (2004).*
Hattori et al. "Preparation of biphenyl . . . " CA 143:78089 (2005).*
Hurnaus et al. "Preparation of new phenylethanolamines . . . " CA 111:77643 (1989).
Shuker et al. "The application of high throughput . . . " CA 127:277798 (1997).
Greene "Protective groups in organic synthesis" p. 154, 187-188 (1982).
Fisher et al. "Substituted phenylsulfonamides . . . " CA 124:116877 (1995).
Brazzel et al. "Treatment of glaucoma . . . " CA 126:1213 (1996).
Taniguchi et al. "Preparation of diaryalkylaminoalkanols . . . " CA 132:194184 (2000).
U.S. Appl. No. 11/547,847, filed Oct. 6, 2006, Hattori, et al.
* cited by examiner

*Primary Examiner*—Celia Chang
(74) *Attorney, Agent, or Firm*—Oblon, Spivak, McClelland, Maier & Neustadt, L.L.P.

(57) ABSTRACT

The present invention relates to a compound formula [I]:

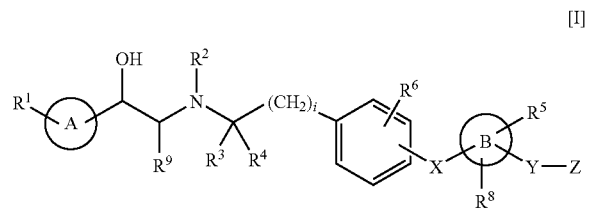

wherein

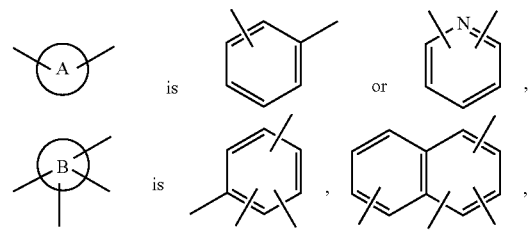

ect.,
X is bond, —$CH_2$—,

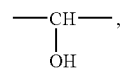

etc.,
Y is bond, —O—$(CH_2)_n$— (in which n is 1, 2, 3 or 4), etc.,
Z is cyano, tetrazolyl, etc.,
$R^1$ is hydrogen, lower alkyl, etc.,
$R^2$ is hydrogen or an amino protective group,
$R^3$ is hydrogen or lower alkyl,
$R^4$ is hydrogen or lower alkyl,
$R^5$ and $R^8$ are each independently hydrogen, halogen, hydroxy, lower alkyl, etc.,
$R^6$ is hydrogen, lower alkyl, etc.,
$R^9$ is hydrogen or lower alkyl, and
i is 1 or 2,
or a salt thereof. The compound [I] of the present invention and pharmaceutically acceptable salts thereof are useful for the prophylactic and/or the therapeutic treatment of pollakiurea or urinary incontinence.

12 Claims, No Drawings

AMINOALCOHOL DERIVATIVES

CROSS-REFERENCE TO RELATED APPLICATIONS

The present application is a divisional of U.S. Ser. No. 10/603,943, filed on Jun. 26, 2003 (now U.S. Pat. No. 7,037,938), and claims priority to AU PS3241, filed on Jun. 27, 2002, and AU 2002953604, filed on Dec. 30, 2002.

FIELD OF THE INVENTION

This invention relates to new aminoalcohol derivatives and salts thereof which are beta-3 ($\beta_3$) adrenergic receptor agonists and useful as a medicament.

BACKGROUND OF THE INVENTION

International Publications No. WO 90/06299, published Jun. 14, 1990, describes derivatives of phenylethanolamines as having an effect on the metabolism, preferably reduction of the blood sugar level and body fat, and International Publication No. WO 02/32897, published Apr. 25, 2002, describes derivatives of alpha-aryl ethanolamines useful as β3 adrenergic receptor agonists.

DISCLOSURE OF THE INVENTION

This invention relates to new aminoalcohol derivatives which are $\beta_3$ adrenergic receptor agonists and salts thereof.

More particularly, it relates to new aminoalcohol derivatives and salts thereof which have gut sympathomimetic, anti-ulcerous, anti-pancreatitis, lipolytic, anti-urinary incontinence, anti-pollakiuria activities, anti-diabetes and anti-obesity, to processes for the preparation thereof, to a pharmaceutical composition comprising the same and to a method of using the same therapeutically in the treatment and/or prevention of gastro-intestinal disorders caused by smooth muscle contractions in a human being or an animal.

One object of this invention is to provide new and useful aminoalcohol derivatives and salts thereof which have gut sympathomimetic, anti-ulcerous, lipolytic, anti-urinary incontinence, anti-pollakiuria activities, anti-diabetes and anti-obesity.

Another object of this invention is to provide processes for the preparation of said aminoalcohol derivatives and salts thereof.

A further object of this invention is to provide a pharmaceutical composition comprising, as an active ingredient, said aminoacohol derivatives and salts thereof.

Still further object of this invention is to provide a therapeutical method for the treatment and/or prevention of aforesaid diseases in a human being or an animal, using said aminoalcohol derivatives and salts thereof.

The object aminoalcohol derivatives of this invention are new and can be represented by compound of the following formula [I]:

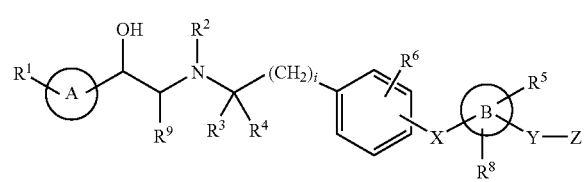

[I]

wherein

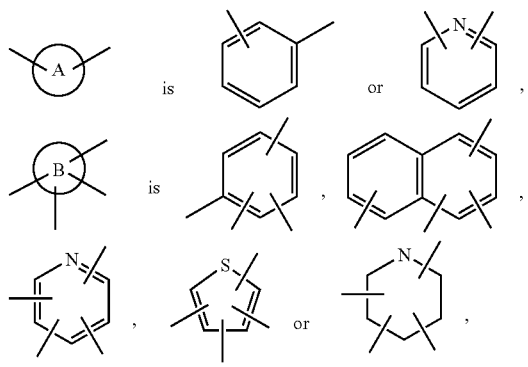

X is bond, —CH$_2$—,

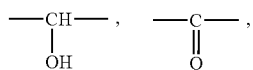

—O—, —OCH$_2$—, —CH$_2$O—, —S— or

(in which R$^7$ is hydrogen or lower alkyl),
Y is bond, —O—(CH$_2$)$_n$— (in which n is 1, 2, 3 or 4), —(CH$_2$)$_m$— (in which m is 1, 2, 3 or 4),

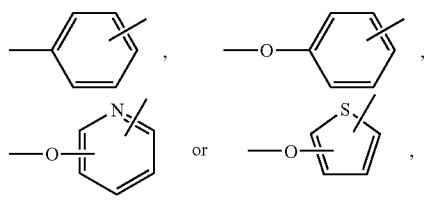

Z is cyano, tetrazolyl, (benzylsulfonyl)carbamoyl, benzoylsulfamoyl, formyl, carboxy or protected carboxy,
R$^1$ is hydrogen, lower alkyl or halogen,
R$^2$ is hydrogen or an amino protective group,
R$^3$ is hydrogen or lower alkyl,
R$^4$ is hydrogen or lower alkyl,
R$^5$ and R$^8$ are each independently hydrogen, halogen, hydroxy, lower alkyl, lower alkenyl, lower alkoxy, hydroxy(lower)alkoxy, mono(or di or tri)halo(lower)alkoxy, lower alkoxy(lower)alkoxy, lower alkenyloxy, cyclo(lower)alkyloxy, cyclo(lower)alkyl(lower)alkoxy, benzyloxy, phenoxy, lower alkylthio, cyclo(lower)alkylthio, lower alkylsulfonyl, cyclo(lower)alkylsulfonyl, amino, mono(or di)(lower)alkylamino, mono(or di or tri)halo(lower)alkyl, cyano, piperidinyl or phenyl,
R$^6$ is hydrogen, lower alkyl or halogen,
R$^9$ is hydrogen or lower alkyl, and
i is 1 or 2, provided that
(1) when X is bond, —CH₂—,
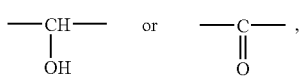
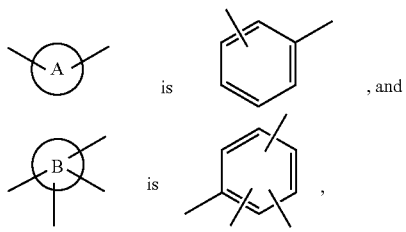
then R⁵ is not hydrogen, or
(2) when i is 1,
then
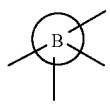
is not
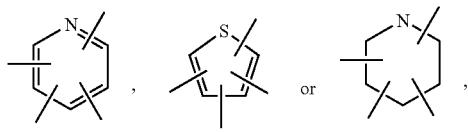
or a salt thereof.
According to this invention, the object compounds can be prepared by processes which are illustrated in the following schemes.
Process 1
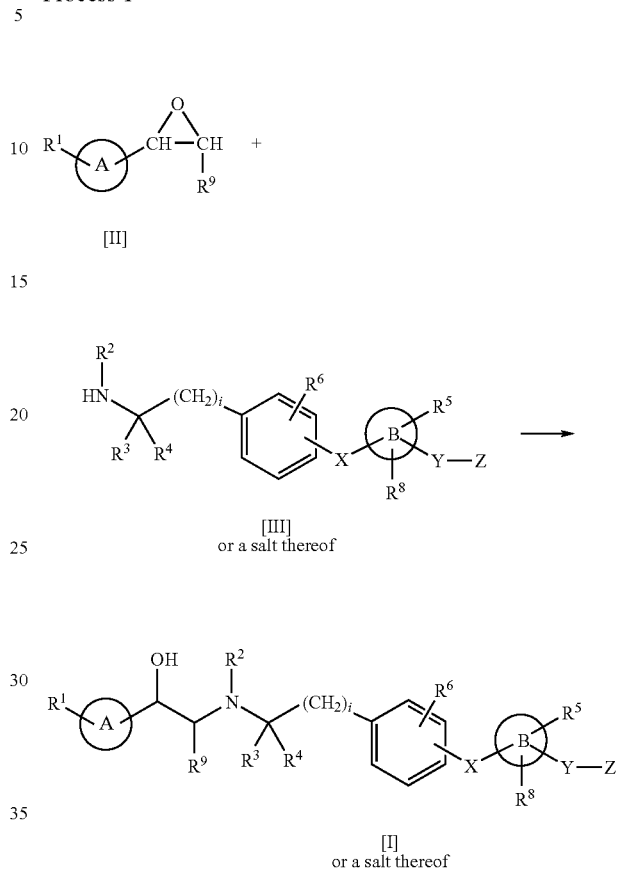
Process 2
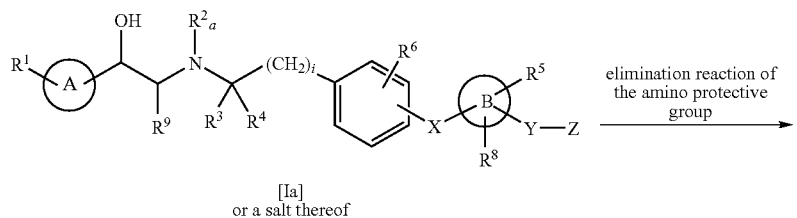
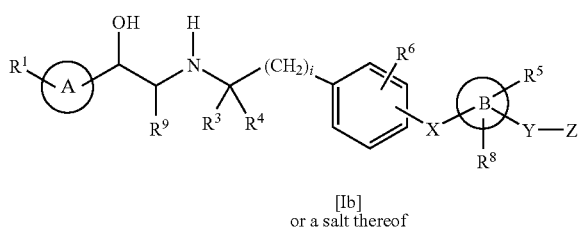

Process 3
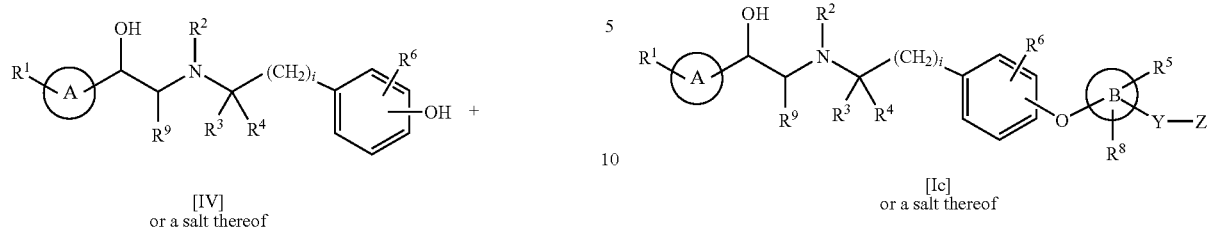
Process 4
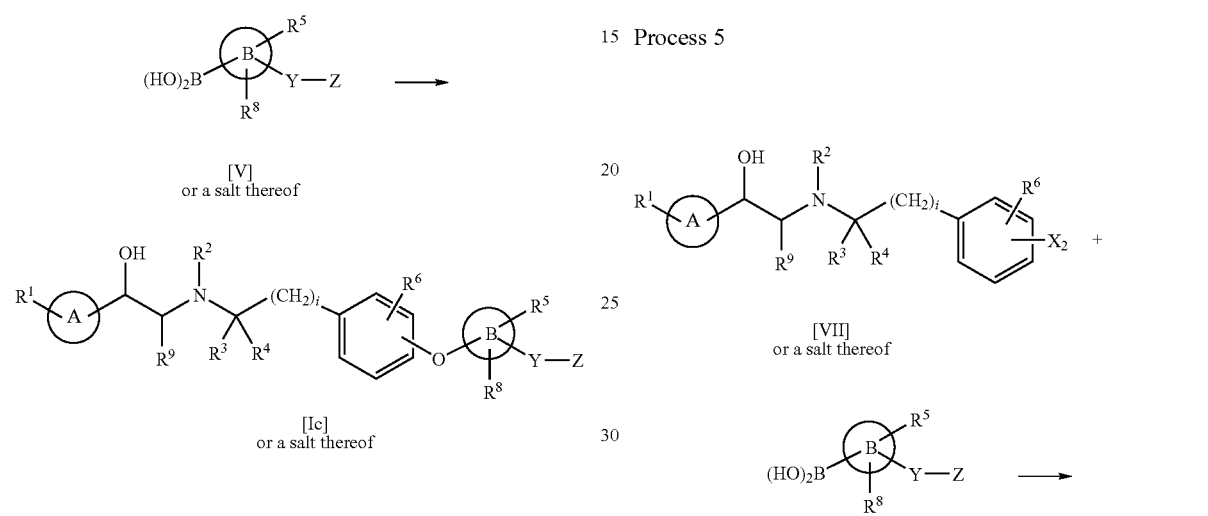
Process 5
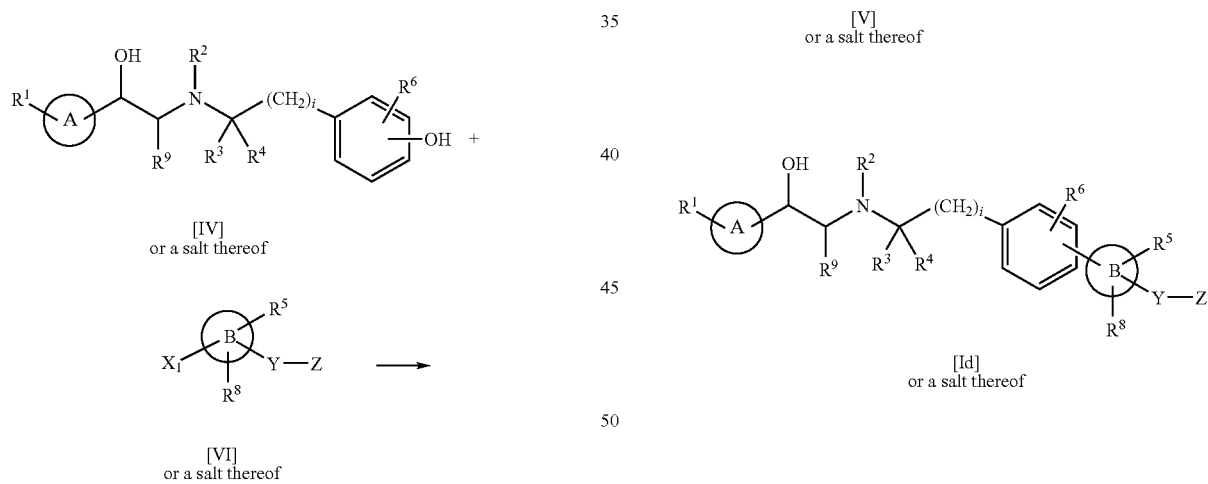
Process 6
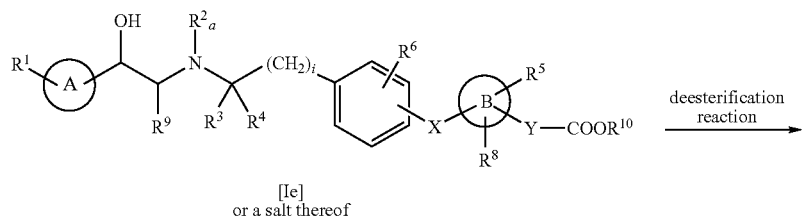

-continued

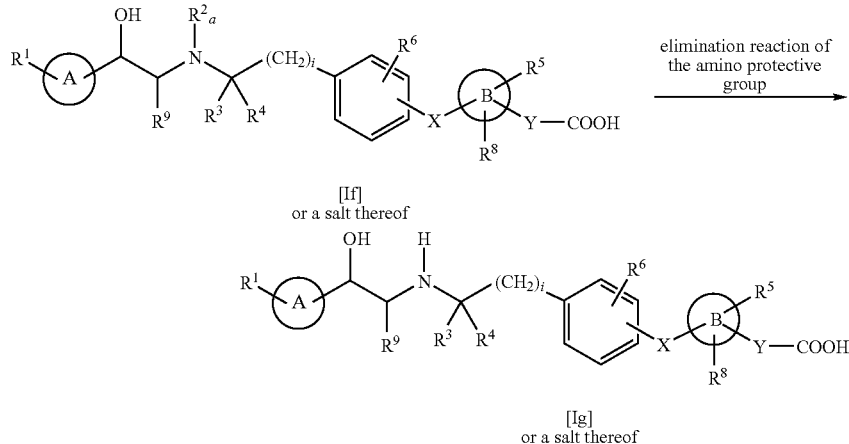

[If]
or a salt thereof

↓ elimination reaction of the amino protective group

[Ig]
or a salt thereof wherein

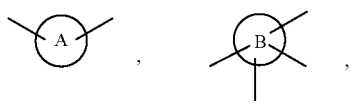

X, Y, Z, $R^1$, $R^2$, $R^3$, $R^4$, $R^5$, $R^6$, $R^8$, $R^9$ and i are each as defined above,
$R_a^2$ is an amino protective group,
$R^{10}$ is lower alkyl, and
$X_1$ and $X_2$ are each a leaving group.

As to the starting compounds [II], [III], [Ia], [IV], [V], [VI] and [VII], some of them are novel and can be prepared by the procedures described in the Preparations and Examples mentioned below or a conventional manner.

In the above and subsequent description of the present specification, suitable examples of the various definition to be included within the scope of the invention are explained in detail in the following.

The term "lower" is intended to mean a group having 1 to 6, preferably 1 to 4, carbon atom(s), unless otherwise indicated.

Suitable "lower alkyl" and "lower alkyl" moiety in the terms of "mono(or di)(lower)alkylamino" and "mono(or di or tri)halo(lower)alkyl" may include straight or branched one having 1 to 6 carbon atom(s), such as methyl, ethyl, propyl, isopropyl, butyl, isobutyl, sec-butyl, tert-butyl, pentyl, 1-methylpentyl, tert-pentyl, neo-pentyl, hexyl, isohexyl and the like.

Suitable "lower alkoxy" may include methoxy, ethoxy, propoxy, isopropoxy, butoxy, iso-butoxy, tert-butoxy, pentyloxy, tert-pentyloxy, hexyloxy and the like, in which preferable one is methoxy or ethoxy.

Suitable "cyclo(lower)alkyl" moiety in the term of "cyclo(lower)alkyloxy" may include cyclopropyl, cyclobutyl, cyclopentyl, cyclohexyl and the like, in which preferable one is cyclohexyl.

Suitable "halogen" may be fluoro, chloro, bromo and iodo, in which preferable one is chloro.

Suitable "mono(or di or tri)halo(lower)alkyl" may include chloromethyl, dichloromethyl, trichloromethyl, bromomethyl, dibromomethyl, tribromomethyl, fluoromethyl, difluoromethyl, trifluoromethyl, 1 or 2-chloroethyl, 1 or 2-bromoethyl, 1 or 2-fluoroethyl, 1,1-difluoroethyl, 2,2-difluoroethyl and the like.

Suitable "protected carboxy" may include esterified carboxy such as lower alkoxycarbonyl [e.g. methoxycarbonyl, ethoxycarbonyl, propoxycarbonyl, butoxycarbonyl, tert-butoxycarbonyl, pentyloxycarbonyl, hexyloxycarbonyl, etc.], halo(lower)alkoxycarbonyl [e.g. (chloromethoxy)carbonyl, (2,2,2-trichloroethoxy)carbonyl, (2,2,2-trifluoroethoxy)-carbonyl, (2-chloropropoxy)carbonyl, (1-fluoro-4-bromobutoxy)carbonyl, (4-chloropentyloxy)carbonyl, (6-chlorohexyloxy)carbonyl, etc.], higher alkoxycarbonyl [e.g. heptyloxycarbonyl, octyloxycarbonyl, 2-ethylhexyloxycarbonyl, nonyloxycarbonyl, decyloxycarbonyl, 3,7-dimethyloctyloxycarbonyl, undecyloxycarbonyl, dodecyloxycarbonyl, tridecyloxycarbonyl, tetradecyloxycarbonyl, pentadecyloxycarbonyl, 3-methyl-10-ethyldodecyloxycarbonyl, hexadecyloxycarbonyl, heptadecyloxycarbonyl, octadecyloxycarbonyl, nonadecyloxycarbonyl, icosyloxycarbonyl, etc.], aryloxycarbonyl [e.g. phenoxycarbonyl, naphthyloxycarbonyl, etc.], aryl(lower)alkoxycarbonyl which may have one or more (preferably 1 to 3) suitable substituent(s) such as phenyl (lower)alkoxycarbonyl which may have nitro or lower alkoxy [e.g. benzyloxycarbonyl, phenethyloxycarbonyl, p-nitrobenzyloxycarbonyl, p-methoxybenzyloxycarbonyl, etc.], and the like, in which preferable one is lower alkoxycarbonyl and more preferable one is methoxycarbonyl, ethoxycarbonyl or tert-butoxycarbonyl.

Suitable "leaving group" may include hydroxy, reactive group derived from hydroxy and the like.

Suitable "reactive group derived from hydroxy" may include acid residue and the like.

Suitable "acid residue" may include halogen (e.g. fluoro, chloro, bromo, iodo), acyloxy (e.g. acetoxy, tosyloxy, mesyloxy, trifluoromethanesulfonyloxy, etc.) and the like.

Suitable example of "amino protective group" moiety may be common amino protective group such as substituted or unsubstituted lower alkanoyl [e.g. formyl, acetyl, propionyl, trifluoroacetyl, etc.], phthaloyl, lower alkoxycarbonyl [e.g. tert-butoxycarbonyl, tert-amyloxycarbonyl, etc.], substituted or unsubstituted aralkyloxycarbonyl [e.g. benzyloxycarbonyl, p-nitrobenzyloxycarbonyl, etc.], substituted or unsubstituted arenesulfonyl [e.g. benzenesulfonyl, tosyl, etc.], nitrophenylsulfenyl, ar(lower)alkyl [e.g. trityl, benzyl, etc.], and the like, in which preferable one is tert-butoxycarbonyl.

Suitable salts of the object aminoalcohol derivative [I] are pharmaceutically acceptable salts and include conventional non-toxic salts such as an inorganic acid addition salt [e.g. hydrochloride, hydrobromide, sulfate, phosphate, etc.], an organic acid addition salt [e.g. formate, acetate, trifluoroacetate, oxalate, maleate, fumarate, tartrate, citrate, methanesulfonate, benzenesulfonate, toluenesulfonate, etc., an alkali metal salt [e.g. sodium salt, potassium salt, etc.] or the like.

The Processes 1 to 6 for preparing the object compounds of the present invention are explained in detail in the following.

Process 1

The object compound [I] or a salt thereof can be prepared by reacting a compound [II] with a compound [III] or a salt thereof.

Suitable salt of the compound [III] may be the same as those exemplified for the compound [I].

The reaction is preferably carried out in the presence of a base such as an alkali metal carbonate [e.g. sodium carbonate, potassium carbonate, etc.], an alkaline earth metal carbonate [e.g. magnesium carbonate, calcium carbonate, etc.], an alkali metal bicarbonate [e.g. sodium bicarbonate, potassium bicarbonate, etc.], tri(lower)alkylamine [e.g. trimethylamine, triethylamine, etc.], picoline or the like.

The reaction is usually carried out in a conventional solvent, such as an alcohol [e.g. methanol, ethanol, propanol, isopropanol, etc.], diethyl ether, tetrahydrofuran, dioxane, or any other organic solvent which does not adversely influence the reaction.

The reaction temperature is not critical, and the reaction can be carried out under cooling to heating.

Process 2

The object compound [Ib] or a salt thereof can be prepared by subjecting a compound [Ia] or a salt thereof to elimination reaction of the amino protective group.

Suitable salts of the compounds [Ia] and [Ib] may be the same as those exemplified for the compound [I].

This reaction can be carried out in a similar manner to that of Example 11 mentioned below.

Process 3

The object compound [Ic] or a salt thereof can be prepared by reacting a compound [IV] or a salt thereof with a compound [V] or a salt thereof.

Suitable salts of the compounds [Ic], [IV] and [V] may be the same as those exemplified for the compound [I].

This reaction can be carried out in a similar manner to that of Example 15 mentioned below.

Process 4

The object compound [Ic] or a salt thereof can be prepared by reacting a compound [IV] or a salt thereof with a compound [VI] or a salt thereof.

Suitable salts of the compound [Ic], [IV] and [VI] may be the same as those exemplified for the compound [I].

This reaction can be carried out in a similar manner to that of Example 9 mentioned below.

Process 5

The object compound [Id] or a salt thereof can be prepared by reacting a compound [VII] or a salt thereof with a compound [V] or a salt thereof.

Suitable salts of the compounds [Id], [VII] and [V] may be the same as those exemplified for the compound [I].

This reaction can be carried out in a similar manner to that of Example 7 mentioned below.

Process 6

The object compound [Ig] or a salt thereof can be prepared by subjecting a compound [Ie] or a salt thereof to deesterification reaction followed by subjecting a compound [If] or a salt thereof to elimination reaction of the amino protective group.

Suitable salts of the compound [Ig], [Ie] and [If] may be the same as those exemplified for the compound [I].

These reactions can be carried out in a similar manner to that of Example 18 mentioned below.

The compounds obtained by the above processes can be isolated and purified by a conventional method such as pulverization, recrystallization, column chromatography, reprecipitation, or the like, and converted to the desired salt in conventional manners, if necessary.

It is to be noted that the compound [I] and the other compounds may include one or more stereoisomers due to asymmetric carbon atoms, and all of such isomers and mixture thereof are included within the scope of this invention.

It is further to be noted that isomerization or rearrangement of the object compound [I] may occur due to the effect of the light, acid base or the like, and the compound obtained as the result of said isomerization or rearrangement if also included within the scope of the present invention.

It is also to be noted that the solvating form of the compound [I] (e.g. hydrate, etc.) and any form of the crystal of the compound [I] are included within the scope of the present invention.

The object compound [I] or a salt thereof possesses gut sympathomimetic, anti-ulcerous, anti-pancreatitis, lipolytic, anti-urinary incontinence and anti-pollakiuria activities, and are useful for the treatment and/or prevention of gastrointestinal disorders caused by smooth muscle contractions in human beings or animals, and more parcitularly for the treatment and/or prevention of spasm or hyperanakinesia in case of irritable bowel syndrome, gastritis, gastric ulcer, duodenal ulcer, enteritis, cholecystopathy, cholantitis, urinary calculus and the like; for the treatment and/or prevention of ulcer such as gastric ulcer, duodenal ulcer, peptic ulcer, ulcer causes by non steroidal anti-inflammatory drags, or the like; for the treatment and/or prevention of dysuria or overactive bladder disorder such as pollakiuria, urinary incontinence, urge incontinence or the like in case of nervous pollakiuria, neurogenic bladder dysfunction, nocturia, unstable bladder, cystospasm, chronic cystitis, chronic prostatitis, prostatic hypertrophy or the like; for the treatment and/or prevention of pancreatitis, obesity, diabetes, glycosuria, hyperlipidemia, hypertension, atherosclerosis, glaucoma, melancholia, depression or the like; for the treatment and/or prevention of diseases as the result of insulin resistance (e.g. hypertension, hyperinsulinemia, etc.); for the treatment and/or prevention of neurogenetic inflammation; and for reducing a wasting condition, and the like.

Additionally, $\beta_3$ adrenergic receptor agonists are known to lower triglyceride and cholesterol levels and to raise high density lipoprotein levels in mammals (U.S. Pat. No. 5,451, 677). Accordingly, the object compound [I] in useful in the treatment and/or prevention of conditions such as hyper-triglyceridaemia, hypercholesterolaemia and in lowering high density lipoprotein levels as well as in the treatment of atherosclerotic and cardiovascular diseases and relates conditions.

Moreover, the object compound [I] is useful for inhibiting uterine contractions, preventing premature labor, and treating and preventing dysmenorrhea.

In order to show the usefulness of the compound [I] for the prophylactic and therapeutic treatment of above-mentioned disease in human being or animals, a representative compound of the compound [I] was tested on the following pharmaceutical test.

Test

Effect on the increase in intravesical pressure induced by carbachol in anesthetized dog Test Compound (1) 4'-[(2R)-2-[[(2R)-2-Phenyl-2-hydroxyethyl]amino]-propyl]-3-methoxy-1,1'-biphenyl-4-carboxylic acid hydrochloride, (2) 4'-[2-[[(2R)-2-(3-Chlorophenyl)-2-hydroxyethyl]amino]-ethyl]-2,3-dimethyl-1,1'-biphenyl-4-carboxylic acid hydrochloride, (3) 4'-[2-[[(2R)-2-Hydroxy-2-(3-pyridyl)ethyl]amino]ethyl]-2-methyl-1,1'-biphenyl-4-carboxylic acid dihydrochloride, (4) 4'-[(2R)-2-[[(2R)-2-Hydroxy-2-(3-pyridyl)ethyl]amino]-propyl]-3-methoxy-1,1'-biphenyl-4-carboxylic acid dihydrochloride.

Test Method

Female Beagle dogs weighing 8.0-15.0 kg were fasted for 24 hours and maintained under halothane anesthesia. A 12F Foley catheter was lubricated with water soluble jelly, inserted into the urethral orifice and advanced approximately 10 cm until the balloon tip was placed well inside the bladder. The balloon was then inflated with 5 ml of room air and catheter slowly withdrawn just part the first resistance that is felt at the bladder neck. Urine was completely drained out through the catheter, and 30 ml of biological saline was infused. The catheter was connected to pressure transducer, and intravesical pressure (IVP) was continuously recorded. The test compound was administered intravenously at 30 minutes before the administration of carbachol (1.8 µg/kg). Percent inhibition of IVP increase by test compound was calculated by dividing IVPa (IVP increase induced by carbachol after test compound administration) by IVPb (IVP increase induced by carbachol just before test compound administration).

Test Results

| Treatment | Percent inhibition of IVP increase |
| --- | --- |
| Test Compound (1) (0.032 mg/kg) | 93 |
| Test Compound (2) (0.032 mg/kg) | 91 |
| Test Compound (3) (0.032 mg/kg) | 86 |
| Test Compound (4) (0.032 mg/kg) | 96 |

Preferred embodiments of the object compound [I] are as follows:

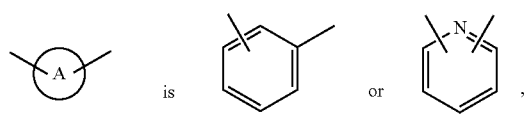

is

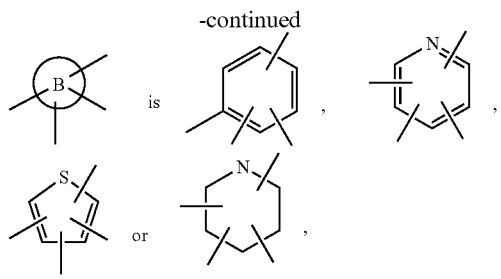

-continued

X is bond, —O—, —OCH$_2$—, —S— or

(in which $R^7$ is hydrogen or lower alkyl (more preferably $C_1$-$C_4$ alkyl, most preferably methyl)), Y is bond, —O—(CH$_2$)$_n$— (in which n is 1, 2, 3 or 4), —(CH$_2$)$_m$— (in which m is 1, 2, 3 or 4),

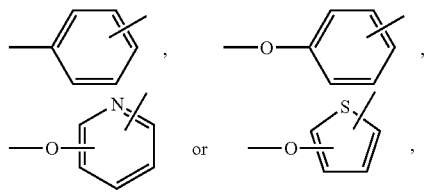

Z is carboxy or lower alkoxycarbonyl (more preferably $C_1$-$C_4$ alkoxycarbonyl, most preferably methoxycarbonyl, ethoxycarbonyl or tert-butoxycarbonyl), $R^1$ is hydrogen or halogen (more preferably chloro), $R^2$ is hydrogen, $R^3$ is hydrogen or lower alkyl (more preferably $C_1$-$C_4$ alkyl, most preferably methyl), $R^4$ is hydrogen, $R^5$ is halogen (more preferably chloro), hydroxy, lower alkyl (more preferably $C_1$-$C_6$, most preferably methyl), lower alkoxy (more preferably $C_1$-$C_6$ alkoxy, most preferably methoxy, ethoxy, propoxy, isopropoxy, butoxy or pentyloxy), hydroxy(lower)alkoxy (more preferably hydroxy ($C_1$-$C_4$)alkyl, most preferably 2-hydroxyethoxy), mono(or di or tri)halo(lower)alkoxy (more preferably mono(or di or tri)halo($C_1$-$C_4$)alkoxy, most preferably 2-fluoroethoxy, 2,2-difluoroethoxy, 2,2,2-trifluoroethoxy, 3-fluoropropoxy or 3,3,3-trifluoropropoxy), lower alkoxy(lower)alkoxy (more preferably $C_1$-$C_4$ alkoxy($C_1$-$C_4$)alkoxy, most preferably 2-methoxyethoxy), lower alkenyloxy (more preferably $C_2$-$C_4$ alkenyl, most preferably allyloxy), cyclo(lower)alkyloxy (more preferably cyclo($C_3$-$C_6$)alkyloxy, most preferably cyclohexyloxy), phenoxy or phenyl, $R^6$ is hydrogen, $R^8$ is hydrgen or lower alkyl (more preferably $C_1$-$C_4$ alkyl, most preferably methyl), $R^9$ is hydrogen or lower alkyl (more preferably $C_1$-$C_4$ alkyl, most preferably methyl), and i is 1 or 2.

More preferred embodiments of the object compound [I] are as follows:

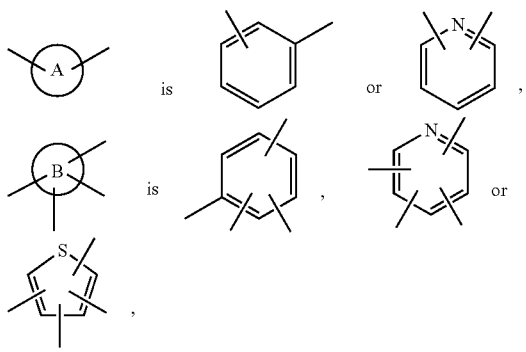

X is bond, —O—, —OCH$_2$—, —S— or

(in which R$^7$ is hydrogen or lower alkyl (more preferably C$_1$-C$_4$ alkyl, most preferably methyl)),
Y is bond, —O—(CH$_2$)$_n$— (in which n is 1 or 2) or —(CH$_2$)$_m$— (in which m is 1 or 2),
Z is carboxy or lower alkoxycarbonyl (more preferably C$_1$-C$_4$ alkoxycarbonyl, most preferably methoxycarbonyl, ethoxycarbonyl or tert-butoxycarbonyl),
R$^1$ is hydrogen or halogen (more preferably chloro),
R$^2$ is hydrogen,
R$^3$ is hydrogen or lower alkyl (more preferably C$_1$-C$_4$ alkyl, most preferably methyl),
R$^4$ is hydrogen,
R$^5$ is hydrogen, halogen (more preferably chloro), hydroxy, lower alkyl (more preferably C$_1$-C$_6$, most preferably methyl), or lower alkoxy (more preferaly C$_1$-C$_6$ alkoxy, most preferably methoxy),
R$^6$ is hydrogen,
R$^8$ is hydrogen or lower alkyl (more preferably C$_1$-C$_4$ alkyl, most preferably methyl), and
i is 1.

Further more preferred embodiments of the compound [I] are as follows:

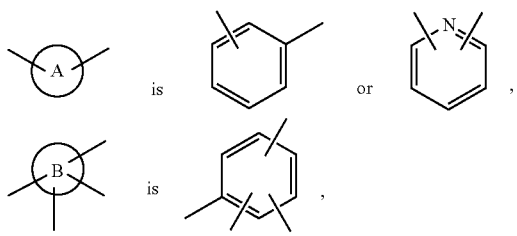

X is bond,
Y is bond,
Z is carboxy or lower alkoxycarbonyl (more preferably C$_1$-C$_4$ alkoxycarbonyl, most preferably methoxycarbonyl, ethoxycarbonyl or tert-butoxycarbonyl),
R$^1$ is hydrogen or halogen (more preferably chloro),
R$^2$ is hydrogen,
R$^3$ is hydrogen or lower alkyl (more preferably C$_1$-C$_4$ alkyl, most preferably methyl),
R$^4$ is hydrogen,
R$^5$ is hydrogen (more preferably chloro), hydroxy, lower alkyl (more preferably C$_1$-C$_4$ alkyl, most preferably methyl) or lower alkoxy (more preferably C$_1$-C$_4$ alkoxy, most preferably methoxy or ethoxy),
R$^6$ is hydrogen,
R$^8$ is hydrogen or lower alkyl (more preferably C$_1$-C$_4$ alkyl, most preferably methyl),
R$^9$ is hydrogen or lower alkyl (more preferably C$_1$-C$_4$ alkyl, most preferably methyl), and
i is 1.

The following Preparations and Examples are given for the purpose of illustrating this invention.

Preparation 1

A solution of N-benzyl-2-(4-bromophenyl)ethanamine (13.5 g) in ethanol (270 ml) was added (2R)-2-(3-chlorophenyl)oxirane (8.63 g) and the solution was refluxed for 48 hours. After cooling to room temperature, the solvent was removed by evaporation and the residue was chromatographed on silica gel (eluent: hexane/ethyl acetate=9/1) to give (1R)-2-[benzyl[2-(4-bromophenyl)ethyl]amino]-1-(3-chlorophenyl)ethanol (18.6 g) as a colorless oil.

NMR (CDCl$_3$, δ): 2.58 (1H, dd, J=10, 13 Hz), 2.68-2.89 (5H, m), 3.56 (1H, d, J=13 Hz), 3.92 (1H, d, J=13 Hz), 4.59 (1H, dd, J=3.4, 10 Hz), 6.97 (2H, d, J=8.3 Hz), 7.21-7.40 (12H, m) (+)ESI-MS (m/z): 444 and 446 (MH$^+$)

Preparation 2

To a solution of (1R)-2-[benzyl[2-(4-bromophenyl)ethyl]amino]-1-(3-chlorophenyl)ethanol (18.5 g) in N,N-dimethylformamide (40 ml) were successively added imidazole (3.96 g) and tert-butyldimethylsilyl chloride (7.52 g) and the solution was stirred at room temperature for 14 hours. The reaction mixture was quenched by the addition of water (100 ml) and extracted with ethyl acetate (100 ml×1). The extract was washed with water (100 ml×2), brine (100 ml×1), and dried over magnesium sulfate. Filtration followed by evaporation gave a colorless oil, which was chromatographed on silica gel (eluent: hexane/ethyl acetate) to give (2R)-N-benzyl-N-[2-(4-bromophenyl)ethyl]-2-[[tert-butyl(dimethyl)silyl]oxy]-2-(3-chlorophenyl)ethanamine (21.0 g) as a colorless oil.

NMR (CDCl$_3$, δ): 0.15 (6H, s), 1.01 (9H, s), 2.72-2.82 (5H, m), 2.92 (1H, dd, J=5.9, 13 Hz), 3.75 (1H, d, J=13.7 Hz), 3.86 (1H, d, J=13.7 Hz), 4.71 (1H, t-like, J=6.2 Hz), 7.01 (2H, d, J=8.3 Hz), 7.26-7.47 (9H, m), 7.48 (2H, d, J=8.3 Hz) (+)ESI-MS (m/z): 558 and 560 (MH$^+$)

Preparation 3

To a solution of tert-butyl [2-(4-bromophenyl)ethyl][(2R)-2-(3-chlorophenyl)-2-hydroxyethyl]carbamate (500 mg) in 1,2-dimethoxyethane (6 ml) was added 5-formyl-2-thiopheneboronic acid (206 mg), tetrakis(triphenylphosphine)palladium (63 mg) and aqueous solution of sodium carbonate (2M, 1.0 ml), and the mixture was stirred at 80° C. for 7 hours under nitrogen. The mixture was diluted with ethyl acetate and water. The organic layer was separated, washed with brine, dried over magnesium sulfate and evaporated under reduced pressure. The residue was purified by column chromatography on silica gel (hexane/ethyl acetate=3/1) to give tert-butyl [(2R)-2-(3-chlorophenyl)-2-hydrxyethyl][2-[4-(5-formyl-2-thienyl)phenyl]ethyl]carbamate (187 mg).

(+)ESI-MS (m/z): 508 (M+Na)$^+$

Preparation 4

To a suspension of tert-butyl [(2R)-2-(3-chlorophenyl)-2-hydroxyethyl][2-(4-hydroxyphenyl)ethyl]carbamate (710 mg), 4-[[tert-butyl(dimethyl)silyl]oxy]phenylboronic acid (457 mg), triethylamine (1.26 ml) and powdered 4 Å molecular sieves (700 mg) in dichloromethane (18 ml) was added copper(II) acetate (330 mg), and the mixture was stirred at room temperature for 18 hours under ambient atmosphere. The resulting slurry was filtered off, and the filtrate was evaporated under reduced pressure. The residue was purified by column chromatography on silica gel (hexane/ethyl acetate=2/1) to give tert-butyl [2-[4-[4-[[tert-butyl(dimethyl)-silyl]oxy]phenoxy]phenyl]ethyl][(2R)-2-(3-chlorophenyl)-2-hydroxyethyl]carbamate (600 mg).

(−)ESI-MS (m/z): 569 (M−H)−

Preparation 5

The following compounds were obtained according to a similar manner to that of Preparation 4.

(1) tert-Butyl [2-[4-[[4-[[tert-butyl(dimethyl)silyl]oxy]-phenyl]amino]phenyl]ethyl][(2R)-2-(3-chlorophenyl)-2-hydroxyethyl]carbamate (+)ESI-MS (m/z): 597 (M+H)+

(2) tert-Butyl [2-[4-[[4-[[tert-butyl(dimethyl)silyl]oxy]-phenyl](methyl)amino]phenyl]ethyl][(2R)-2-(3-chlorophenyl)-2-hydroxyethyl]carbamate (+)ESI-MS (m/z): 611 (M+H)+

Preparation 6

To a solution of tert-butyl [2-(4-aminophenyl)-ethyl][(2R)-2-(3-chlorophenyl)-2-hydroxyethyl]carbamate (1.75 g) and formaldehyde (37% w/w solution in water, 390 μl) in 1,2-dichloroethane (20 ml) was added sodium triacetoxyborohydride (1.23 g), and the mixture was stirred at room temperature for 18 hours under nitrogen atmosphere. The resulting mixture was poured into a mixture of 1N sodium hydroxide and chloroform, and the mixture was stirred for 20 minutes. The organic layer was separated, washed with brine, dried over magnesium sulfate and evaporated under reduced pressure. The residue was purified by column chromatography on silica gel (hexane/ethyl acetate=2/1) to give tert-butyl [(2R)-2-(3-chlorophenyl)-2-hydroxyethyl](2-[4-(methylamino)phenyl]ethyl]carbamate (550 mg).

(+)ESI-MS (m/z): 405 (M+H)+

Preparation 7

To a suspension of 2-[4-[(4-methoxyphenyl)thio]phenyl]-ethanamine (6.3 g) in methanol (45 ml) and tetrahydrofuran (10 ml) was added ethyl trifluoroacetate (2.89 ml), and the mixture was stirred at room temperature for 1 hour. The mixture was evaporated under reduced pressure. The residue was purified by column chromatography on silica gel (hexane/ethyl acetate=2/1) to give 2,2,2-trifluoro-N-[2-[4-[(4-methoxyphenyl)thio]phenyl]ethyl]acetamide (3.95 g).

(+)ESI-MS (m/z): 378 (M+Na)+

Preparation 8

Under nitrogen at 4° C., to a solution of 2,2,2-trifluoro-N-[2-[4-[(4-methoxyphenyl)thio]phenyl]ethyl]-acetamide (1.5 g) in dichloromethane (15 ml) was added 1M boron tribromide in dichloromethane (10.5 ml), and the mixture was stirred at room temperature for 15 hours. The mixture was evaporated under reduced pressure. The residue was dissolved in a mixture of dichloromethane and saturated aqueous sodium bicarbonate. After separation, the organic layer was dried over magnesium sulfate and evaporated under reduced pressure to give 2,2,2-trifluoro-N-[2-[4-[(4-hydroxyphenyl)thio]phenyl]ethyl]acetamide (1.42 g).

(+)ESI-MS (m/z): 364 (M+Na)+

Preparation 9

To a solution of 2,2,2-trifluoro-N-[2-[4-[(4-hydroxyphenyl)thio]phenyl]ethyl]acetamide (480 mg) in methanol (5.0 ml) was added 1N sodium hydroxide solution (2.8 ml). The mixture was refluxed for 12 hours. The mixture was evaporated under reduced pressure. The residue was dissolved in a mixture of dichloromethane (40 ml), 1N hydrochloric acid solution (2.0 ml) and water (15 ml). After separation, the organic layer was dried over magnesium sulfate and evaporated under reduced pressure to give 4-[[4-(2-aminoethyl)phenyl]thio]phenol (300 mg).

(−)ESI-MS (m/z): 244 (M−H)−

Preparation 10

4-[[4-(2-Aminoethyl)phenyl]thio]phenol (295 mg) and (2R)-2-(3-chlorophenyl)oxirane (186 mg) in ethanol (3.5 ml) was refluxed for 6 hours. The mixture was evaporated. The residue was purified by column chromatography on silica gel (chloroform/methanol=100/3) to give 4-[[4-[2-[[(2R)-2-(3-chlorophenyl)-2-hydroxyethyl]amino]ethyl]phenyl]thio]phenol (155 mg).

(+)ESI-MS (m/z): 400 (M+H)+

The object compound above was protected at the imino group in a conventional manner to give tert-butyl [(2R)-2-(3-chlorophenyl)-2-hydroxyethyl][2-[4-[(4-hydroxyphenyl)thio]phenyl]ethyl]carbamate (200 mg).

(+)ESI-MS (m/z): 500 (M+H)+

Preparation 11

The following compounds were obtained according to a similar manner to that of Preparation 10.

(1) (1R)-2-[(2-(4-Bromophenyl)ethyl]amino]-1-(3-chlorophenyl)ethanol (+)ESI-MS (m/z): 354 (M+H)+

(2) tert-Butyl [2-(4-bromophenyl)ethyl][(2R)-2-(3-chlorophenyl)-2-hydroxyethyl]carbamate (+)ESI-MS (m/z): 454 (M+H)+

EXAMPLE 1

To a solution of tert-butyl [(2R)-2-(3-chlorophenyl)-2-hydroxyethyl][2-[4-(5-formyl-2-thienyl)phenyl]ethyl]-carbamate (180 mg) in acetonitrile (2 ml) and pH 4 buffer solution (sodium dihydrogenphosphate) (1 ml) was added 30% hydrogen peroxide solution (30 μl) and 80% sodium chlorite (67 mg) below 10° C. The reaction mixture was stirred at 50° C. for 3 hours. The mixture was diluted with ethyl acetate, washed with water and brine, dried over magnesium sulfate and evaporated under reduced pressure to give 5-[4-[2-[(tert-butoxycarbonyl)[(2R)-2-(3-chlorophenyl)-2-hydroxyethyl]amino]ethyl]phenyl]-2-thiophenecarboxylic acid (160 mg).

(−)ESI-MS (m/z): 500 (M−H)−

EXAMPLE 2

The following compounds were obtained according to a similar manner to that of Example 4.

(1) 5-[4-[2-[[(2R)-2-(3-Chlorophenyl)-2-hydroxyethyl]-amino]ethyl]phenyl]-2-thiophenecarboxylic acid hydrochloride NMR (DMSO-$d_6$, δ): 3.00-3.25 (6H, m), 4.95-4.99 (1H, m), 6.34 (1H, br), 7.33-7.47 (6H, m), 7.55 (1H, d, J=3.9 Hz), 7.70-7.81 (3H, m), 9.05 (1H, br) (−)ESI-MS (m/z): 400 (M−HCl−H)−

(2) [4-[[4-[2-[[(2R)-2-(3-Chlorophenyl)-2-hydroxyethyl]-amino]ethyl]phenyl]amino]phenoxy]acetic acid hydrochloride NMR (DMSO-d$_6$, δ): 2.84-3.30 (6H, m), 4.39 (1H, br), 4.59 (2H, s), 4.97-5.03 (1H, m), 6.37 (1H, br), 6.80-7.07 (8H, m), 7.34-7.48 (4H, m), 8.85 (1H, br), 9.11 (1H, br) (−)ESI-MS (m/z): 439 (M−HCl−H)$^-$ (3) [4-[[4-[2-[[(2R)-2-(3-Chlorophenyl)-2-hydroxyethyl]-amino]ethyl]phenyl](methyl)amino]phenoxy]acetic acid hydrochloride NMR (DMSO-d$_6$, δ): 2.85-3.23 (6H, m), 3.17 (3H, s), 3.89-4.15 (1H, br), 4.65 (2H, s), 4.98-5.02 (1H, m), 6.68-7.08 (8H, m), 7.34-7.46 (4H, m), 8.86 (1H, br), 9.14 (1H, br) (−)ESI-MS (m/z): 453 (M−HCl−H)$^-$ (4) [4-[[4-[2-[[(2R)-2-(3-Chlorophenyl)-2-hydroxyethyl]-amino]ethyl]phenyl]thio]phenoxy]acetic acid hydrochloride NMR (DMSO-d$_6$, δ): 2.94-3.33 (6H, m), 4.70 (2H, s), 4.97-5.01 (1H, m), 6.34 (1H, br), 6.96 (2H, d, J=8.7 Hz), 7.02-7.23 (4H, m), 7.33-7.45 (6H, m), 8.97-9.18 (1H, br) (−)ESI-MS (m/z): 456 (M−HCl−H)$^-$

EXAMPLE 3

To a solution of tert-butyl [2-[4-[4-[[tert-butyl(dimethyl)silyl]oxy]phenoxy]phenyl]ethyl][(2R)-2-(3-chlorophenyl)-2-hydroxyethyl]carbamate (370 mg) in tetrahydrofuran (4.0 ml) was added 1M tetrabutylammonium fluoride in tetrahydrofuran (1.2 ml), and the mixture was stirred at room temperature for 1 hour. The mixture was partitioned between ethyl acetate and water. The organic layer was separated, washed with water and brine, dried over magnesium sulfate and evaporated under reduced pressure to give a phenol product. To a solution of the product and potassium carbonate (94 mg) in N,N-dimethylformamide (4.0 ml) was added tert-butyl bromoacetate (133 mg), and the mixture was stirred at room temperature for 5 hours. The mixture was partitioned between ethyl acetate and water. The organic layer was separated, washed with water and brine, dried over magnesium sulfate and evaporated under reduced pressure. The residue was purified by column chromatography on silica gel (hexane/ethyl acetate=2/1) to give tert-butyl [4-[4-[2-[(tert-butoxycarbonyl)[(2R)-2-(3-chlorophenyl)-2-hydroxyethyl]amino]ethyl]phenoxy]phenoxy]-acetate (360 mg).

(−)ESI-MS (m/z): 597 (M−H)$^-$

EXAMPLE 4

A solution of tert-butyl [4-[4-[2-[(tert-butoxycarbonyl)[(2R)-2-(3-chlorophenyl)-2-hydroxyethyl]-amino]ethyl]phenoxy]phenoxy]acetate (305 mg) and 4N hydrochloride in 1,4-dioxane (5.0 ml) was stirred at room temperature for 24 hours. The resulting solid was collected by filtration and dried to give [4-[4-[2-[[(2R)-2-(3-chlorophenyl)-2-hydroxyethyl]aminoethyl]phenoxy]phenoxy]-acetic acid hydrochloride (220 mg) as a white solid.

NMR (DMSO-d$_6$, δ): 2.95-3.33 (6H, m), 4.65 (2H, s), 4.99-5.04 (1H, m), 6.35 (1H, br), 6.83-7.00 (6H, m), 7.23 (9H, d, J=8.5 Hz), 7.39-7.47 (4H, m), 8.98-9.12 (1H, br) (+)ESI-MS (m/z): 442 (M−HCl+H)$^+$

EXAMPLE 5

To a suspension of tert-butyl [(2R)-2-(3-chlorophenyl)-2-hydroxyethyl][2-(4-hydroxyphenyl)ethyl]carbamate (550 mg), (4-methoxycarbonylphenyl)boronic acid (300 mg), triethylamine (1.0 ml) and powdered 4 Å molecular sieves (600 mg) in dichloromethane (8 ml) was added copper(II) acetate (255 mg), and the mixture was stirred at room temperature for 18 hours under ambient atmosphere. The resulting slurry was filtered off, and the filtrate was evaporated under reduced pressure. The residue was purified by column chromatography on silica gel (hexane/ethyl acetate=2/1) to give methyl 4-[4-[2-[(tert-butoxycarbonyl)[(2R)-2-(3-chlorophenyl)-2-hydroxyethyl]amino]ethyl]phenoxy]benzoate (185 mg).

(+)ESI-MS (m/z): 526 (M+H)$^+$

EXAMPLE 6

To a solution of methyl 4-[4-[2-[(tert-butoxycarbonyl)[(2R)-2-(3-chlorophenyl)-2-hydroxyethyl]amino]ethyl]phenoxy]benzoate (183 mg) in ethanol (1.2 ml) was added 1N aqueous sodium hydroxide solution (0.6 ml), and the mixture was stirred at 40° C. for 3 hours. The solvent was removed by evaporation, and the aqueous solution was acidified with 1N aqueous hydrochloride solution and extracted with ethyl acetate (30 ml×2). The combined organic layers were washed with water and brine, dried over magnesium sulfate and evaporated under reduced pressure to give a benzoic acid product. To a solution of the product in tetrahydrofuran (2.0 ml) was added 4N hydrochloride in 1,4-dioxane (1.0 ml), and the mixture was stirred at room temperature for 12 hours. The resulting solid was collected by filtration and dried to give 4-[4-[2-[[(2R)-2-(3-chlorophenyl)-2-hydroxyethyl]amino]ethyl]-phenoxy]benzoic acid hydrochloride (127 mg).

NMR (DMSO-d$_6$, δ): 3.00-3.28 (6H, m), 4.99-5.04 (1H, m), 6.35 (H, br), 6.97-7.12 (4H, m), 7.32-7.48 (6H, m), 7.90-7.98 (2H, m), 9.03-9.35 (1H, br) (−)ESI-MS (m/z): 410 (M−HCl−H)$^-$

EXAMPLE 7

To a solution of tert-butyl [2-(4-bromophenyl)ethyl]-[(2R)-2-(3-chlorophenyl)-2-hydroxyethyl]carbamate (400 mg) in 1,2-dimethoxyethane (6 ml) was added (4-methoxycarbonyl-2-methylphenyl)boronic acid (171 mg), tetrakis(triphenylphosphine)palladium (55 mg) and aqueous solution of sodium carbonate (2M, 0.92 ml), and the mixture was stirred at 80° C. for 2 hours under nitrogen. The mixture was diluted with ethyl acetate and water. The organic layer was separated, washed with brine, dried over magnesium sulfate and evaporated under reduced pressure. The residue was purified by column chromatography on silica gel (hexane/ethyl acetate=2/1) to give methyl 4'-[2-[(tert-butoxycarbonyl)[(2R)-2-(3-chlorophenyl)-2-hydroxyethyl]-amino]ethyl]-2-methyl-1,1'-biphenyl-4-carboxylate (320 mg).

(+)ESI-MS (m/z): 524 (M+H)$^+$

EXAMPLE 8

The following compounds were obtained according to a similar manner to that of Example 6.

1) 5-Chloro-6-[4-[2-[[(2R)-2-(3-chlorophenyl)-2-hydroxyethyl]amino]ethyl]phenoxy]nicotinic acid hydrochloride NMR (DMSO-d$_6$, δ): 3.04-3.32 (6H, m), 5.03-5.07 (1H, m), 5.14 (1H, br), 7.18 (2H, d, J=8.5 Hz), 7.33-7.48 (6H, m), 8.38 (1H, d, J=2.0 Hz), 8.54 (1H, d, J=2.0 Hz), 9.00 (1H, br), 9.35 (1H, br) (−)ESI-MS (m/z): 445 (M−HCl−H)$^-$ (2) 4'-[2-[[(2R)-2-(3-Chlorophenyl)-2-hydroxyethyl]amino]-ethyl]-2-methyl-1,1'-biphenyl-4-carboxylic acid hydrochloride NMR (DMSO-d$_6$, δ): 2.28 (1H, s), 3.01-3.27 (6H, m), 5.00-5.04 (1H, m), 6.36 (1H, br), 7.28-7.48 (9H, m), 7.79-7.90 (2H, m), 9.02 (1H, br) (−)ESI-MS (m/z): 408 (M−HCl−H)$^-$

EXAMPLE 9

To a solution of tert-butyl [(2R)-2-(3-chlorophenyl)-2-hydroxyethyl][2-(4-hydroxyphenyl)ethyl]carbamate (600 mg) and potassium carbonate (254 mg) in dimethylsulfoxide (6.0 ml) was added methyl 5,6-dichloro-3-pyridinecarboxylate (347 mg), and the mixture was stirred at room temperature for 12 hours. The mixture was partitioned between ethyl acetate and water. The organic layer was separated, washed with water and brine, dried over magnesium sulfate and evaporated under reduced pressure. The residue was purified by column chromatography on silica gel (hexane/ethyl acetate=2/1) to give methyl 6-[4-[2-[(tert-butoxycarbonyl)[(2R)-2-(3-chlorophenyl)-2-hydroxyethyl]amino]ethyl]phenoxy]-5-chloronicotinate (770 mg).

(+)ESI-MS (m/z): 561 (M+H)$^+$

EXAMPLE 10

Under nitrogen at 5° C., to a solution of tert-butyl [(2R)-2-(3-chlorophenyl)-2-hydroxyethyl][2-(4-hydroxyphenyl)ethyl]carbamate (1.5 g), ethyl [3-(hydroxymethyl)phenoxy]acetate (885 mg) and triphenyl phosphine (1.1 g) in tetrahydrofuran (30 ml) was added diethyl azodicarboxylate (0.66 ml). The mixture was stirred at room temperature for 12 hours and evaporated under reduced pressure. The residue was purified by column chromatography on silica gel (hexane/ethyl acetate=2/1) to give ethyl [3-[[4-[2-[(tert-butoxycarbonyl)[(2R)-2-(3-chlorophenyl)-2-hydroxyethyl]amino]ethyl]phenoxy]methyl]-phenoxy]acetate (1.04 g).

(+)ESI-MS (m/z): 585 (M+H)$^+$

EXAMPLE 11

To a solution of ethyl [3-[[4-[2-[(tert-butoxycarbonyl)[(2R)-2-(3-chlorophenyl)-2-hydroxyethyl]-amino]ethyl]phenoxy]methyl]phenoxy]acetate (1.0 g) in tetrahydrofuran (5.0 ml) was added 4N hydrochloride in dioxane (4.3 ml). The mixture was stirred at room temperature for 8 hours and evaporated under reduced pressure. The residue was diluted with ethyl acetate and saturated sodium bicarbonate solution. The organic layer was separated, washed with brine, dried over magnesium sulfate and evaporated under reduced pressure. The residue was purified by column chromatography on silica gel (methanol/chloroform=1/20) to give ethyl [3-[[4-[2-[[(2R)-2-(3-chlorophenyl)-2-hydroxyethyl]amino]ethyl]phenoxy]-methyl]phenoxy]acetate (632 mg).

(+)ESI-MS (m/z): 484 (M+H)$^+$

The object compound above was hydrolyzed in a conventional manner to give sodium [3-[[4-[2-[[(2R)-2-(3-chlorophenyl)-2-hydroxyethyl]amino)ethyl]phenoxy]methyl]-phenoxy]acetate (492 mg).

NMR (DMSO-d$_6$, δ): 2.56-2.73 (6H, m), 4.09 (2H, s), 4.58-4.64 (1H, m), 4.98 (2H, s), 6.72-6.77 (1H, m), 6.85-6.91 (4H, m), 7.08 (2H, d, J=8.5 Hz), 7.17-7.26 (4H, m), 7.38 (1H, s) (−)ESI-MS (m/z): 454 (M−Na−H)$^-$

EXAMPLE 12

The following compounds were obtained according to a similar manner to that of Example 3.

(1) tert-Butyl [4-[[4-[2-[(tert-butoxycarbonyl)[(2R)-2-(3-chlorophenyl)-2-hydroxyethyl]amino]ethyl]phenyl]amino]-phenoxy)acetate (+)ESI-MS (m/z): 597 (M+H)$^+$ (2) tert-Butyl [4-[[4-[2-[(tert-butoxycarbonyl)][(2R)-2-(3-chlorophenyl)-2-hydroxyethyl]amino]ethyl]phenyl]-(methyl)amino]phenoxy]acetate (+)ESI-MS (m/z): 611 (M+H)$^+$

EXAMPLE 13

To a solution of tert-butyl [(2R)-2-(3-chlorophenyl)-2-hydroxyethyl][2-[4-[(4-hydroxyphenyl)thio]phenyl]ethyl]-carbamate (195 mg) and potassium carbonate (59 mg) in N,N-dimethylformamide (3 ml) was added tert-butyl bromoacetate (84 mg), and the mixture was stirred at room temperature for 3 hours. The mixture was partitioned between ethyl acetate and water. The organic layer was separated, washed with water and brine, dried over magnesium sulfate and evaporated under reduced pressure. The residue was purified by column chromatography on silica gel (hexane/ethyl acetate=3/1) to give tert-butyl [4-[[4-[2-[(tert-butoxycarbonyl)[(2R)-2-(3-chlorophenyl)-2-hydroxyethyl]amino]ethyl]phenyl]thio]-phenoxy]acetate (168 mg).

(+)ESI-MS (m/z): 636 (M+Na)$^+$

Preparation 12

To a solution of 4-bromo-2-fluorobenzoate (1.5 g) in N,N-dimethylformamide (30 ml) was added bis(pinacolato)-diboron (1.8 g), 1,1'-bis(diphenylphosphino) ferrocene-palladium (II)dichlotidedichloromethane complex (1:1) (263 mg) and potassium acetate (1.9 g), and the mixture was stirred at 100° C. for 18 hours under nitrogen. The mixture was diluted with ethyl acetate and water. The organic layer was separated, washed with brine, dried over magnesium sulfate and evaporated. The residue was purified by column chromatography on silica gel (hexane/ethyl acetate=5/1) to give methyl 2-fluoro-4-(4,4,5,5-tetramethyl-1,3,2-dioxaborolan-2-yl)benzoate (350 mg).

(+)ESI-MS (m/z): 303 (M+Na)$^+$

Preparation 13

To a solution of methyl 4-bromo-2-methoxybenzoate (2.0 g) in 1,4-dioxane (40 ml) was added bis(pinacolato)diboron (2.07 g), dichlorobis(triphenylphosphine)palladium(II) (286 mg) and potassium acetate (2.4 g), and the mixture was stirred at 95° C. for 10 hours under nitrogen. The mixture was diluted with ethyl acetate and water. The organic layer was separated, washed with brine, dried over magnesium sulfate and evaporated. The residue was purified by column chromatography on silica gel (hexane/ethyl acetate=3/1) to give methyl 2-methoxy-4-(4,4,5,5-tetramethyl-1,3,2-dioxaborolan-2-yl)benzoate (2.0 g).

(+)ESI-MS (m/z): 293 (M+H)$^+$

Preparation 14

To a suspension of methyl 2-methoxy-4-(4,4,5,5-tetramethyl-1,3,2-dioxaborolan-2-yl)benzoate (2.0 g) in acetone (70 ml) and water (70 ml) was added ammonium acetate (1.11 g) and sodium periodate (3.08 g), and the mixture was stirred at room temperature for 15 hours. The solvent was evaporated and the residue was diluted with ethyl acetate. The organic layer was separated, washed with water and brine, dried over magnesium sulfate and evaporated under reduced pressure to give [3-methoxy-4-(methoxycarbonyl)phenyl]-boronic acid (1.4 g).

(+)ESI-MS (m/z): 209 (M−H)$^-$

Preparation 15

The following compounds were obtained according to a similar manner to that of Preparation 14.

(1) [3-Fluoro-4-(methoxycarbonyl)phenyl]boronic acid (+)ESI-MS (m/z): 197 (M−H)$^-$ (2) [2-Chloro-4-(methoxycarbonyl)phenyl]boronic acid
(+)ESI-MS (m/z): 213 (M–H)⁻
(3) [4-(Ethoxycarbonyl)-2-methoxyphenyl]boronic acid
(+)ESI-MS (m/z): 223 (M–H)⁻

Preparation 16

To a solution of ethyl 3-methoxy-4-[[(trifluoromethyl)-sulfonyl]oxy]benzoate (1.52 g) in 1,4-dioxane (35 ml) was added bis(pinacolato)diboron (1.18 g), 1,1'-bis(diphenyl-phosphino) ferrocene-palladium(II)dichloridedichloromethane complex (1:1) (309 mg) and potassium acetate (1.36 g), and the mixture was stirred at 100° C. for 10 hours under nitrogen. The mixture was diluted with ethyl acetate and water. The organic layer was separated, washed with brine, dried over magnesium sulfate and evaporated. The residue was purified by column chromatography on silica gel (hexane/ethyl acetate=5/1) to give ethyl 3-methoxy-4-(4,4,5,5-tetramethyl-1,3,2-dioxaborolan-2-yl)benzoate (700 mg).
(+)ESI-MS (m/z): 293 (M+H)⁺

Preparation 17

The following compound was obtained according to a similar manner to that of Preparation 16.
Methyl 3-chloro-4-(4,4,5,5-tetramethyl-1,3,2-dioxaborolan-2-yl)benzoate
(+)ESI-MS (m/z): 297 (M+H)⁺

Preparation 18

To a solution of tert-butyl [(2R)-2-(3-chlorophenyl)-2-hydroxyethyl][2-(4-hydroxyphenyl)ethyl]carbamate (5.0 g) and 2,6-lutidine (2.97 ml) in dichloromethane (75 ml) was added trifluoromethanesulfonic anhydride (2.36 ml) dropwise at –70° C. under nitrogen and the mixture was stirred at –70° C. for 30 minutes. The mixture was allowed to warm to room temperature and evaporated under reduced pressure. The residue was partitioned between ethyl acetate and water. The organic layer was separated, washed with saturated sodium biscarbonate solution and brine, dried over magnesium sulfate and evaporated under reduced pressure. The residue was purified by column chromatography on silica gel (hexane/ethyl acetate=2/1) to give 4-[2-[(tert-butoxycarbonyl)[(2R)-2-(3-chlorophenyl)-2-hydroxyethyl]-amino]ethyl]phenyl trifluoromethanesulfonate (6.6 g).
(+)ESI-MS (m/z): 546 (M+Na)⁺

Preparation 19

To a solution of methyl 4-bromo-2-methylbenzoate (6.9 g) in 1,4-dioxane (150 ml) was added bis(pinacolato)diboron (8.03 g), dichlorobis(triphenylphosphine)palladium(II) (1.69 g) and potassium acetate (8.87 g), and the mixture was stirred at 95° C. for 2 hours under nitrogen. The mixture was diluted with ethyl acetate and water. The organic layer was separated, washed with 1N hydrochloric acid and brine, dried over magnesium sulfate and evaporated. To a suspension of the crude product (11 g) in acetone (200 ml) and water (200 ml) was added ammonium acetate (5.1 g) and sodium periodate (14.1 g), and the mixture was stirred at room temperature for 6 hours. The solvent was evaporated, and the mixture was diluted with ethyl acetate. The organic layer was separated, washed with water and brine, dried over magnesium sulfate and evaporated under reduced pressure. The resultant solid was triturated with diisopropyl ether to give [3-methyl-4-(methoxycarbonyl)phenyl]boronic acid (2.65 g).
(+)ESI-MS (m/z): 193 (M–H)⁻

Preparation 20

To a solution of 4-hydroxy-2,3-dimethylbenzaldehyde (1.9 g) and pyridine (5.12 ml) in dichloromethane (40 ml) was added trifluoromethanesulfonic anhydride (2.34 ml) under nitrogen and the mixture was stirred at room temperature for 30 minutes and evaporated under reduced pressure. The residue was partitioned between ethyl acetate and water. The organic layer was separated, washed with saturated sodium bicarbonate solution and brine, dried over magnesium sulfate and evaporated under reduced pressure to give 4-formyl-2,3-dimethylphenyl trifluoromethanesulfonate (2.7 g).
(+)ESI-MS (m/z): 281 (M–H)⁻

Preparation 21

To a solution of 4-formyl-2,3-dimethylphenyl trifluoromethanesulfonate (2.5 g) in 1,4-dioxane (50 ml) was added bis(pinacolato)diboron (2.47 g), 1,1'-bis(diphenyl-phosphino)ferrocene-palladium(II)dichloridedichloromethane complex (1:1) (1.09 g) and potassium acetate (2.61 g), and the mixture was stirred at 90° C. for 5 hours under nitrogen. The mixture was diluted with ethyl acetate and water. The organic layer was separated, washed with 1N hydrochloric acid and brine, dried over magnesium sulfate and evaporated. To a suspension of the crude product in acetone (80 ml) and water (80 ml) was added ammonium acetate (1.4 g) and sodium periodate (3.95 g), and the mixture was stirred at room temperature for 6 hours. The solvent was evaporated, and the mixture was diluted with ethyl acetate. The organic layer was separated, washed with water and brine, dried over magnesium sulfate and evaporated under reduced pressure. The residue was purified by column chromatography on silica gel (hexane/ethyl acetate=1/1) to give (4-formyl-2,3-dimethylphenyl)boronic acid (560 mg).
(+)ESI-MS (m/z): 177 (M–H)⁻

Preparation 22

To a solution of N-benzyl-N-[2-(4-bromophenyl)ethyl]-carbamate (1.3 g) in 1,2-dimethoxyethane (20 ml) was added [4-(methoxycarbonyl)-2-methylphenyl]boronic acid (792 mg), tetrakis(triphenylphosphine)palladium (360 mg) and aqueous solution of sodium carbonate (2M, 4.1 ml), and the mixture was stirred at 80° C. for 2 hours under nitrogen. The mixture was diluted with ethyl acetate and water. The organic layer was separated, washed with brine, dried over magnesium sulfate and evaporated under reduced pressure. The residue was purified by column chromatography on silica gel (hexane/ethyl acetate=3/1) to give methyl 4'-[2-[[(benzyloxy)carbonyl]amino]ethyl]-2-methyl-1,1'-biphenyl-4-carboxylate (660 mg).
(+)ESI-MS (m/z): 426 (M+Na)⁺

Preparation 23

To a solution of 2,2,2-trifluoro-N-[3-(4-iodophenyl)-propyl]acetamide (2.5 g) in 1,2-dimethoxyethane (15 ml) was added [4-(methoxycarbonyl)phenyl]boronic acid (1.51 g), tetrakis(triphenylphosphine)palladium (809 mg) and aqueous solution of sodium carbonate (2M, 7 ml), and the mixture was stirred at 75° C. for 10 hours under nitrogen. The mixture was diluted with ethyl acetate and water. The organic layer was separated, washed with brine, dried over magnesium sulfate and evaporated. The residue was purified by column chromatography on silica gel (hexane/ethyl acetate=2/1) to give methyl 4'-[3-[(trifluoroacetyl)amino]propyl]-1,1'-biphenyl-4-carboxylate (920 mg).
MS (m/z): 366 (M+H)

Preparation 24

The following compound was obtained according to a similar manner to that of Preparation 23.
Ethyl 4'-[2-[[(benzyloxy)carbonyl]amino]ethyl]-2-methoxy-1,1'-biphenyl-4-carboxylate
MS (m/z): 434 (M+H)

Preparation 25

A mixture of methyl 4'-[3-[(trifluoroacetyl)amino]-propyl]-1,1'-biphenyl-4-carboxylate (920 mg), 4N hydrochloride in ethanol (2 ml) and ethanol (2 ml) was refluxed for 18 hours. The mixture was evaporated in vacuo. The residue was diluted with ethyl acetate and saturated aqueous sodium bicarbonate solution. The organic layer was separated, washed with brine, dried over magnesium sulfate and evaporated. The residue was purified by column chromatography on silica gel (chloroform:methanol=100:1) to give ethyl 4'-(3-aminopropyl)-1,1'-biphenyl-4-carboxylate (200 mg) as a colorless foam.

MS (m/z): 284 (M+H)

Preparation 26

To a solution of ethyl (1R)-1-(6-chloro-3-pyridyl)-2-([3-(4-iodophenyl)propyl]amino]ethanol (2.0 g) in tetrahydrofuran (3.5 ml) was added di-tert-butyl dicarbonate (53 mg), and the mixture was stirred at room temperature for 2 hours. The mixture was evaporated. The residue was purified by column chromatography on silica gel (hexane/ethyl acetate=2/1) to give tert-butyl [(2R)-2-(6-chloro-3-pyridyl)-2-hydroxyethyl][3-(4-iodophenyl)propyl]-carbamate (2.62 g).

MS (m/z): 517 (M+H)

Preparation 27

To a solution of 2,2,2-trifluoro-N-[(1R)-2-(4-iodophenyl)-1-methylethyl]acetamide in dioxane (10 ml) was added 1N sodium hydroxide (12 ml) and the mixture was stirred for 1 hour at room temperature. The mixture was diluted with ethyl acetate and water. The organic layer was separated, washed with brine, dried over magnesium sulfate and evaporated to give [(1R)-2-(4-iodophenyl)-1-methylethyl]amine (2.34 g) as a yellow oil.

MS (m/z): 262 (M+H)

Preparation 28

A solution of [(1R)-2-(4-iodophenyl)-1-methylethyl]-amine (1.0 g) and 2-chloro-5-[(2R)-2-oxiranyl]pyridine (298 mg) in ethanol (10 ml) was refluxed for 18 hours. The mixture was evaporated in vacuo. To the residue was added di-tert-butyl dicarbonate (418 mg) and tetrahydrofuran (10 ml) and the mixture was stirred at room temperature for 2 hours and then evaporated. The residue was purified by column chromatography on silica gel (hexane/ethyl acetate=1/1) to give tert-butyl [(2R)-2-(6-chloro-3-pyridyl)-2-hydroxyethyl][(1R)-2-(4-iodophenyl)-1-methylethyl]carbamate (700 mg).

MS (m/z): 517 (M+H)

Preparation 29

The following compound was obtained according to a similar manner to that of Preparation 28.

tert-Butyl [(2R)-2-(6-chloro-3-pyridyl)-2-hydroxyethyl][2-(4-hydroxyphenyl)ethyl]carbamate MS (m/z): 393 (M+H)

Preparation 30

Under nitrogen at −60° C., to a solution of tert-butyl [2-(4-hydroxyphenyl)ethl][(2R)-2-hydroxy-2-(3-pyridyl)-ethyl]carbamate (570 mg) and 2,6-lutidine (0.22 ml) in dichloromethane (10 ml) was added trifluoromethanesulfonic anhydride (0.28 ml), and the mixture was stirred at the same temperature for 1 hour. The resulting mixture was poured into aqueous ammonia and the aqueous mixture was extracted with ethyl acetate. The organic layer was washed successively with 1N hydrochloric acid, water, saturated aqueous sodium bicarbonate and brine, dried over anhydrous magnesium sulfate and evaporated under reduced pressure. The residue was purified by column chromatography on silica gel (hexane/ethyl acetate=1:1) to give 4-[2-[(tert-butoxycarbonyl)[(2R)-2-hydroxy-2-(3-pyridyl) ethyl]amino]-ethyl]phenyl trifluoromethanesulfonate (640 mg) as a colorless foam.

MS (m/z): 491 (M+H)

Preparation 31

The following compound was obtained according to a similar manner to that of Preparation 30.

4-[2-[(tert-Butoxycarbonyl) [(2R)-2-hydroxy-2-(3-chlorophenyl) ethyl]amino]propyl]phenyl trifluoromethanesulfonate MS (m/z): 538 (M+H)

Preparation 32

To a solution of 2,2,2-trifluoro-N-[(1R)-1-methyl-2-phenylethyl]acetamide (3.75 g) in acetic acid (32 ml)—water (6.5 ml)—sulfuric acid (0.97 ml) were added iodine (1.65 g) and periodic acid dihydrate (740 mg) at room temperature, and the mixture was heated to 60-80° C. for 5 hours. After being allowed to cool to room temperature, the mixture was partitioned between hexane/ethyl acetate and water. The organic layer was separated, washed successively with water, sodium sulfite solution, water and brine, dried over magnesium sulfate, and filtered. The filtrate was concentrated and the residue was recrystallized from diisopropyl ether (44 ml) to give 2,2,2-trifluoro-N-[(1R)-2-(4-iodophenyl)-1-methylethyl]acetamide (2.15 g) as a colorless needle.

NMR (CDCl$_3$, δ): 1.21 (3H, d, J=7 Hz), 2.74 (1H, dd, J=14, 7 Hz), 2.85 (1H, dd, J=14, 6 Hz), 4.26 (1H, m), 6.04 (1H, br s), 6.92 (2H, d, J=8 Hz), 7.65 (2H, d, J=8 Hz) (+)ESI-MS (m/z): 380 (M+Na)$^+$

Preparation 33

The following compound was obtained according to a similar manner to that of Preparation 32.

2,2,2-Trifluoro-N-[3-(4-iodophenyl)propyl]acetamide

NMR (CDCl$_3$, δ): 1.90 (2H, quintet, J=7 Hz), 2.62 (2H, t, J=7 Hz), 3.38 (2H, q, J=7 Hz), 6.26 (1H, br s), 6.93 (2H, d, J=8 Hz), 7.62 (2H, d, J=8 Hz) (+)ESI-MS (m/z): 380 (M+Na)$^+$ Preparation 34

To a mixture of 3-(4-hydroxyphenyl)propanoic acid (15.0 g), (1R)-2-amino-1-(3-chlorophenyl)ethanol hydrochloride (18.8 g), and 1-hydroxybenzotriazole (14.6 g) in N,N-dimethylformamide (100 ml) was added 1-(3-dimethylaminopropyl)-3-ethylcarbodiimide hydrochloride (26.0 g), and the mixture was stirred at room temperature for 3 hours. The mixture was partitioned between ethyl acetate and water. The organic layer was separated, washed successively with sodium bicarbonate solution and brine, dried over magnesium sulfate, and filtered. The filtrate was concentrated and the residue was purified by column chromatography (silica gel, hexane/ethyl acetate) to give N-[(2R)-2-(3-chlorophenyl)-2-hydroxyethyl]-3-(4-hydroxyphenyl)propanamide (11.61 g) as a white amorphous powder.

MS (m/z): 320 (M+H)

Preparation 35

To a solution of N-[(2R)-2-(3-chlorophenyl)-2-hydroxyethyl]-3-(4-hydroxyphenyl)propanamide (11.61 g) in tetrahydrofuran (70 ml) was added borane-methyl sulfide complex (10M, 11.9 ml) at 0° C., and the mixture was heated to 80° C. for 1 hour. After being allowed to cool to room temperature, the mixture was added 2N hydrochloric acid (20 ml) at 0° C. The mixture was heated to 80° C. for 1 hour. After being allowed to cool to room temperature, the mixture was added 1N sodium hydroxide (40 ml) and di-tert-butyl dicarbonate (8.72 g) and stirred for 1 hour at room temperature. The mixture was partitioned between hexane/ethyl acetate and water. The organic layer was separated, washed successively with water, sodium sulfite solution, water and brine, dried over magnesium sulfate, and filtered. The filtrate was concentrated and the residue was purified by column chromatography (silica gel, hexane/ethyl acetate) to give tert-butyl [(2R)-2-(3-chlorophenyl)-2-hydroxyethyl][3-(4-hydroxyphenyl)propyl]carbamate (11.36 g) as a white powder.

MS (m/z): 406 (M+H)

Preparation 36

A mixture of methyl 4'-[2-[[(benzyloxy)carbonyl]-amino]ethyl]-2-methyl-1,1'-biphenyl-4-carboxylate (650 mg), ammonium formate (500 mg) and palladium on carbon powder (400 mg) in methanol (10 ml) and water (1.0 ml) was refluxed for 2 hours. The reaction mixture was filtrated and poured into water and extracted with chloroform. The organic layer was washed with brine, dried over magnesium sulfate and evaporated to give methyl 4'-(2-aminoethyl)-2-methyl-1,1'-biphenyl-4-carboxylate (380 mg).

(+)ESI-MS (m/z): 270 (M+H)$^+$

Preparation 37

The following compounds were obtained according to a similar manner to that of Preparation 36.
(1) Ethyl 4'-(2-aminoethyl)-2-methoxy-1,1'-biphenyl-4-carboxylate
MS (m/z): 300 (M+H)
(2) tert-Butyl [2-(4-hydroxyphenyl)ethyl][(2R)-2-hydroxy-2-(3-pyridyl)ethyl]carbamtate
MS (m/z): 359 (M+H)

Preparation 38

The following compound was obtained according to a similar manner to that of Example 14.
tert-Butyl [(2R)-2-(3-chlorophenyl)-2-hydroxyethyl][2-(4'-formyl-2',3'-dimethyl-1,1'-biphenyl-4-yl)ethyl]carbamate (+)ESI-MS (m/z): 530 (M+Na)$^+$

EXAMPLE 14

To a solution of tert-butyl [2-(4-bromophenyl)ethyl]-[(2R)-2-(3-chlorophenyl)-2-hydroxyethyl]carbamate (365 mg) in 1,2-dimethoxyethane (6 ml) was added [4-(ethoxycarbonyl)-2-methoxyphenyl]boronic acid (216 mg), tetrakis(triphenylphosphine)palladium (46 mg) and aqueous solution of sodium carbonate (2M, 0.85 ml), and the mixture was stirred at 80° C. for 4 hours under nitrogen. The mixture was diluted with ethyl acetate and water. The organic layer was separated, washed with brine, dried over magnesium sulfate and evaporated under reduced pressure. The residue was purified by column chromatography on silica gel (hexane/ethyl acetate=2/1) to give ethyl 4'-[2-[(tert-butoxycarbonyl)[(2R)-2-(3-chlorophenyl)-2-hydroxyethyl]-amino]ethyl]-2-methoxy-1,1'-biphenyl-4-carboxylate (222 mg).

MS (m/z): 554 (M+H)$^+$

EXAMPLE 15

The following compounds were obtained according to a similar manner to that of Example 14.
(1) 4'-[(2R)-2-[[(2R)-2-(3-Chlorophenyl)-2-hydroxyethyl]amino]propyl]-3-methoxy-1,1'-biphenyl-4-carboxylic acid hydrochloride
NMR (DMSO-d$_6$, δ): 1.14 (3H, d, J=6.4 Hz), 2.8-3.8 (5H, m), 3.92 (3H, s), 5.0-5.3 (1H, m), 6.3-6.4 (1H, m), 7.2-7.8 (10H, m), 8.13 (1H, br s), 8.85 (1H, br s), 9.42 (1H, br s) MS (m/z): 440 (M+H)
(2) 4'-[(2R)-2-[[(2R)-2-(3-Chlorophenyl)-2-hydroxyethyl]amino]propyl]-2-methoxy-1,1'-biphenyl-4-carboxylic acid hydrochloride
NMR (DMSO-d$_6$, δ): 1.17 (3H, d, J=6.4 Hz), 2.8-3.8 (5H, m), 3.83 (3H, s), 5.0-5.2 (1H, m), 6.3-6.4 (1H, m), 7.2-7.8 (10H, m), 8.11 (1H, br s), 8.86 (1H, br s), 9.37 (1H, br s) MS (m/z): 440 (M+H)
(3) 4'-[(2R)-2-[[(2R)-2-(3-Chlorophenyl)-2-hydroxyethyl]amino]propyl]-2-methyl-1,1'-biphenyl-4-carboxylic acid hydrochloride
NMR (DMSO-d$_6$, δ): 1.17 (3H, d, J=6.4 Hz), 2.28 (3H, s), 2.8-3.8 (5H, m), 5.0-5.3 (1H, m), 6.3-6.4 (1H, m), 7.2-7.6 (8H, m), 7.7-7.9 (2H, m), 8.11 (1H, br s), 8.86 (1H, br s), 9.39 (1H, br s) MS (m/z): 424 (M+H)
(4) 4'-[(2R)-2-[[(2S)-2-(3-Chlorophenyl)-2-hydroxyethyl]amino]propyl]-3-methoxy-1,1'-biphenyl-4-carboxylic acid hydrochloride
NMR (DMSO-d$_6$, δ): 1.16 (3H, d, J=6.4 Hz), 2.8-3.8 (5H, m), 3.91 (3H, s), 5.0-5.3 (1H, m), 6.3-6.4 (1H, m), 7.2-7.8 (11H, m), 8.77 (1H, br s), 9.13 (1H, br s) MS (m/z): 440 (M+H)
(5) 4'-[(2R)-2-[[(2R)-2-Phenyl-2-hydroxyethyl]amino]-propyl]-3-methoxy-1,1'-biphenyl-4-carboxylic acid hydrochloride
NMR (DMSO-d$_6$, δ): 1.15 (3H, d, J=6.4 Hz), 2.8-3.8 (5H, m), 3.92 (3H, s), 5.0-5.2 (1H, m), 6.3-6.4 (1H, m), 7.2-7.6 (9H, m), 7.7-7.9 (3H, m), 8.81 (1H, br s), 9.31 (1H, br s) MS (m/z): 406 (M+H)
(6) 4'-[(2R)-2-[[(2R)-2-Phenyl-2-hydroxyethyl]amino]-propyl]-2-methyl-1,1'-biphenyl-4-carboxylic acid hydrochloride
NMR (DMSO-d$_6$, δ): 1.17 (3H, d, J=6.4 Hz), 2.28 (3H, s), 2.8-3.8 (5H, m), 5.0-5.2 (1H, m), 6.3-6.4 (1H, m), 7.2-7.6 (9H, m), 7.7-7.9 (3H, m), 8.81 (1H, br s), 9.24 (1H, br s) MS (m/z): 390 (M+H)
(7) 4'-[(2R)-2-[[(2S)-2-Phenyl-2-hydroxyethyl]amino]-propyl]-2-methyl-1,1'-biphenyl-4-carboxylic acid hydrochloride
NMR (DMSO-d$_6$, δ): 1.19 (3H, d, J=6.4 Hz), 2.27 (3H, s), 2.8-3.8 (5H, m), 5.0-5.2 (1H, m), 6.2-6.3 (1H, m), 7.2-7.6 (9H, m), 7.7-7.9 (3H, m), 8.80 (1H, br s), 9.35 (1H, br s) MS (m/z): 390 (M+H)
(8) 4'-[(2R)-2-[[(2R)-2-(3-Chlorophenyl)-2-hydroxyethyl]amino]propyl]-3-isopropyloxy-1,1'-biphenyl-4-carboxylic acid hydrochloride
NMR (DMSO-d$_6$, δ): 1.14 (3H, d, J=6.4 Hz), 1.30 (6H, d, J=5.8 Hz), 2.8-3.8 (5H, m), 4.6-4.9 (1H, m), 5.0-5.3 (1H, m), 6.2-6.4 (1H, m), 7.2-7.8 (11H, m), 8.82 (1H, br s), 9.24 (1H, br s) MS (m/z): 468 (M+H)
(9) 4'-[(2R)-2-[[(2R)-2-Phenyl-2-hydroxyethyl]amino]-propyl]-3-isopropyloxy-1,1'-biphenyl-4-carboxylic acid hydrochloride
NMR (DMSO-d$_6$, δ): 1.12 (3H, d, J=6.4 Hz), 1.30 (6H, d, J=5.8 Hz), 2.8-3.8 (5H, m), 4.6-4.9 (1H, m), 5.0-5.3 (1H, m), 6.2-6.4 (1H, m), 7.2-7.8 (12H, m), 8.82 (1H, br s) MS (m/z): 434 (M+H)
(10) 4'-[(2R)-2-[[(2R)-2-(3-Chlorophenyl)-2-hydroxyethyl]amino]propyl]-3-cyclohexyloxy-1,1'-biphenyl-4-carboxylic acid hydrochloride
NMR (DMSO-d$_6$, δ): 1.14 (3H, d, J=6.4 Hz), 1.2-2.0 (10H, m), 2.8-3.8 (5H, m), 4.65 (1H, m), 5.0-5.2 (1H, m), 6.3-6.4 (1H, m), 7.2-7.9 (11H, m), 8.79 (1H, br s), 9.10 (1H, br s) MS (m/z): 508 (M+H)
(11) 4'-[(2R)-2-[[(2R)-2-Phenyl-2-hydroxyethyl]amino)-propyl]-3-cyclohexyloxy-1,1'-biphenyl-4-carboxylic acid hydrochloride NMR (DMSO-d$_6$, δ): 1.14 (3H, d, J=6.4 Hz), 1.2-2.0 (10H, m), 2.8-3.8 (5H, m), 4.65 (1H, m), 4.9-5.1 (1H, m), 6.23 (1H, m), 7.1-7.9 (12H, m) MS (m/z): 474 (M+H)

(12) Methyl 4'-[2-[(tert-butoxycarbonyl)[(2R)-2-(3-chlorophenyl)-2-hydroxyethyl]amino]ethyl]-3-methoxy-1,1'-biphenyl-4-carboxylate (+)ESI-MS (m/z): 562 (M+Na)$^+$

(13) Methyl 4'-[2-[(tert-butoxycarbonyl)[(2R)-2-(3-chlorophenyl)-2-hydroxyethyl]amino]ethyl]-2-chloro-1,1'-biphenyl-4-carboxylate (+)ESI-MS (m/z): 544 (M+H)$^+$

EXAMPLE 16

To a solution of 4-[2-[(tert-butoxycarbonyl)[(2R)-2-(3-chlorophenyl)-2-hydroxyethyl]amino]ethyl]phenyl trifluoromethanesulfonate (300 mg) in 1,2-dimethoxyethane (5 ml) was added [3-fluoro-4-(methoxycarbonyl)phenyl]boronic acid (125 mg), tetrakis(triphenylphosphine)palladium (53 mg) and aqueous solution of sodium carbonate (2M, 0.6 ml), and the mixture was stirred at 80° C. for 2 hours under nitrogen. The mixture was diluted with ethyl acetate and water. The organic layer was separated, washed with brine, dried over magnesium sulfate and evaporated under reduced pressure. The residue was purified by column chromatography on silica gel (hexane/ethyl acetate=3/1) to give methyl 4'-[2-[(tert-butoxycarbonyl)[(2R)-2-(3-chlorophenyl)-2-hydroxyethyl]amino]ethyl]-3-fluoro-1,1'-biphenyl-4-carboxylate (230 mg).

(+)ESI-MS (m/z): 528 (M+H)$^+$

EXAMPLE 17

The following compound was obtained according to a similar manner to that of Example 16.

Methyl 4'-[2-[(tert-butoxycarbonyl)[(2R)-2-(3-chlorophenyl)-2-hydroxyethyl]amino]ethyl]-3-methyl-1,1'-biphenyl-4-carboxylate (+)ESI-MS (m/z): 546 (M+Na)$^+$

EXAMPLE 18

To a solution of ethyl 4'-[2-[(tert-butoxycarbonyl)-[(2R)-2-(3-chlorophenyl)-2-hydroxyethyl]amino]ethyl]-2-methoxy-1,1'-biphenyl-4-carboxylate (220 mg) in ethanol (2.0 ml) was added 1N aqueous sodium hydroxide solution (1.2 ml), and the mixture was stirred at 40° C. for 3 hours. The solvent was removed by evaporation, and the aqueous solution was acidified with 1N hydrochloric acid and extracted with ethyl acetate (30 ml×2). The combined organic layers were washed with water and brine, dried over magnesium sulfate and evaporated under reduced pressure to give a benzoic acid product. To a solution of the product in tetrahydrofuran (1.5 ml) was added 4N hydrochloride in dioxane (1.0 ml), and the mixture was stirred at room temperature for 12 hours. The resultant solid was collected by filtration and dried to give 4'-[2-[[(2R)-2-(3-chlorophenyl)-2-hydroxyethyl]amino]-ethyl]-2-methoxy-1,1'-biphenyl-4-carboxylic acid hydrochloride (83 mg).

NMR (DMSO-d$_6$, δ): 3.02-3.27 (6H, m), 3.82 (3H, s), 4.98-5.02 (1H, m), 6.35 (1H, br), 7.30-7.64 (11H, m), 9.05 (1H, br) (−)ESI-MS (m/z): 424 (M−HCl−H)$^-$

EXAMPLE 19

The following compounds were obtained according to a similar manner to that of Example 18.

(1) 4'-[2-[[(2R)-2-(3-Chlorophenyl)-2-hydroxyethyl]amino]-ethyl]-3-methoxy-1,1'-biphenyl-4-carboxylic acid hydrochloride NMR (DMSO-d$_6$, δ): 3.01-3.34 (6H, m), 3.92 (3H, s), 5.02-5.06 (1H, m), 6.37 (1H, br), 7.26-7.48 (9H, m), 7.74 (2H, d, J=7.9 Hz), 9.25 (1H, br) (−)ESI-MS (m/z): 424 (M−HCl−H)$^-$ (2) 2-Chloro-4'-[2-[[(2R)-2-(3-chlorophenyl)-2-hydroxyethyl]amino]ethyl]-1,1'-biphenyl-4-carboxylic acid hydrochloride NMR (DMSO-d$_6$, δ): 3.01-3.34 (6H, m), 4.99-5.03 (1H, m), 6.36 (1H, br), 7.37-7.55 (9H, m), 7.93-8.03 (2H, m), 9.10 (1H, br) (−)ESI-MS (m/z): 424 (M−HCl−H)$^-$ (3) 4'-[2-[[(2R)-2-(3-Chlorophenyl)-2-hydroxyethyl]amino]-ethyl]-3-fluoro-1,1'-biphenyl-4-carboxylic acid hydrochloride NMR (DMSO-d$_6$, δ): 3.01-3.33 (6H, m), 4.98-5.03 (1H, m), 6.34 (1H, br), 7.35-7.47 (6H, m), 7.61-7.98 (5H, m), 9.10 (1H, br) (−)ESI-MS (m/z): 412 (M−HCl−H)$^-$ (4) 4'-[2-[[(2R)-2-(3-Chlorophenyl)-2-hydroxyethyl]amino]-ethyl]-3-methyl-1,1'-biphenyl-4-carboxylic acid hydrochloride NMR (DMSO-d$_6$, δ): 2.60 (3H, s), 3.01-3.34 (6H, m), 4.98-5.02 (1H, m), 6.34 (1H, br), 7.36-7.60 (8H, m), 7.72 (2H, d, J=8.0 Hz), 7.91 (1H, d, J=8.0 Hz), 9.25 (1H, br) (−)ESI-MS (m/z): 408 (M−HCl−H)$^-$

EXAMPLE 20

To a solution of tert-butyl [(2R)-2-(3-chlorophenyl)-2-hydroxyethyl][2-(4'-formyl-2',3'-dimethyl-1,1'-biphenyl-4-yl)ethyl]carbamate in acetonitrile (2.5 ml) and pH 4 buffer solution (sodium dihydrogenphosphate) (1.3 ml) was added 30% hydrogen peroxide solution (60 μl) and 80% sodium chlorite (128 mg) below 10° C. The reaction mixture was stirred at 40° C. for 1.5 hours. The mixture was diluted with ethyl acetate, washed with water and brine, dried over magnesium sulfate and evaporated under reduced pressure to give a benzoic acid product. To a solution of the product in tetrahydrofuran (1.0 ml) was added 4N hydrochloride in dioxane (1.18 ml), and the mixture was stirred at room temperature for 12 hours. The resultant solid was collected by filtration and dried to give 4'-[2-[[(2R)-2-(3-chlorophenyl)-2-hydroxyethyl]amino]ethyl]-2,3-dimethyl-1,1'-biphenyl-4-carboxylic acid hydrochloride (140 mg).

NMR (DMSO-d$_6$, δ): 2.14 (3H, s), 2.45 (3H, s), 3.00-3.34 (6H, m), 4.99-5.03 (1H, m), 6.34 (1H, br), 7.07 (1H, d, J=8.0 Hz), 7.05-7.59 (9H, m), 9.25 (1H, br) (−)ESI-MS (m/z): 422 (M−HCl−H)$^-$

EXAMPLE 21

A solution of ethyl 4'-(3-aminopropyl)-1,1'-biphenyl-4-carboxylate (200 mg), and 2-chloro-5-[(2R)-2-oxiranyl]-pyridine (71.5 mg) in ethanol (10 ml) was refluxed for 18 hours. The mixture was evaporated in vacuo. The residue was purified by column chromatography on silica gel (chloroform:methanol=100:1) to give ethyl 4'-[3-[[(2R)-2-(6-chloro-3-pyridyl)-2-hydroxyethyl]amino]propyl]-1,1'-biphenyl-4-caroxylate (96 mg) as a colorless foam.

MS (m/z): 439 (M+H)

EXAMPLE 22

The following compounds were obtained according to a similar manner to that of Example 21.

(1) Methyl 4'-[2-[[(2R)-2-(6-chloro-3-pyridyl)-2-hydroxyethyl]amino]ethyl]-2-methyl-1,1'-biphenyl-4-carboxylate
(+)ESI-MS (m/z): 425 (M+H)⁺

(2) Ethyl 4'-[2-[[(2R)-2-(6-chloro-3-pyridyl)-2-hydroxyethyl]amino]ethyl]-2-methoxy-1,1'-biphenyl-4-carboxylate
MS (m/z): 454 (M⁺)

EXAMPLE 23

To a solution of ethyl 4'-[3-[[(2R)-2-(6-chloro-3-pyridyl)-2-hydroxyethyl]amino]propyl]-1,1'-biphenyl-4-carboxylate (96 mg) in tetrahydrofuran (3.5 ml) was added di-tert-butyl dicarbonate (53 mg), and the mixture was stirred at room temperature for 30 minutes and then evaporated. To the residue were added 1N sodium hydroxide solution (0.5 ml) and methanol (0.5 ml), and was stirred for 2 hours at room temperature. The residue was diluted with ethyl acetate and saturated aqueous sodium bicarbonate solution. The organic layer was separated, washed with brine, dried over magnesium sulfate and evaporated. The residue was purified by column chromatography on silica gel (hexane/ethyl acetate=1/1) to give 4'-[3-[(tert-butoxycarbonyl)[(2R)-2-(6-chloro-3-pyridyl)-2-hydroxyethyl]-amino]propyl]-1,1'-biphenyl-4-carboxylic acid (100 mg) as a colorless foam.
MS (m/z) 512 (M+H)

EXAMPLE 24

The following compounds were obtained according to a similar manner to that of Example 23.
(1) 4'-[2-[(tert-Butoxycarbonyl)[(2R)-2-(6-chloro-3-pyridyl)-2-hydroxyethyl]amino]ethyl]-2-methyl-1,1'-biphenyl-4-carboxylic acid
(+)ESI-MS (m/z): 509 (M−H)⁻

(2) 4'-[2-[(tert-Butoxycarbonyl)[(2R)-2-(6-chloro-3-pyridyl)-2-hydroxyethyl]amino]ethyl]-2-methoxy-1,1'-biphenyl-4-carboxylic acid
MS (m/z): 527 (M+H)

EXAMPLE 25

4'-[3-[(tert-Butoxycarbonyl)[(2R)-2-(6-chloro-3-pyridyl)-2-hydroxyethyl]amino]propyl]-1,1'-biphenyl-4-carboxylic acid (100 mg), ammonium formate (50 mg) and palladium on carbon powder (30 mg) in methanol (5 ml) and water (1.0 ml) was refluxed for 30 minutes. The reaction mixture was filtrated and poured into water and extracted with ethyl acetate. The organic layer was washed with brine, dried over magnesium sulfate, and evaporated in vacuo. A mixture of the residue was chromatographed (chloroform-methanol) over silica gel to give 4'-[3-[(tert-butoxycarbonyl)[(2R)-2-hydroxy-2-(3-pyridyl)ethyl]amino]-propyl]-1,1'-biphenyl-4-carboxylic acid (90 mg) as a colorless foam.
MS (m/z): 477 (M+H)

EXAMPLE 26

The following compounds were obtained according to a similar manner to that of Example 25.
(1) 4'-[2-[(tert-Butoxycarbonyl)[(2R)-2-hydroxy-2-(3-pyridyl)ethyl]amino]ethyl]-2-methyl-1,1'-biphenyl-4-carboxylic acid
(+)ESI-MS (m/z): 475 (M−H)⁻

(2) 4'-[2-[(tert-Butoxycarbonyl)[(2R)-2-hydroxy-2-(3-pyridyl)ethyl]amino]ethyl]-2-methoxy-1,1'-biphenyl-4-carboxylic acid
MS (m/z): 493 (M+H)

(3) 4'-[3-[(tert-Butoxycarbonyl)[(2R)-2-hydroxy-2-(3-pyridyl)ethyl]amino]propyl]-2-methoxy-1,1'-biphenyl-4-carboxylic acid
MS (m/z): 507 (M+H)

(4) 4'-[(2R)-2-[(tert-Butoxycarbonyl)[(2R)-2-hydroxy-2-(3-pyridyl)ethyl]amino]propyl]-1,1'-biphenyl-4-carboxylic acid
MS (m/z): 477 (M+H)

EXAMPLE 27

A solution of tert-butyl 4'-[3-[(tert-butoxycarbonyl)-[(2R)-2-hydroxy-2-(3-pyridyl)ethyl]amino]propyl]-1,1'-biphenyl-4-carboxylic acid (90 mg) and 4N hydrochloride in dioxane (5.0 ml) was stirred at room temperature for 24 hours. The resultant solid was collected by filtration and dried to give 4'-[3-[[(2R)-2-hydroxy-2-(3-pyridyl)ethyl]-amino]propyl]-1,1'-biphenyl-4-carboxylic acid dihydrochloride (80 mg) as a white solid.
NMR (DMSO-$d_6$, δ): 2.90-3.90 (8H, m), 5.10-5.20 (1H, m), 7.35 (1H, d, J=8 Hz), 7.65-7.85 (6H, m), 8.05 (1H, d, J=8 Hz), 8.25 (1H, d, J=8 Hz), 8.70-8.85 (2H, m) MS (m/z): 377 (M+H)

EXAMPLE 28

The following compounds were obtained according to a similar manner to that of Example 27.
(1) 4'-[2-[[(2R)-2-Hydroxy-2-(3-pyridyl)ethyl]amino]ethyl]-2-methyl-1,1'-biphenyl-4-carboxylic acid dihydrochloride
NMR (DMSO-$d_6$, δ): 3.10-3.80 (6H, m), 3.90 (3H, s), 5.10-5.20 (1H, m), 7.40-7.70 (7H, m), 7.8-7.90 (1H, m), 8.25 (1H, d, J=8 Hz), 8.70-8.85 (2H, m) (−)ESI-MS (m/z): 375 (M−2HCl−H)⁻

(2) 4'-[2-([(2R)-2-Hydroxy-2-(3-pyridyl)ethyl]amino]ethyl]-2-methoxy-1,1'-biphenyl-4-carboxylic acid dihydrochloride
NMR (DMSO-$d_6$, δ): 3.10-3.80 (6H, m), 3.90 (3H, s), 5.10-5.20 (1H, m), 7.40-7.70 (7H, m), 7.80-7.90 (1H, m), 8.25 (1H, d, J=8 Hz), 8.70-8.85 (2H, m) MS (m/z): 393 (M+H)

(3) 4'-[3-[[(2R)-2-Hydroxy-2-(3-pyridyl)ethyl]amino]-propyl]-2-methoxy-1,1'-biphenyl-4-carboxylic acid dihydrochloride
NMR (DMSO-$d_6$, δ): 2.90-3.90 (8H, m), 3.95 (3H, s), 5.10-5.20 (1H, m), 7.35 (1H, d, J=8 Hz), 7.65-7.85 (6H, m), 8.05 (1H, d, J=8 Hz), 8.25 (1H, d, J=8 Hz), 8.70-8.85 (2H, m) MS (m/z): 407 (M+H)

(4) 2-Chloro-4'-[2-[[(2R)-2-hydroxy-2-(3-pyridyl)ethyl]-amino]ethyl]-1,1'-biphenyl-4-carboxylic acid dihydrochloride
NMR (DMSO-$d_6$, δ): 3.10-3.80 (6H, m), 5.10-5.20 (1H, m), 7.40-7.70 (7H, m), 7.90-8.10 (2H, m), 8.70-8.85 (2H, m) MS (m/z): 397 (M+H)

(5) 4'-[(2R)-2-[[(2R)-2-Hydroxy-2-(3-pyridyl)ethyl]amino]-propyl]-1,1'-biphenyl-4-carboxylic acid dihydrochloride
NMR (DMSO-$d_6$, δ): 1.70 (3H, d, J=6 Hz), 3.30-3.90 (6H, m), 5.10-5.20 (1H, m), 7.40-7.70 (7H, m), 7.80-7.90 (1H, m), 8.25 (1H, d, J=8 Hz), 8.70-8.85 (2H, m) MS (m/z): 377 (M+H)

(6) 4'-[3-[[(2R)-2-(3-Chlorophenyl)-2-hydroxyethyl] amino]-propyl]-2-methyl-1,1'-biphenyl-4-carboxylic acid hydrochloride NMR (DMSO-d$_6$, δ): 2.00-2.15 (2H, m), 2.30 (3H, s), 2.60-3.30 (6H, m), 5.00-5.10 (1H, m), 7.20-7.60 (9H, m), 7.75-7.90 (2H, m) MS (m/z): 424 (M+H)

EXAMPLE 29

The following compounds were obtained according to a similar manner to that of Example 23.
(1) Ethyl 4'-[3-[(tert-butoxycarbonyl)[(2R)-2-(6-chloro-3-pyridyl)-2-hydroxyethyl]amino]propyl]-2-methoxy-1,1'-biphenyl-4-carboxylate
MS (m/z): 569 (M+H)
(2) Methyl 4'-[2-[(tert-butoxycarbonyl)[(2R)-2-hydroxy-2-(3-pyridyl)ethyl]amino]ethyl]-2-chloro-1,1'-biphenyl-4-carboxylate
MS (m/z): 512 (M+H)
(3) Methy 4'-[(2R)-2-[(tert-butoxycarbonyl)[(2R)-2-(6-chloro-3-pyridyl)-2-hydroxyethyl]amino]propyl]-1,1'-biphenyl-4-carboxylate
MS (m/z): 524 (M+H)
(4) Methyl 4'-[3-[(tert-butoxycarbonyl)[(2R)-2-(3-chlorophenyl)-2-hydroxyethyl]amino]propyl]-2-methyl-1,1'-biphenyl-4-carboxylate
MS (m/z): 538 (M+H)
(5) 4'-[(2R)-2-[[(2R)-2-Hydroxy-2-(3-pyridyl)ethyl]amino]-propyl]-3-methoxy-1,1'-biphenyl-4-carboxylic acid dihydrochloride
NMR (DMSO-d$_6$, δ): 1.14 (3H, d, J=6.4 Hz), 2.8-3.8 (5H, m), 3.92 (3H, s), 5.1-5.3 (1H, m), 7.2-7.5 (4H, m), 7.7-7.9 (4H, m), 8.2-8.4 (1H, m), 8.8-9.0 (2H, m), 9.36 (1H, br s) MS (m/z): 407 (M+H)
(6) 4'-[(2R)-2-[[(2R)-2-Hydroxy-2-(3-pyridyl)ethyl]amino]-propyl]-2-methoxy-1,1'-biphenyl-4-carboxylic acid dihydrochloride
NMR (DMSO-d$_6$, δ): 1.14 (3H, d, J=6.4 Hz), 2.8-3.8 (5H, m), 3.83 (3H, s), 5.1-5.3 (1H, m), 7.2-7.8 (7H, m), 7.8-8.0 (1H, m), 8.2-8.5 (1H, m), 8.7-9.0 (2H, m), 9.02 (1H, br s), 9.36 (1H, br s) MS (m/z): 407 (M+H)
(7) 4'-[(2R)-2-[[(2R)-2-Hydroxy-2-(3-pyridyl)ethyl]amino]-propyl]-2-methyl-1,1'-biphenyl-4-carboxylic acid dihydrochloride
NMR (DMSO-d$_6$, δ): 1.19 (3H, d, J=6.4 Hz), 2.48 (3H, s), 2.8-3.8 (5H, m), 5.1-5.3 (1H, m), 7.2-7.5 (5H, m), 7.8-8.0 (3H, m), 8.37 (1H, d, J=8.2 Hz), 8.78 (1H, d, J=4.6 Hz), 8.87 (1H, s), 9.04 (1H, br s), 9.35 (1H, br s) MS (m/z): 391 (M+H)
(8) 4'-[(2R)-2-[[(2R)-2-Hydroxy-2-(3-pyridyl)ethyl]amino]-propyl]-3-methyl-1,1'-biphenyl-4-carboxylic acid dihydrochloride
NMR (DMSO-d$_6$, δ): 1.19 (3H, d, J=6.4 Hz), 2.60 (3H, s), 2.8-3.8 (5H, m), 5.1-5.3 (1H, m), 7.2-8.0 (8H, m), 8.37 (1H, d, J=8.2 Hz), 8.79 (1H, d, J=4.6 Hz), 8.87 (1H, s), 9.05 (1H, br s), 9.35 (1H, br s) MS (m/z): 391 (M+H)
(9) 4'-[(2R)-2-[[(2R)-2-Hydroxy-2-(3-pyridyl)ethyl]amino]-propyl]-3-isopropyloxy-1,1'-biphenyl-4-carboxylic acid dihydrochloride
NMR (DMSO-d$_6$, δ): 1.19 (3H, d, J=6.4 Hz), 1.31 (6H, d, J=6.0 Hz), 2.8-3.8 (5H, m), 4.6-4.9 (1H, m), 5.1-5.3 (1H, m), 7.2-7.5 (4H, m), 7.6-8.0 (4H, m), 8.37 (1H, d, J=8.2 Hz), 8.80 (1H, d, J=4.6 Hz), 8.88 (1H, s), 9.02 (1H, br s), 9.35 (1H, br s) MS (m/z): 435 (M+H)
(10) 4'-[(2R)-2-[[(2S)-2-Hydroxy-2-(3-pyridyl)ethyl]amino]-propyl]-1,1'-biphenyl-4-carboxylic acid dihydrochloride
NMR (DMSO-d$_6$, δ): 1.19 (3H, d, J=6.4 Hz), 2.8-3.8 (5H, m), 5.1-5.3 (1H, m), 7.2-8.1 (8H, m), 8.57 (1H, d, J=7.8 Hz), 8.81 (1H, d, J=4.6 Hz), 8.90 (1H, s), 9.10 (1H, br s), 9.56 (1H, br s) MS (m/z): 357 (M−H)
(11) 4'-[(2R)-2-[[(2S)-2-Hydroxy-2-(6-chloro-3-pyridyl)-ethyl]amino]propyl]-1,1'-biphenyl-4-carboxylic acid dihydrochloride
NMR (DMSO-d$_6$, δ): 1.17 (3H, d, J=6.4 Hz), 2.8-3.8 (5H, m), 5.1-5.3 (1H, m), 7.39 (2H, d, J=8.0 Hz), 7.58 (1H, d, J=8.0 Hz), 7.6-8.2 (7H, m), 8.48 (1H, d, J=2.4 Hz), 8.86 (1H, br s), 9.22 (1H, br s) MS (m/z): 409 (M−H)
(12) 4'-[(2R)-2-[[(2R)-2-Hydroxy-2-(6-chloro-3-pyridyl)-ethyl]amino]propyl]-1,1'-biphenyl-4-carboxylic acid dihydrochloride
NMR (DMSO-d$_6$, δ): 1.16 (3H, d, J=6.4 Hz), 2.8-3.8 (5H, m), 5.1-5.3 (1H, m), 7.38 (2H, d, J=8.0 Hz), 7.58 (1H, d, J=8.0 Hz), 7.6-8.2 (7H, m), 8.49 (1H, d, J=2.4 Hz), 8.86 (1H, br s), 9.45 (1H, br s) MS (m/z): 409 (M−H)
(13) 4'-[(2R)-2-[[(2R)-2-Hydroxy-2-(3-pyridyl)ethyl] amino]-propyl]-3-cyclohexyloxy-1,1'-biphenyl-4-carboxylic acid dihydrochloride
NMR (DMSO-d$_6$, δ): 1.15 (3H, d, J=6.4 Hz), 1.2-2.0 (10H, m), 2.7-3.8 (5H, m), 4.65 (1H, m), 5.31 (1H, m), 7.2-7.5 (5H, m), 7.6-7.8 (2H, m), 7.9-8.0 (1H, m), 8.45 (1H, m), 8.82 (1H, d, J=2.6 Hz), 8.90 (1H, s), 9.07 (1H, br s), 9.43 (1H, br s) MS (m/z): 475 (M+H)

EXAMPLE 30

To a solution of ethyl 4'-[3-[(tert-butoxycarbonyl)-[(2R)-2-(6-chloro-3-pyridyl)-2-hydroxyethyl]amino]propyl]-2-methoxy-1,1'-biphenyl-4-carboxylate in ethanol (5.0 ml) was added 1N sodium hydroxide (1.0 ml) and the mixture was stirred for 2 hours at room temperature. The mixture was diluted with ethyl acetate and 1N hydrochloric acid. The organic layer was separated, washed with brine, dried over magnesium sulfate and evaporated. The residue was purified by column chromatography on silica gel (hexane/ethyl acetate=1/1) to give 4'-[3-[(tert-butoxycarbonyl)[(2R)-2-(6-chloro-3-pyridyl)-2-hydroxyethyl]amino]propyl]-2-methoxy-1,1'-biphenyl-4-carboxylic acid (100 mg).
MS (m/z): 541 (M+H)

EXAMPLE 31

The following compounds were obtained according to a similar manner to that of Example 30.
(1) 4'-[2-[(tert-Butoxycarbonyl)[(2R)-2-hydroxy-2-(3-pyridyl)ethyl]amino]ethyl]-2-chloro-1,1'-biphenyl-4-carboxylic acid
MS (m/z): 497 (M+H)
(2) 4'-[(2R)-2-[(tert-Butoxycarbonyl)[(2R)-2-(6-chloro-3-pyridyl)-2-hydroxyethyl]amino]propyl]-1,1'-biphenyl-4-carboxylic acid
MS (m/z): 511 (M+H)
(3) 4'-[3-[(tert-Butoxycarbonyl)[(2R)-2-(3-chlorophenyl)-2-hydroxyethyl]amino]propyl]-1,1'-biphenyl-4-carboxylic acid
MS (m/z): 524 (M+H)

Preparation 39

The following compound was obtained according to a similar manner to that of Preparation 34.
N-[(2R)-2-(3-Chlorophenyl)-2-hydroxyethyl]-3-(3-hydroxyphenyl)propanamide
MS (m/z): 320 (M+H)

Preparation 40

The following compound was obtained according to a similar manner to that of Preparation 35.
tert-Butyl N-[(2R)-2-(3-chlorophenyl)-2-hydroxyethyl]-N-[3-(3-hydroxyphenyl)propyl]carbamate
MS (m/z): 405 (M+H)

Preparation 41

The following compounds were obtained according to a similar manner to that of Preparation 30.
(1) tert-Butyl N-[(2R)-2-(3-chlorophenyl)-2-hydroxyethyl]-N-[3-[3-[[(trifluoromethyl)sulfonyl]oxy]phenyl]propyl]-carbamate
MS (m/z) 537 (M+H)
(2) 4-[2-[N-(tert-Butoxycarbonyl)-N-[(2R)-2-(5-chloro-3-pyridyl)-2-hydroxyethyl]amino]ethyl]phenyl trifluoromethanesulfonate
MS (m/z): 525 (M+H)
(3) Methyl 4-[[(trifluoromethyl)sulfonyl]oxy]-1-naphthoate
MS (m/z): 358 (M+Na)
(4) Methyl [4-[[(trifluoromethyl)sulfonyl]oxy]phenyl]-acetate
NMR (DMSO-$d_6$, δ): 3.63(3H, s), 3.90(2H, s), 7.46(4H, s)
(5) Methyl [3-[[(trifluoromethyl)sulfonyl]oxy]phenyl]-acetate
NMR (DMSO-$d_6$, δ): 3.63(3H, s), 3.83(2H, s), 7.30-7.60 (4H, m)
(6) 5-Hydroxy-1-naphthyl trifluoromethanesulfonate
NMR (DMSO-$d_6$, δ): 6.80(2H, d, J=8 Hz), 7.20(2H, t, J=8 Hz), 7.50(2H, d, J=8 Hz)
(7) Ethyl 5-[[(trifluoromethyl)sulfonyl]oxy]-1-naphthoate
(8) 4-[2-[N-(tert-Butoxycarbonyl)-N-[(2R)-2-hydroxy-2-phenylethyl]amino]ethyl]phenyl trifluoromethane-sulfonate
MS (m/z): 490 (M+H)
(9) Methyl 4-(benzyloxy)-2-[[(trifluoromethyl)sulfonyl]oxy]benzoate
MS (m/z): 413 (M+Na)
(10) Methyl 5-[[(trifluoromethyl)sulfonyl]oxy]-1,1'-biphenyl-2-carboxylate
MS (m/z): 383 (M+Na)

Preparation 42

The following compounds were obtained according to a similar manner to that of Preparation 21.
(1) 4-[2-[[(2R)-2-(5,6-Dichloro-3-pyridyl)-2-hydroxyethyl]amino]ethyl]phenol
MS (m/z): 327 (M+H)
(2) 4-[2-[[(2R)-2-Hydroxy-2-phenylethyl]amino]ethyl]phenol
MS (m/z): 258 (M+H)

Preparation 43

To a solution of 4-[2-[[(2R)-2-(5,6-dichloro-3-pyridyl)-2-hydroxyethyl)amino]ethyl]phenol (850 mg) in acetic acid (15 ml) and water (1.0 ml) were added tetramethylammonium bromide (5.2 mg) and zinc dust (509 mg), and the mixture was stirred at 50° C. for 10 hours under nitrogen. The mixture was diluted with ethyl acetate and water. The organic layer was separated, washed with brine, dried over magnesium sulfate and evaporated. The residue was purified by column chromatography on silica gel (hexane/ethyl acetate=2/1) to give 4-[2-[[(2R)-2-(5-chloro-3-pyridyl)-2-hydroxyethyl]amino]ethyl] phenol (500 mg) as a colorless oil.
MS (m/z): 292 (M+H)

Preparation 44

The following compounds were obtained according to a similar manner to that of Preparation 26.
(1) tert-Butyl N-[(2R)-2-(5-chloro-3-pyridyl)-2-hydroxyethyl]-N-[2-(4-hydroxyphenyl)ethyl]carbamate
MS (m/z) 393 (M+H)
(2) tert-Butyl N-[(2R)-2-hydroxy-2-phenylethyl]-N-[2-(4-hydroxyphenyl)ethyl]carbamate
MS (m/z): 358 (M+H)

Preparation 45

To a solution of benzamide (1.42 g) in tetrahydrofuran (50 ml) were added sodium hydride (611 mg) and 4-bromobenzenesulfonyl chloride (3.0 g), and the mixture was stirred at room temperature for 3 hours. The mixture was diluted with ethyl acetate and water. The organic layer was separated, washed with brine, dried over magnesium sulfate and evaporated. The residue was purified by column chromatography on silica gel (hexane/ethyl acetate=2/1) to give N-benzoyl-4-bromobenzenesulfonamide (2.1 g) as a colorless powder.
NMR (CDCl$_3$, δ): 7.20-8.10(8H, m)

Preparation 46

The following compounds were obtained according to a similar manner to that of Preparation 12.
(1) 2-Phenoxy-4-(4,4,5,5-tetramethyl-1,3,2-dioxaborolan-2-yl)benzaldehyde
MS (m/z): 325 (M+H)
(2) N-Benzoyl-4-(4,4,5,5-tetramethyl-1,3,2-dioxaborolan-2-yl)benzenesulfonamide
MS (m/z): 386 (M−H)
(3) Methyl 2-isobutyl-4-(4,4,5,5-tetramethyl-1,3,2-dioxaborolan-2-yl)benzoate
MS (m/z): 319 (M+H)
(4) Methyl 2-isopropyl-4-(4,4,5,5-tetramethyl-1,3,2-dioxaborolan-2-yl)benzoate
MS (m/z): 327 (M+Na)
(5) Methyl 2-propyl-4-(4,4,5,5-tetramethyl-1,3,2-dioxaborolan-2-yl)benzoate
MS (m/z): 327 (M+Na)
(6) Benzyl (1R)-1-methyl-2-[4-(4,4,5,5-tetramethyl-1,3,2-dioxaborolan-2-yl)phenyl]ethylcarbamate
MS (m/z): 396 (M+H)

Preparation 47

The following compound was obtained according to a similar manner to that of Example 1.
4-Methoxy-1-naphthoic acid
NMR (DMSO-$d_6$, δ): 7.00(1H, d, J=6 Hz), 7.50-7.70(2H, m), 8.20-8.30(2H, m), 9.00(1H, d, J=8 Hz)

Preparation 48

Under nitrogen, 4-methoxy-1-naphthoic acid (4.33 g) in dichloromethane (45 ml) was added boron tribromide (1M in dichloromethane, 63 ml) dropwise at 0° C., and the mixture was stirred at the same temperature for 2 hours. The resulting mixture was poured into ice-cold water and the precipitate was collected by filtration. The filter cake was added to the mixture of water and ethyl acetate, and then adjusted to pH 9 with 1N sodium hydroxide. After separation, the organic layer was dried over anhydrous magnesium sulfate and evaporated in vacuo to afford 4-hydroxy-1-naphthoic acid (2.19 g) as a colorless powder.
MS (m/z): 187 (M−H)

Preparation 49

To a solution of 4-hydroxy-1-naphthoic acid (2.18 g) in methanol (15 ml) was added sulfuric acid (1.0 ml), and the mixture was stirred at 70° C. for 3 hours. The solution was diluted with water and ethyl acetate. The organic layer was separated and washed with brine. The extract was dried over magnesium sulfate, filtrated and concentrated under reduced pressure. The residue was purified by column chromatography on silica gel with ethyl acetate and hexane to give methyl 4-hydroxy-1-naphthoate (1.64 g) as a white solid.
MS (m/z): 239 (M+Na)

Preparation 50

The following compounds were obtained according to a similar manner to that of Preparation 16.

(1) Methyl 4-(4,4,5,5-tetramethyl-1,3,2-dioxaborolan-2-yl)-1-naphthoate
MS (m/z): 313 (M+H)

(2) Methyl [4-(4,4,5,5-tetramethyl-1,3,2-dioxaborolan-2-yl)phenyl]acetate
NMR (DMSO-$d_6$, δ): 1.66(12H, s), 3.60(3H, s), 3.70(2H, s), 7.20(2H, d, J=8 Hz), 7.60(2H, d, J=8 Hz)

(3) Methyl [3-(4,4,5,5-tetramethyl-1,3,2-dioxaborolan-2-yl)phenyl]acetate
NMR (DMSO-$d_6$, δ): 3.60(3H, s), 3.82(2H, s), 7.20-7.60 (6H, m)

(4) Methyl 5-(4,4,5,5-tetramethyl-1,3,2-dioxaborolan-2-yl)-1,1'-biphenyl-2-carboxylate
MS (m/z): 361 (M+Na)

Preparation 51

To a solution of 4-bromo-2-fluorobenzaldehyde (5.0 g) in dimethylsulfoxide (40 ml) were added phenol (2.78 g) and potassium carbonate (4.08 g), and the mixture was stirred at 100° C. for 3 hours. The solution was diluted with water and ethyl acetate. The organic layer was separated and washed with brine. The extract was dried over magnesium sulfate, filtrated and concentrated under reduced pressure. The residue was purified by column chromatography on silica gel with ethyl acetate and hexane to give 4-bromo-2-phenoxy-1-benzaldehyde (7.3 g) as a white solid.
NMR (CDCl$_3$, δ): 6.90-7.60(7H, m), 7.80(1H, d, J=8 Hz), 10.48(1H, s)

Preparation 52

The following compounds were obtained according to a similar manner to that of Preparation 14.

(1) 4-(2-Methoxy-2-oxoethyl)phenylboronic acid
MS (m/z): 193 (M−H)

(2) 3-(2-Methoxy-2-oxoethyl)phenylboronic acid
MS (m/z): 194 (M+H)

(3) 4-[(2R)-2-[[(Benzyloxy)carbonyl]amino]propyl]-phenylboronic acid
MS (m/z): 312 (M−H)

(4) 4-[2-[N-Benzyl-N-(tert-butoxycarbonyl)amino]ethyl]-phenylboronic acid
(−)ESI-MS m/z: 354 (M−H)$^−$ Preparation 53

The following compounds were obtained according to a similar manner to that of Preparation 23.

(1) Methyl [4'-[(2R)-2-[[(benzyloxy)carbonyl]amino]propyl]-1,1'-biphenyl-4-yl]acetate
MS (m/z): 418 (M+H)

(2) Ethyl 5-[4-[(2R)-2-[[(benzyloxy)carbonyl]amino]propyl]-phenyl]-1-naphthoate
MS (m/z): 490 (M+Na)

(3) Methyl 5-(benzyloxy)-1,1'-biphenyl-2-carboxylate
MS (m/z): 341 (M+Na)

Preparation 54

The following compounds were obtained according to a similar manner to that of Preparation 36.

(1) Methyl [4'-[(2R)-2-aminopropyl]-1,1'-biphenyl-4-yl]acetate
MS (m/z): 284 (M+H)

(2) Ethyl 5-[4-[(2R)-2-aminopropyl]phenyl)-1-naphthoate
MS (m/z): 356 (M+Na)

(3) Methyl 5-hydroxy-1,1'-biphenyl-2-carboxylate
MS (m/z): 251 (M+Na)

Preparation 55

To a mixture of 5-hydroxy-1-naphthyl trifluoromethanesulfonate (8.0 g) in N,N-dimethylformamide (35 ml) and ethanol (5.0 ml) were added 1,3-bis(diphenylphosphino)-propane (621 mg), palladium acetate(II) (3.7 mg) and triethylamine (1.35 g), and the mixture was stirred at 100° C. for 1 hour under carbon-monoxide. The mixture was diluted with ethyl acetate and water. The organic layer was separated, washed with brine, dried over magnesium sulfate and evaporated. The residue was purified by column chromatography on silica gel (hexane/ethyl acetate=5/1) to give ethyl 5-hydroxy-1-naphthoate (1.7 g) as a colorless oil.
MS (m/z): 239 (M+Na)

Preparation 56

To a solution of 4-bromo-2-fluorobenzoic acid (2.0 g) in tetrahydrofran (15 ml) was added 2M isobutylmagnesium bromide in diethyl ether (13.5 ml) dropwise on ice-cooling, and the mixture was stirred at 0° C. for 1 hour. The mixture was diluted with ethyl acetate and water. The organic layer was separated, washed with brine, dried over magnesium sulfate and evaporated. To the solution of the residue in N,N-dimethylformamide (20 ml) was added methyliodide (1.14 g) and potassium carbonate (1.89 g), and the mixture was stirred at 20° C. for 3 hours. The mixture was diluted with ethyl acetate and water. The organic layer was separated, washed with brine, dried over magnesium sulfate and evaporated. The residue was purified by column chromatography on silica gel (hexane/ethyl acetate=2/1) to give methyl 4-bromo-2-isobutylbenzoate (1.5 g) as a colorless oil.
NMR (DMSO-$d_6$, δ): 0.80(6H, d, J=8 Hz), 1.80-2.00(1H, m), 2.80(2H, d, J=8 Hz), 3.80(3H, s), 7.40-7.80(3H, m)

Preparation 57

The following compounds were obtained according to a similar manner to that of Preparation 56.

(1) Methyl 4-bromo-2-isopropylbenzoate
NMR (DMSO-$d_6$, δ): 1.20(6H, d, J=7 Hz), 3.50-3.60(1H, m), 3.83(1H, s), 7.50-7.70(3H, m) MS (m/z): 516 (M+H)

(2) Methyl 4-bromo-2-propylbenzoate
NMR (DMSO-$d_6$, δ): 0.85(3H, t, J=7 Hz), 1.40-1.70(2H, m), 2.80-3.00(2H, m), 3.82(3H, s), 7.60-7.70(3H, m)

Preparation 58

The following compound was obtained according to a similar manner to that of Preparation 28.

tert-Butyl N-((2R)-2-hydroxy-2-phenylethyl)-N-[(1R)-2-(4-iodophenyl)-1-methylethyl]carbamate
MS (m/z): 482 (M+H)

Preparation 59

The following compounds were obtained according to a similar manner to that of Preparation 13.

(1) tert-Butyl N-benzyl-N-[2-[4-(4,4,5,5-tetramethyl-1,3,2-dioxaborolan-2-yl)phenyl]ethyl)carbamate
(+)ESI-MS m/z: 460 (M+Na)$^+$ (2) 2-(1-Piperidinyl)-4-(4,4,5,5-tetramethyl-1,3,2-dioxaborolan-2-yl)benzaldehyde
(+)ESI-MS m/z: 581 (M+Na)$^+$ Preparation 60

To a solution of 2-(3-methoxyphenyl)ethanamine (5.6 g) in dichloromethane (50 ml) was added 1M boron tribromide in dichloromethane (75 ml). The mixture was stirred at 20° C. for 16 hours and evaporated in vacuo. To the residue, saturated sodium bicarbonate (50 ml) and tetrahydrofuran (150 ml) were added. The pH value of the mixture was kept between 7 to 8 with 1N aqueous sodium hydroxide solution. To the mixture, a solution of di-tert-butyl dicarbonate (8.08 g) in tetrahydrofuran (10 ml) was added, stirred at 20° C. for 1 hour. The mixture was diluted with ethyl acetate and water. The organic layer was separated, washed with brine, dried over magnesium sulfate and evaporated to give tert-butyl 2-(3-hydroxyphenyl)ethylcarbamate (8.2 g).

(+)ESI-MS m/z: 260 (M+Na)+

Preparation 61

To a solution of tert-butyl 2-(3-hydroxyphenyl)-ethylcarbamate (730 mg) and potassium carbonate (893 mg) in N,N-dimethylformamide (10 ml) was added methyl 4-bromo-(3-bromomethyl)benzoate (1.52 g), and the mixture was stirred at room temperature for 16 hours. The mixture was partitioned between ethyl acetate and water. The organic layer was separated, washed with water and brine, dried over magnesium sulfate and evaporated under reduced pressure. The residue was purified by column chromatography on silica gel (hexane/ethyl acetate=2/1) to give methyl 4-bromo-3-[[3-[2-[(tert-butoxycarbonyl)amino]ethyl]phenoxy)methyl]-benzoate (970 mg)

(+)ESI-MS m/z: 464 (M+H)+

Preparation 62

To a solution of methyl 4-bromo-3-[[3-[2-[(tert-butoxycarbonyl)amino]ethyl]phenoxy]methyl]benzoate (410 mg) in N,N-dimethylacetamide (4.0 ml) was added dichlorobis (triphenylphosphine)palladium(II) (124 mg) and sodium acetate (362 mg), and the mixture was stirred at 130° C. for 1.5 hours under nitrogen. The mixture was cooled to room temperature, diluted with ethyl acetate and water. The organic layer was separated, washed with brine, dried over magnesium sulfate and evaporated. The residue was purified by column chromatography on silica gel (hexane/ethyl acetate=3/1) to give methyl 3-[2-[(tert-butoxycarbonyl)amino]ethyl]-6H-benzo[c]chromene-8-carboxylate (190 mg).

(+)ESI-MS m/z: 406 (M+Na)+

Preparation 63

The following compounds were obtained according to a similar manner to that of Example 7.

(1) Ethyl 6-[4-[2-[N-benzyl-N-(tert-butoxycarbonyl)amino]-ethyl]phenyl}nicotinate
(+)ESI-MS m/z: 461 (M+H)+

(2) Methyl 4'-[2-[N-benzyl-N-(tert-butoxycarbonyl)amino]-ethyl]-2,6-dimethyl-1,1'-biphenyl-4-carboxylate
(+)ESI-MS m/z: 474 (M+H)+

Preparation 64

The following compounds were obtained according to a similar manner to that of Example 27.

(1) Methyl 3-(2-aminoethyl)-6H-benzo[c]chromene-8-carboxylate
(+)ESI-MS m/z: 284 (M+H)+

(2) Ethyl 6-[4-[2-(benzylamino)ethyl]phenyl]nicotinate hydrochloride
(+)ESI-MS m/z: 361 (M+H)+

Preparation 65

The following compounds were obtained according to a similar manner to that of Preparation 16.

(1) 3-[2-[N-(tert-Butoxycarbonyl)-N-[(2R)-2-(3-chlorophenyl)-2-hydroxyethyl]amino]ethyl]phenyl trifluoromethanesulfonate
(+)ESI-MS m/z: 546 (M+Na)+

(2) 4-[2-[N-(tert-Butoxycarbonyl)-N-[(2R)-2-(3-chlorophenyl)-2-hydroxyethyl]amino]ethyl]-2-methoxyphenyl trifluoromethanesulfonate
(+)ESI-MS m/z: 576 (M+Na)+

(3) 4-[2-[N-(tert-Butoxycarbonyl)-N-[(2R)-2-(3-chlorophenyl)-2-hydroxyethyl]amino]ethyl]-2-chlorophenyl trifluoromethanesulfonate
(+)ESI-MS m/z: 581 (M+Na)+

Preparation 66

The following compound was obtained according to a similar manner to that of Example 5.

Methyl 4'-[2-(benzylamino)ethyl]-2,6-dimethyl-1,1'-biphenyl-4-carboxylate
(+)ESI-MS m/z: 374 (M+H)+

Preparation 67

To a mixture of 3-chloro-4-hydroxyphenylacetic acid (2.96 g), (1R)-2-amino-1-(3-chlorophenyl)ethanol hydrochloride (3.0 g), and 1-hydroxybenzotriazole (2.14 g) in N,N-dimethylformamide (20 ml) was added 1-(3-dimethylaminopropyl)-3-ethylcarbodiimide (2.46 g), and the mixture was stirred at room temperature for 2 hours. The mixture was partitioned between ethyl acetate and water. The organic layer was separated, washed successively with sodium bicarbonate solution and brine, dried over magnesium sulfate and evaporated under reduced pressure to give an amide product. To a tetrahydrofuran (30 ml) solution of the product, 2M borane-dimethyl sulfide complex in tetrahydrofuran (23 ml) was added at room temperature, and the mixture was refluxed for 30 minutes. To the mixture, 6N hydrochloride acid (29.5 ml) was added dropwise below 10° C., and the mixture was stirred at room temperature for 3 hours. To the reaction mixture, 3N aqueous sodium hydroxide solution (58 ml) below 10° C. was added and di-tert-butyl dicarbonate (3.46 g) was added portionally at room temperature. The pH value was kept between 7 to 8 by using 1N aqueous sodium hydroxide solution. The mixture was stirred at room temperature for 1 hour. The mixture was partitioned between ethyl acetate and water. The organic layer was separated, washed brine, dried over magnesium sulfate and evaporated under reduced pressure. The residue was purified by column chromatography on silica gel (hexane/ethyl acetate=2/1) to give tert-butyl N-[2-(3-chloro-4-hydroxyphenyl)ethyl]-N-[(2R)-2-(3-chlorophenyl)-2-hydroxyethyl]carbamate (7.0 g).

(+)ESI-MS m/z: 448 (M+Na)+

Preparation 68

The following compound was obtained according to a similar manner to that of Preparation 67.

tert-Butyl N-[(2R)-2-(3-chlorophenyl)-2-hydroxyethyl]-N-[2-(4-hydroxy-3-methoxyphenyl)ethyl]carbamate
(+)ESI-MS m/z: 444 (M+Na)+

Preparation 69

A mixture of 4-bromo-2-fluorobenzaldehyde (3.0 g), piperidine (2.93 ml) and potassium carbonate (5.11 g) in N,N-dimethylformamide (30 ml) was stirred at 100° C. for 12 hours. The mixture was cooled to room temperature. The mixture was partitioned between ethyl acetate and water. The organic layer was separated, washed with water, saturated aqueous ammonium chloride solution and brine, dried over magnesium sulfate and evaporated under reduced pressure. The residue was purified by column chromatography on silica gel (hexane/ethyl acetate=9/1) to give 4-bromo-2-(1-piperidinyl)benzaldehyde (3.5 g).

(+)ESI-MS m/z: 268 (M+H)+

Preparation 70

The following compound was obtained according to a similar manner to that of Example 23.

tert-Butyl N-benzyl-N-[2-(4-bromophenyl)ethyl]carbamate
(+)ESI-MS m/z: 390 (M+H)+

EXAMPLE 32

The following compounds were obtained according to a similar manner to that of Example 7.

(1) 4'-[(2R)-2-[[(2R)-2-(3-Chlorophenyl)-2-hydroxyethyl]-amino]propyl]-3-propoxy-1,1'-biphenyl-4-carboxylic acid hydrochloride NMR (DMSO-d$_6$, δ): 1.05(3H, t, J=7.4 Hz), 1.35(3H, d, J=6.2 Hz), 1.6-1.9(2H, m), 2.8-3.8(5H, m), 4.11(2H, t, J=7.4 Hz), 5.0-5.3(1H, m), 6.3-6.4(1H, m), 7.2-7.8(11H, m), 8.55 (1H, br s), 9.19(1H, br s) MS m/z: 468 (M+H)

(2) 4'-[2-[[(2R)-2-(3-Chlorophenyl)-2-hydroxyethyl]amino]-ethyl]-3-hydroxy-1,1'-biphenyl-4-carboxylic acid hydrochloride NMR (DMSO-d$_6$, δ): 2.8-3.0(6H, m), 4.8-5.0(1H, m), 6.33 (1H, m), 7.0-7.9(11H, m) MS m/z: 411 (M+H)

(3) 3-Hydroxy-4'-[(2R)-2-[[(2R)-2-hydroxy-2-phenylethyl]-amino]propyl]-1,1'-biphenyl-4-carboxylic acid hydrochloride NMR (DMSO-d$_6$, δ): 1.12(3H, d, J=6.4 Hz), 2.6-3.2(5H, m), 4.9-5.1(1H, m), 6.23(1H, m), 7.2-7.9(11H, m), 8.77(1H, br s), 9.03(1H, br s) MS m/z: 392 (M+H)

(4) 3-Ethoxy-4'-[(2R)-2-[[(2R)-2-hydroxy-2-phenylethyl]-amino]propyl]-1,1'-biphenyl-4-carboxylic acid hydrochloride NMR (DMSO-d$_6$, δ): 1.15(3H, d, J=6.4 Hz), 1.36(3H, t, J=7.0 Hz), 2.6-3.2(5H, m), 4.21(2H, q, J=7.0 Hz), 4.9-5.1 (1H, m), 6.23(1H, m), 7.2-7.7(11H, m) MS m/z: 418 (M−H)

(5) 4'-[(2R)-2-[[(2R)-2-Hydroxy-2-phenylethyl]amino]-propyl]-3-propoxy-1,1'-biphenyl-4-carboxylic acid hydrochloride NMR (DMSO-d$_6$, δ): 1.03(3H, t, J=7.4 Hz), 1.12(3H, d, J=6.4 Hz), 1.74(2H, m), 2.6-3.2(5H, m), 4.11(2H, q, J=7.0 Hz), 4.9-5.1(1H, m), 6.23(1H, m), 7.2-7.7(11H, m) MS m/z: 434 (M+H)

(6) 3-Butoxy-4'-[(2R)-2-[[(2R)-2-hydroxy-2-phenylethyl]-amino]propyl]-1,1'-biphenyl-4-carboxylic acid hydrochloride NMR (DMSO-d$_6$, δ): 0.94(3H, t, J=7.4 Hz), 1.12(3H, d, J=6.4 Hz), 1.3-1.8(4H, m), 2.6-3.2(5H, m), 4.15(2H, q, J=7.0 Hz), 4.9-5.1(1H, m), 6.23(1H, m), 7.2-7.7(11H, m) MS m/z: 448 (M+H)

(7) 4'-[(2R)-2-[[(2R)-2-Hydroxy-2-phenylethyl]amino]-propyl]-3-(pentyloxy)-1,1'-biphenyl-4-carboxylic acid hydrochloride NMR (DMSO-d$_6$, δ): 0.89(3H, t, J=7.4 Hz), 1.13(3H, d, J=6.4 Hz), 1.2-1.8(6H, m), 2.6-3.2(5H, m), 4.14(2H, q, J=7.0 Hz), 4.9-5.1(1H, m), 6.23(1H, m), 7.2-7.7(11H, m) MS m/z: 462 (M+H)

(8) 3-(Heptyloxy)-4'-[(2R)-2-[[(2R)-2-hydroxy-2-phenyl-ethyl]amino]propyl]-1,1'-biphenyl-4-carboxylic acid hydrochloride NMR (DMSO-d$_6$, δ): 0.86(3H, t, J=7.4 Hz), 1.16(3H, d, J=6.4 Hz), 1.1-1.8(10H, m), 2.6-3.2(5H, m), 4.14(2H, q, J=7.0 Hz), 4.9-5.1(1H, m), 6.23(1H, m), 7.2-7.7(11H, m) MS m/z: 490 (M+H)

(9) 4'-[(2R)-2-[[(2R)-2-Hydroxy-2-phenylethyl]amino]-propyl]-3-isobutoxy-1,1'-biphenyl-4-carboxylic acid hydrochloride NMR (DMSO-d$_6$, δ): 1.03(6H, t, J=6.2 Hz), 1.16(3H, d, J=6.4 Hz), 1.8-2.2(1H, m), 2.6-3.2(5H, m), 3.93(2H, d, J=6.2 Hz), 4.9-5.1(1H, m), 6.23(1H, m), 7.2-7.7(11H, m) MS m/z: 448 (M+H)

(10) 3-(Allyloxy)-4'-[(2R)-2-[[(2R)-2-hydroxy-2-phenyl-ethyl]amino]propyl]-1,1'-biphenyl-4-carboxylic acid hydrochloride NMR (DMSO-d$_6$, δ): 1.16(3H, d, J=6.4 Hz), 2.6-3.2(5H, m), 4.77(2H, m), 4.9-5.1(1H, m), 5.27(1H, dd, J=1.8, 10.6 Hz), 5.40(1H, dd, J=1.8, 17.2 Hz), 5.9-6.2(1H, m), 6.23(1H, m), 7.2-7.7(11H, m) MS m/z: 432 (M+H)

(11) 4'-[(2R)-2-[[(2R)-2-Hydroxy-2-phenylethyl]amino]-propyl]-3-[(2-methyl-2-propenyl)oxy]-1,1'-biphenyl-4-carboxylic acid hydrochloride NMR (DMSO-d$_6$, δ): 1.16(3H, d, J=6.4 Hz), 1.69(3H, s), 2.6-3.2(5H, m), 4.77(2H, m), 4.65(2H, s), 4.9-5.1(1H, m), 4.9-5.2(2H, m), 6.23(1H, m), 7.2-7.7(11H, m) MS m/z: 446 (M+H)

(12) 3-(2-Fluoroethoxy)-4'-[(2R)-2-[[(2R)-2-hydroxy-2-phenylethyl]amino]propyl]1,1'-biphenyl-4-carboxylic acid hydrochloride NMR (DMSO-d$_6$, δ): 1.16(3H, d, J=6.4 Hz), 2.6-3.2(5H, m), 4.3-4.8(4H, m), 4.9-5.1(1H, m), 6.23(1H, m), 7.2-7.7 (11H, m) MS m/z: 438 (M+H)

(13) 3-(2,2-Difluoroethoxy)-4'-[(2R)-2-[[(2R)-2-hydroxy-2-phenylethyl]amino]propyl)-1,1'-biphenyl-4-carboxylic acid hydrochloride NMR (DMSO-d$_6$, δ): 1.13(3H, d, J=6.4 Hz), 2.6-3.2(5H, m), 4.3-4.7(2H, m), 4.9-5.1(1H, m), 6.0-6.5(2H, m), 7.2-7.7 (11H, m) MS m/z: 456 (M+H)

(14) 4'-[(2R)-2-[[(2R)-2-Hydroxy-2-phenylethyl]amino]-propyl]-3-(2,2,2-trifluoroethoxy)-1,1'-biphenyl-4-carboxylic acid hydrochloride NMR (DMSO-d$_6$, δ): 1.13(3H, d, J=6.4 Hz), 2.6-3.2(5H, m), 4.7-5.1(3H, m), 6.24(1H, m), 7.2-7.7(11H, m) MS m/z: 472 (M−H)

(15) 3-(2-Hydroxyethoxy)-4'-[(2R)-2-[[(2R)-2-hydroxy-2-phenylethyl]amino]propyl]-1,1'-biphenyl-4-carboxylic acid hydrochloride NMR (DMSO-d$_6$, δ): 1.13(3H, d, J=6.4 Hz), 2.6-3.2(5H, m), 3.8(2H, m), 4.15(2H, m), 4.9-5.1(1H, m), 6.24(1H, m), 7.2-7.7(11H, m) MS m/z: 434 (M−H)

(16) 4'-[(2R)-2-[[(2R)-2-Hydroxy-2-phenylethyl]amino]-propyl]-3-(2-methoxyethoxy)-1,1'-biphenyl-4-carboxylic acid hydrochloride NMR (DMSO-d$_6$, δ): 1.12(3H, d, J=6.4 Hz), 2.6-3.2(5H, m), 3.33(3H, s), 3.70(2H, m), 4.29(2H, m), 4.9-5.1(1H, m), 6.22(1H, m), 7.2-7.7(11H, m) MS m/z: 450 (M+H)

(17) 3-(3-Fluoropropoxy)-4'-[(2R)-2-[[(2R)-2-hydroxy-2-phenylethyl]amino]propyl]-1,1'-biphenyl-4-carboxylic acid hydrochloride NMR (DMSO-d$_6$, δ): 1.13(3H, d, J=6.4 Hz), 2.0-2.4(2H, m), 2.6-3.2(5H, m), 4.25(2H, t, J=6.0 Hz), 4.56(1H, t, J=5.8 Hz), 4.83(1H, t, J=6.0 Hz), 4.9-5.1(1H, m), 6.24(1H, m), 7.2-7.7(11H, m) MS m/z: 452 (M+H)

(18) 4'-[(2R)-2-[[(2R)-2-Hydroxy-2-phenylethyl]amino]-propyl]-3-(3,3,3-trifluoropropoxy)-1,1'-biphenyl-4-carboxylic acid hydrochloride NMR (DMSO-d$_6$, δ): 1.13(3H, d, J=6.4 Hz), 2.6-3.2(7H, m), 4.39(2H, t, J=6.0 Hz), 4.9-5.1(1H, m), 6.24(1H, m), 7.2-7.7(11H, m) MS m/z: 488 (M+H)

(19) 3-(Cyclopropyloxy)-4'-[(2R)-2-[[(2R)-2-hydroxy-2-phenylethyl]amino]propyl)-1,1'-biphenyl-4-carboxylic acid hydrochloride NMR (DMSO-d$_6$, δ): 1.13(3H, d, J=6.4 Hz), 2.6-3.2(5H, m), 4.9-5.1(2H, m), 6.24(1H, m), 7.2-7.7(11H, m) MS m/z: 432 (M+H)

(20) 3-(Cyclobutyloxy)-4'-[(2R)-2-[[(2R)-2-hydroxy-2-phenylethyl]amino]propyl]-1,1'-biphenyl-4-carboxylic acid hydrochloride NMR (DMSO-$d_6$, δ): 1.13(3H, d, J=6.4 Hz), 1.2-2.4(6H, m), 2.6-3.2(5H, m), 4.9-5.1(2H, m), 6.24(1H, m), 7.2-7.7 (11H, m) MS m/z: 446 (M+H)

(21) 3-(Cyclopentyloxy)-4'-[(2R)-2-[[(2R)-2-hydroxy-2-phenylethyl]amino]propyl]-1,1'-biphenyl-4-carboxylic acid hydrochloride NMR (DMSO-$d_6$, δ): 1.13(3H, d, J=6.4 Hz), 1.2-2.0(8H, m), 2.6-3.2(5H, m), 4.9-5.1(2H, m), 6.24(1H, m), 7.2-7.7 (11H, m) MS m/z: 460 (M+H)

(22) 3-(Cyclopropylmethoxy)-4'-[(2R)-2-[[(2R)-2-hydroxy-2-phenylethyl]amino]propyl]-1,1'-biphenyl-4-carboxylic acid hydrochloride NMR (DMSO-$d_6$, δ): 0.2-0.7(2H, m), 0.9-1.3(6H, m), 2.6-3.2(5H, m), 4.03(2H, d, J=6.6 Hz), 4.9-5.1(1H, m), 6.24(1H, m), 7.2-7.7(11H, m) MS m/z: 446 (M+H)

(23) 3-(Cyclohexylmethoxy)-4'-[(2R)-2-[[(2R)-2-hydroxy-2-phenylethyl]amino]propyl]-1,1'-biphenyl-4-carboxylic acid hydrochloride NMR (DMSO-$d_6$, δ): 1.0-1.9(14H, m), 2.6-3.2(5H, m), 3.93(2H, d, J=6.6 Hz), 4.9-5.1(1H, m), 6.24(1H, m), 7.2-7.7 (11H, m) MS m/z: 488 (M+H)

(24) 4'-[2-[[(2R)-2-Phenyl-2-hydroxyethyl]amino]ethyl]-1, 1'-biphenyl-4-nitrile

MS m/z: 457 (M+H)

(25) 4'-[(2R)-2-[[(2R)-2-Hydroxy-2-phenylethyl]amino]propyl]-3-phenoxy-1,1'-biphenyl-4-carboxylic acid hydrochloride NMR (DMSO-$d_6$, δ): 1.13(3H, d, J=6.4 Hz), 2.6-3.2(5H, m), 4.9-5.1(1H, m), 6.24(1H, m), 6.8-7.9(16H, m) MS m/z: 468 (M+H)

(26) 4'-[2-[[(2R)-2-Hydroxy-2-phenylethyl]amino]ethyl]-3-methoxy-1,1'-biphenyl-4-carboxylic acid hydrochloride NMR (DMSO-$d_6$, δ): 2.8-3.3(6H, m), 4.9-5.1(1H, m), 6.22 (1H, m), 7.2-7.8(12H, m) MS m/z: 392(M+H)

(27) 3-Ethoxy-4'-[2-[[(2R)-2-hydroxy-2-phenylethyl]amino]-ethyl]-1,1'-biphenyl-4-carboxylic acid hydrochloride NMR (DMSO-$d_6$, δ): 1.35(3H, t, J=6.8 Hz), 2.8-3.3(6H, m), 4.20(2H, q, J=6.8 Hz), 4.9-5.1(1H, m), 6.22(1H, m), 7.2-7.8(12H, m) MS m/z: 406 (M+H)

(28) 4'-[2-[[(2R)-2-Hydroxy-2-phenylethyl]amino]ethyl]-3-propoxy-1,1'-biphenyl-4-carboxylic acid hydrochloride NMR (DMSO-$d_6$, δ): 1.01(3H, t, J=6.8 Hz), 1.6-1.9(2H, m), 2.9-3.4(6H, m), 4.11(2H, q, J=6.8 Hz), 4.9-5.1(1H, m), 6.22(1H, m), 7.2-7.8(12H, m) MS m/z: 420 (M+H)

(29) 4'-[2-[[(2R)-2-Hydroxy-2-phenylethyl]amino]ethyl]-3-isopropoxy-1,1'-biphenyl-4-carboxylic acid hydrochloride NMR (DMSO-$d_6$, δ): 1.31(6H, t, J=6.8 Hz), 2.9-3.4(6H, m), 4.7-4.9(1H, m), 4.9-5.1(1H, m), 6.22(1H, m), 7.2-7.8 (12H, m) MS m/z: 420 (M+H)

(30) 4'-[2-[[(2R)-2-Hydroxy-2-phenylethyl]amino]ethyl]-3-isobutoxy-1,1'-biphenyl-4-carboxylic acid hydrochloride NMR (DMSO-$d_6$, δ): 1.02(6H, t, J=6.8 Hz), 1.9-2.1(1H, m), 2.9-3.4(6H, m), 3.92(2H, d, J=6.8 Hz), 4.9-5.1(1H, m), 6.22(1H, m), 7.2-7.8(12H, m) MS m/z: 434 (M+H)

(31) 3-(Allyloxy)-4'-[2-[[(2R)-2-hydroxy-2-phenylethyl]amino]ethyl]-1,1'-biphenyl-4-carboxylic acid hydrochloride NMR (DMSO-$d_6$, δ): 2.9-3.4(6H, m), 3.92(2H, d, J=6.8 Hz), 4.72(2H, m), 5.2-5.7(2H, m), 4.9-5.1(1H, m), 6.0-6.2 (1H, m), 6.22(1H, m), 7.2-7.8(12H, m) MS m/z: 418(M+H)

(32) 3-(2-Fluoroethoxy)-4'-[2-[[(2R)-2-hydroxy-2-phenylethyl]amino]ethyl]-1,1'-biphenyl-4-carboxylic acid hydrochloride NMR (DMSO-$d_6$, δ): 2.9-3.4(6H, m), 4.3-4.7(3H, m), 4.8-4.9(1H, m), 4.9-5.1(1H, m), 6.22(1H, m), 7.2-7.8(12H, m) MS m/z: 424 (M+H)

(33) 3-(3-Fluoropropoxy)-4'-[2-[[(2R)-2-hydroxy-2-phenylethyl]amino]ethyl]-1,1'-biphenyl-4-carboxylic acid hydrochloride NMR (DMSO-$d_6$, δ): 1.9-2.3(2H, m), 2.9-3.4(6H, m), 4.25 (2H, t, J=6.0 Hz), 4.56(1H, t, J=5.9 Hz), 4.80(1H, t, J=5.8 Hz), 4.9-5.1(1H, m), 6.22(1H, m), 7.2-7.8(12H, m) MS m/z: 438 (M+H)

(34) 3-(Cyclopropyloxy)-4'-[2-[[(2R)-2-hydroxy-2-phenylethyl]amino]ethyl]-1,1'-biphenyl-4-carboxylic acid hydrochloride NMR (DMSO-$d_6$, δ): 2.9-3.4(6H, m), 4.9-5.1(1H, m), 6.22 (1H, m), 7.2-7.8(12H, m) MS m/z: 392 (M+H)

(35) 3-(Cyclohexyloxy)-4'-[2-[[(2R)-2-hydroxy-2-phenylethyl]amino]ethyl]-1,1'-biphenyl-4-carboxylic acid hydrochloride NMR (DMSO-$d_6$, δ): 1.2-2.0(10H, m), 2.9-3.4(6H, m), 4.64(1H, m), 4.9-5.1(1H, m), 6.22(1H, m), 7.2-7.8(12H, m) MS m/z: 460 (M+H)

(36) 4'-[2-[[(2R)-2-Hydroxy-2-phenylethyl]amino]ethyl)-3-phenoxy-1,1'-biphenyl-4-carboxylic acid hydrochloride NMR (DMSO-$d_6$, δ): 2.9-3.4(6H, m), 4.9-5.1(1H, m), 6.22 (1H, m), 6.9-8.0(17H, m) MS m/z: 454 (M+H)

(37) 3-(Benzyloxy)-4'-[2-[[(2R)-2-hydroxy-2-phenylethyl]amino]ethyl]-1,1'-biphenyl-4-carboxylic acid hydrochloride NMR (DMSO-$d_6$, δ): 2.9-3.4(6H, m), 4.9-5.1(1H, m), 5.33 (2H, m), 6.22(1H, m), 7.2-7.8(17H, m) MS m/z: 468 (M+H)

(38) 4'-[2-[[(2R)-2-Hydroxy-2-phenylethyl]amino]ethyl]-3-(2,2,2-trifluoroethoxy)-1,1'-biphenyl-4-carboxylic acid hydrochloride NMR (DMSO-$d_6$, δ): 2.9-3.4(6H, m), 4.3-5.1(2H, m), 6.22 (1H, m), 7.2-7.8(12H, m) MS m/z: 460(M+H)

(39) 4'-[2-[[(2R)-2-Hydroxy-2-phenylethyl]amino]ethyl]-2-methyl-1,1'-biphenyl-4-carboxylic acid hydrochloride NMR (DMSO-$d_6$, δ): 2.28(3H, s), 2.9-3.4(6H, m), 4.9-5.1 (1H, m), 5.33(2H, m), 6.22(1H, m), 7.2-7.8(12H, m) MS m/z: 476 (M+H)

(40) 4'-[2-[[(2R)-2-(3-Fluorophenyl)-2-hydroxyethyl]amino]ethyl]-3-propoxy-1,1'-biphenyl-4-carboxylic acid hydrochloride NMR (DMSO-$d_6$, δ): 1.01(3H, t, J=7.4 Hz), 1.5-1.9(2H, m), 2.9-3.4(6H, m), 4.11(2H, q, J=7.4 Hz), 4.9-5.1(1H, m), 6.22(1H, m), 7.1-7.8(11H, m) MS m/z: 438 (M+H)

(41) 4'-[(2R)-2-[[(2R)-2-(3-Fluorophenyl)-2-hydroxyethyl]amino]propyl]-3-propoxy-1,1'-biphenyl-4-carboxylic acid hydrochloride NMR (DMSO-$d_6$, δ): 0.99(3H, t, J=7.4 Hz), 1.10(3H, d, J=6.8 Hz), 1.5-1.9(2H, m), 2.7-3.4(5H, m), 4.03(2H, q, J=7.4 Hz), 4.9-5.1(1H, m), 6.22(1H, m), 7.1-7.8(11H, m) MS m/z: 450 (M−H)

(42) 4'-[2-[[(2R)-2-(3-Fluorophenyl)-2-hydroxyethyl]amino]-ethyl]-3-isopropoxy-1,1'-biphenyl-4-carboxylic acid hydrochloride NMR (DMSO-$d_6$, δ): 1.31(6H, d, J=6.0 Hz), 2.9-3.4(6H, m), 4.81(1H, m), 4.9-5.1(1H, m), 6.22(1H, m), 7.1-7.8(11H, m) MS m/z: 438 (M+H)

(43) 4'-[(2R)-2-[[(2R)-2-(3-fluorophenyl)-2-hydroxyethyl]-amino]propyl]-3-isopropoxy-1,1'-biphenyl-4-carboxylic acid hydrochloride NMR (DMSO-d$_6$, δ): 1.10(3H, d, J=6.8 Hz), 1.31(6H, d, J=6.0 Hz), 2.7-3.4(5H, m), 4.82(1H, m), 4.9-5.1(1H, m), 6.22(1H, m), 7.1-7.8(11H, m) MS m/z: 450 (M−H)

(44) 3-(Cyclohexyloxy)-4'-[(2R)-2-[[(2R)-2-(3-fluorophenyl)-2-hydroxyethyl)amino]propyl]-1,1'-biphenyl-4-carboxylic acid hydrochloride NMR (DMSO-d$_6$, δ): 1.13(3H, d, J=6.8 Hz), 1.2-2.0(10H, m), 2.7-3.4(5H, m), 4.65(1H, m), 4.9-5.1(1H, m), 6.22(1H, m), 7.1-7.8(11H, m) MS m/z: 490 (M−H)

(45) 4'-[2-[[(2R)-2-(4-Chlorophenyl)-2-hydroxyethyl]amino]-ethyl]-3-propoxy-1,1'-biphenyl-4-carboxylic acid hydrochloride NMR (DMSO-d$_6$, δ): 1.01(3H, t, J=7.4 Hz), 1.5-1.9(2H, m), 2.9-3.4(6H, m), 4.10(2H, q, J=7.4 Hz), 4.9-5.1(1H, m), 6.28(1H, m), 7.1-7.8(11H, m) MS m/z: 438 (M+H)

(46) 4'-[2-[[(2R)-2-(4-Chlorophenyl)-2-hydroxyethyl]amino]-ethyl]-3-isopropoxy-1,1'-biphenyl-4-carboxylic acid hydrochloride NMR (DMSO-d$_6$, δ): 1.29(6H, d, J=6.0 Hz), 2.9-3.4(6H, m), 4.84(1H, m), 4.9-5.1(1H, m), 6.30(1H, m), 7.1-7.8(11H, m) MS m/z: 454 (M+H)

(47) 4'-[(2R)-2-[[(2R)-2-(4-Chlorophenyl)-2-hydroxyethyl]-amino]propyl]-3-propoxy-1,1'-biphenyl-4-carboxylic acid hydrochloride NMR (DMSO-d$_6$, δ): 1.00(3H, t, J=7.4 Hz), 1.12(3H, d, J=6.8 Hz), 1.5-1.9(2H, m), 2.7-3.4(5H, m), 4.03(2H, q, J=7.4 Hz), 4.9-5.1(1H, m), 6.32(1H, m), 7.1-7.8(11H, m) MS m/z: 468 (M−H)

(48) 4'-[(2R)-2-[[(2R)-2-(4-Chlorophenyl)-2-hydroxyethyl]-amino]propyl]-3-isopropoxy-1,1'-biphenyl-4-carboxylic acid hydrochloride NMR (DMSO-d$_6$, δ): 1.09(3H, d, J=6.8 Hz), 1.29(6H, d, J=6.0 Hz), 2.7-3.4(5H, m), 4.82(1H, m), 4.9-5.1(1H, m), 6.32(1H, m), 7.1-7.8(11H, m) MS m/z: 468 (M−H)

(49) 3-Ethoxy-4'-[(2R)-2-[[(2R)-2-hydroxy-2-(3-pyridyl)-ethyl]amino]propyl]-1,1'-biphenyl-4-carboxylic acid dihydrochloride NMR (DMSO-d$_6$, δ): 1.19(3H, d, J=6.8 Hz), 1.36(3H, t, J=7.0 Hz), 2.7-3.4(5H, m), 4.23(2H, q, J=7.0 Hz), 5.1-5.3(1H, m), 6.32(1H, m), 7.2-7.9(8H, m), 8.25(1H, d, J=8 Hz), 8.7-8.9(2H, m), 8.94(1H, m), 9.20(1H, m) MS m/z: 421 (M+H)

(50) 4'-[(2R)-2-[[(2R)-2-Hydroxy-2-(3-pyridyl)ethyl]-amino]propyl]-3-propoxy-1,1'-biphenyl-4-carboxylic acid hydrochloride NMR (DMSO-d$_6$, δ): 1.01(3H, t, J=7.4 Hz), 1.19(3H, d, J=6.8 Hz), 1.5-1.9(2H, m), 2.7-3.4(5H, m), 4.04(2H, q, J=7.4 Hz), 5.1-5.3(1H, m), 6.32(1H, m), 7.2-7.9(8H, m), 8.25(1H, d, J=8 Hz), 8.7-8.9(2H, m), 8.94(1H, m), 9.20(1H, m) MS m/z: 435 (M+H)

(51) 4'-[(2R)-2-[[(2R)-2-Hydroxy-2-(3-pyridyl)ethyl]-amino]propyl]-3-isobutoxy-1,1'-biphenyl-4-carboxylic acid dihydrochloride NMR (DMSO-d$_6$, δ): 1.01(6H, t, J=6.8 Hz), 1.17(3H, d, J=6.8 Hz), 1.9-2.1(1H, m), 2.7-3.4(5H, m), 3.93(2H, d, J=6.4 Hz), 5.2-5.4(1H, m), 7.2-7.9(8H, m), 8.4(1H, d, J=8 Hz), 8.7-8.9(2H, m), 9.09(1H, m), 9.42(1H, m) MS m/z: 449 (M+H)

(52) N-[[4'-[(2R)-2-[[(2R)-2-Hydroxy-2-(3-pyridyl)ethyl]-amino]propyl]-1,1'-biphenyl-4-yl]carbonyl]-1-phenyl-methanesulfonamide dihydrochloride MS m/z: 528 (M−H)

(53) 4'-[(2R)-2-[[(2R)-2-(6-Chloro-3-pyridyl)-2-hydroxyethyl]amino]propyl]-3-propoxy-1,1'-biphenyl-4-carboxylic acid dihydrochloride NMR (DMSO-d$_6$, δ): 1.01(3H, t, J=7.4 Hz), 1.12(3H, d, J=6.8 Hz), 1.7-1.9(2H, m), 2.7-3.4(5H, m), 4.11(2H, q, J=7.4 Hz), 4.9-5.3(1H, m), 7.2-7.8(10H, m), 8.56(1H, s) MS m/z: 469 (M+H)

(54) 4'-[2-[[(2R)-2-Hydroxy-2-(3-pyridyl)ethyl]amino]-ethyl]-3-isopropoxy-1,1'-biphenyl-4-carboxylic acid dihydrochloride NMR (DMSO-d$_6$, δ): 1.29(6H, d, J=6.0 Hz), 2.9-3.4(6H, m), 4.84(1H, m), 4.9-5.1(1H, m), 7.2-7.5(4H, m), 7.6-7.9(4H, m), 8.2-8.5(1H, m), 8.7-8.9(2H, m), 9.0-9.4(2H, m) MS m/z: 421 (M+H)

(55) 4'-[2-[[(2R)-2-Hydroxy-2-(3-pyridyl)ethyl]amino]-ethyl]-3-propoxy-1,1'-biphenyl-4-carboxylic acid dihydrochloride NMR (DMSO-d$_6$, δ): 1.01(3H, t, J=7.4 Hz), 1.5-1.9(2H, m), 3.0-3.4(6H, m), 4.11(2H, q, J=7.4 Hz), 5.0-5.3(1H, m), 7.2-7.5(4H, m), 7.6-7.9(4H, m), 8.3-8.5(1H, m), 8.7-8.9(2H, m), 9.0-9.4(2H, m) MS m/z: 421 (M+H)

(56) 3-(Cyclohexyloxy)-4'-[2-[[(2R)-2-hydroxy-2-(3-pyridyl)ethyl]amino]ethyl]-1,1'-biphenyl-4-carboxylic acid dihydrochloride NMR (DMSO-d$_6$, δ): 1.0-2.0(10H, m), 2.9-3.4(6H, m), 4.65(1H, m), 5.0-5.3(1H, m), 7.2-7.5(4H, m), 7.6-8.0(4H, m), 8.4-8.6(1H, m), 8.7-8.9(2H, m), 9.0-9.4(2H, m) MS m/z: 461 (M−H)

(57) 4'-[2-[[(2R)-2-(6-Chloro-3-pyridyl)-2-hydroxyethyl]-amino]ethyl]-3-propoxy-1,1'-biphenyl-4-carboxylic acid dihydrochloride NMR (DMSO-d$_6$, δ): 1.01(3H, t, J=7.4 Hz), 1.6-1.9(2H, m), 3.0-3.4(6H, m), 4.11(2H, q, J=7.4 Hz), 5.0-5.3(1H, m), 7.1-7.9(9H, m), 8.46(1H, s) MS m/z: 453 (M−H)

(58) 3-Butyl-4'-[(2R)-2-[[(2R)-2-hydroxy-2-phenylethyl]-amino]propyl]-1,1'-biphenyl-4-carboxylic acid hydrochloride NMR (DMSO-d$_6$, δ): 0.90(3H, t, J=7.4 Hz), 1.0-1.8(9H, m), 2.8-3.8(5H, m), 5.0-5.3(1H, m), 6.3-6.4(1H, m), 7.2-7.8 (11H, m) MS m/z: 432(M+H)

(59) 3-(3-Butenyl)-4'-[(2R)-2-[[(2R)-2-hydroxy-2-phenylethyl]amino]propyl]-1,1'-biphenyl-4-carboxylic acid hydrochloride MS m/z: 43b (M+H)

(60) 4'-[2-[[(2R)-2-hydroxy-2-phenylethyl]amino]-2-methylpropyl)-3-isopropoxy-1,1'-biphenyl-4-carboxylic acid hydrochloride MS m/z: 482 (M+H)

(61) 4'-[3-[[(2R)-2-Hydroxy-2-phenylethyl]amino]propyl]-3-isopropoxy-1,1'-biphenyl-4-carboxylic acid hydrochloride MS m/z: 434 (M+H)

(62) 4'-[2-[[(2R)-2-(3-Chlorophenyl)-2-hydroxyethyl]amino]-ethyl]-3-isopropoxy-1,1'-biphenyl-4-carboxylic acid hydrochloride NMR (DMSO-d$_6$, δ): 1.31 (6H, d, J=6.0 Hz), 2.8-3.0 (6H, m), 4.79 (1H, q, J=6.0 Hz), 4.8-5.0 (1H, m), 6.33 (1H, m), 7.0-7.9 (11H, m) MS m/z: 454 (M+H)

(63) Ethyl 4'-[2-[N-(tert-butoxycarbonyl)-N-[(2R)-2-(3-chlorophenyl)-2-hydroxyethyl]amino]ethyl]-1,1'-biphenyl-3-carboxylate (+)ESI-MS m/z: 524 (M+H)$^+$

(64) Methyl 3'-[2-[N-(tert-butoxycarbonyl)-N-[(2R)-2-(3-chlorophenyl)-2-hydroxyethyl]amino]ethyl]-1,1'-biphenyl-4-carboxylate (+)ESI-MS m/z: 510 (M+H)$^+$

(65) Methyl 4'-[2-[N-(tert-butoxycarbonyl)-N-[(2R)-2-(3-chlorophenyl)-2-hydroxyethyl]amino]ethyl]-2-fluoro-1,1'-biphenyl-4-carboxylate
(+)ESI-MS m/z: 550 (M+Na)+

(66) Methyl 4'-[2-[N-(tert-butoxycarbonyl)-N-[(2R)-2-(3-chlorophenyl)-2-hydroxyethyl]amino]ethyl]-3-chloro-1,1'-biphenyl-4-carboxylate
(+)ESI-MS m/z: 566 (M+Na)+

(67) Methyl 4'-[2-[N-(tert-butoxycarbonyl)-N-[(2R)-2-(3-chlorophenyl)-2-hydroxyethyl]amino]ethyl]-2'-methoxy-1,1'-biphenyl-4-carboxylate
(+)ESI-MS m/z: 540 (M+H)+

(68) Methyl 4'-[2-[N-(tert-butoxycarbonyl)-N-[(2R)-2-(3-chlorophenyl)-2-hydroxyethyl]amino]ethyl]-2'-chloro-1,1'-biphenyl-4-carboxylate
(+)ESI-MS m/z: 544 (M+H)+

(69) tert-Butyl N-[(2R)-2-(3-chlorophenyl)-2-hydroxyethyl]-N-[2-[4'-formyl-3'-(1-piperidinyl)-1,1'-biphenyl-4-yl]ethyl]carbamate
(+)ESI-MS m/z: 563 (M+H)+

(70) Methyl 4'-[3-[N-(tert-butoxycarbonyl)-N-[(2R)-2-(3-chlorophenyl)-2-hydroxyethyl]amino]propyl]-1,1'-biphenyl-4-carboxylate
MS (m/z): 524 (M+H)

(71) Ethyl 4'-[3-[N-(tert-butoxycarbonyl)-N-[(2R)-2-(3-chlorophenyl)-2-hydroxyethyl]amino]propyl]-1,1'-biphenyl-3-carboxylate
MS (m/z): 538 (M+H)

(72) Methyl 4'-[3-[N-(tert-butoxycarbonyl)-N-[(2R)-2-(3-chlorophenyl)-2-hydroxyethyl]amino]propyl]-3-fluoro-1,1'-biphenyl-4-carboxylate
MS (m/z): 542 (M+H)

(73) Methyl 4'-[3-[N-(tert-butoxycarbonyl)-N-[(2R)-2-(3-chlorophenyl)-2-hydroxyethyl]amino]propyl]-3-methoxy-1,1'-biphenyl-4-carboxylate
MS (m/z): 554 (M+H)

(74) Methyl 4'-[3-[N-(tert-butoxycarbonyl)-N-[(2R)-2-(3-chlorophenyl)-2-hydroxyethyl]amino]propyl]-3-chloro-1,1'-biphenyl-4-carboxylate
MS (m/z): 558 (M+H)

(75) Methyl 4'-[3-[N-(tert-butoxycarbonyl)-N-[(2R)-2-(3-chlorophenyl)-2-hydroxyethyl]amino]propyl]-3-methyl-1,1'-biphenyl-4-carboxylate
MS (m/z): 538 (M+H)

(76) Methyl 3'-[3-[N-(tert-butoxycarbonyl)-N-[(2R)-2-(3-chlorophenyl)-2-hydroxyethyl]amino]propyl]-1,1'-biphenyl-4-carboxylate
MS (m/z): 523 (M+H)

(77) Ethyl 3'-[3-[N-(tert-butoxycarbonyl)-N-[(2R)-2-(3-chlorophenyl)-2-hydroxyethyl]amino]propyl]-1,1'-biphenyl-3-carboxylate
MS (m/z): 538 (M+H)

(78) Methyl 4'-[2-[N-(tert-butoxycarbonyl)-N-[(2R)-2-(5-chloro-3-pyridyl)-2-hydroxyethyl]amino]ethyl]-1,1'-biphenyl-4-carboxylate
MS (m/z): 511 (M+H)

(79) tert-Butyl N-[(2R)-2-(6-chloro-3-pyridyl)-2-hydroxyethyl]-N-[(1R)-2-(4'-formyl-3'-phenoxy-1,1'-biphenyl-4-yl)-1-methylethyl]carbamate
MS (m/z): 587 (M+H)

(80) tert-Butyl N-[2-(4'-formyl-3'-phenoxy-1,1'-biphenyl-4-yl)ethyl]-N-[(2R)-2-hydroxy-2-(3-pyridyl)ethyl]-carbamate
MS (m/z): 539 (M+H)

(81) Methyl [4'-[2-[N-(tert-butoxycarbonyl)-N-[(2R)-2-(3-chlorophenyl)-2-hydroxyethyl]amino)ethyl]-1,1'-biphenyl-4-yl]acetate
MS (m/z) 524 (M+H)

(82) Methyl [4'-[2-[N-(tert-butoxycarbonyl)-N-[(2R)-2-(3-chlorophenyl)-2-hydroxyethyl]amino]ethyl]-1,1'-biphenyl-3-yl]acetate
MS (m/z): 524 (M+H)

(83) Methyl 4-[4-[(2R)-2-[N-(tert-butoxycarbonyl)-N-[(2R)-2-(6-chloro-3-pyridyl)-2-hydroxyethyl]amino]propyl]-phenyl]-1-naphthoate
MS (m/z): 575 (M+H)

(84) tert-Butyl N-[(1R)-2-[4'-[(benzoylamino)sulfonyl]-1,1'-biphenyl-4-yl]-1-methylethyl]-N-[(2R)-2-(6-chloro-3-pyridyl)-2-hydroxyethyl]carbamate
MS (m/z): 650 (M+H)

(85) tert-Butyl N-[2-[4'-formyl-3'-(1-piperidinyl)-1,1'-biphenyl-4-yl]ethyl]-N-[(2R)-2-hydroxy-2-phenylethyl]₇ carbamate
MS (m/z): 529 (M+H)

(86) 4'-[2-[[(2R)-2-(3-Chlorophenyl)-2-hydroxyethyl]amino]-ethyl]-3-(2-methoxyethoxy)-1,1'-biphenyl-4-carboxylic acid hydrochloride
MS (m/z): 470 (M+H)

(87) 3-(2-Ethoxyethoxy)-4'-[2-[[(2R)-(3-chlorophenyl)-2-hydroxyethyl]amino]ethyl]-1,1'-biphenyl-4-carboxylic acid hydrochloride
MS (m/z): 484 (M+H)

(88) 4'-[2-[[(2R)-2-(3-Chlorophenyl)-2-hydroxyethyl]amino]-ethyl]-3-propyl-1,1'-biphenyl-4-carboxylic acid hydrochloride
MS (m/z): 438 (M+H)

(89) 4'-[2-[[(2R)-2-(3-Chlorophenyl)-2-hydroxyethyl]amino]-ethyl]-3-propoxy-1,1'-biphenyl-4-carboxylic acid hydrochloride
MS (m/z): 454 (M+H)

(90) 4'-[2-[[(2R)-2-Hydroxy-2-phenylethyl]amino]ethyl]-3-(2-methoxyethoxy)-1,1'-biphenyl-4-carboxylic acid hydrochloride
NMR (DMSO-$d_6$, δ): 2.8-3.0 (6H, m), 3.32 (3H, s), 3.70 (2H, m), 4.29 (2H, m), 4.8-5.0 (1H, m), 6.33 (1H, m), 7.0-7.9 (12H, m) MS m/z: 436 (M+H)

(91) 3-(2-Ethoxyethoxy)-4'-[2-[[(2R)-2-hydroxy-2-phenylethyl]amino]ethyl]-1,1'-biphenyl-4-carboxylic acid hydrochloride
MS m/z: 450 (M+H)

(92) 3-[2-(Dimethylamino)ethoxy]-4'-[2-[[(2R)-2-hydroxy-2-phenylethyl]amino]ethyl]-1,1'-biphenyl-4-carboxylic acid dihydrochloride
NMR (DMSO-$d_6$, δ): 1.12 (3H, d, J=6.5 Hz), 2.8-3.6 (7H, m), 2.88 (6H, s), 4.58 (2H, m), 4.8-5.0 (1H, m), 6.33 (1H, m), 7.0-7.9 (12H, m) MS m/z: 462 (M+H)

(93) 4'-[2-[[(1S,2R)-2-Hydroxy-2-(4-hydroxyphenyl)-1-methylethyl]amino]ethyl]-3-isopropoxy-1,1'-biphenyl-4-carboxylic acid hydrochloride
NMR (DMSO-$d_6$, δ): 0.98 (3H, d, J=6.6 Hz), 1.31 (6H, d, J=6.0 Hz), 2.8-3.5 (5H, m), 4.79 (1H, q, J=6.0 Hz), 5.0-5.2 (1H, m), 6.0 (1H, m), 6.7-7.9 (11H, m) MS m/z: 450 (M+H)

EXAMPLE 33

To the mixture of 4'-[2-[[(2R)-2-phenyl-2-hydroxyethyl]amino]ethyl]-1,1'-biphenyl-4-nitrile (100 mg) in DMF (N,N-dimethylformamide) (10 ml) were added sodium azide (30 mg) and ammonium chloride (30 mg), and stirred at 120° C. for 12 hours. The resulting mixture was poured into a mixture of ethyl acetate and water, and the organic layer was washed with brine. After the solvent was evaporated under pressure, the residue was purified by column chromatography on silica gel to give the corresponding tetrazole. The obtained tetrazole was diluted with 6N hydrogen chloride in 1,4-dioxane (10 ml)

and the mixture was allowed to keep at the room temperature for 4 hours. The mixture was evaporated under reduced pressure and the obtained solid was washed with ether to give (1R)-2-[[(1R)-1-methyl-2-[4'-(1H-tetrazol-5-yl)-1,1'-biphenyl-4-yl]ethyl]amino]-1-phenylethanol hydrochloride (25 mg).

NMR (DMSO-$d_6$, δ): 1.14(3H, d, J=6.4 Hz), 2.6-3.2(5H, m), 3.93(2H, d, J=6.6 Hz), 4.9-5.1(1H, m), 6.24(1H, m), 7.2-7.5(7H, m), 7.77(2H, d, J=8.0 Hz), 7.94(2H, d, J=8.0 Hz), 8.15(2H, d, J=8.0 Hz) MS m/z: 400 (M+H)

EXAMPLE 34

The following compounds were obtained according to a similar manner to that of Example 30.

(1) 4'-[3-[N-(tert-Butoxycarbonyl)-N-[(2R)-2-(3-chlorophenyl)-2-hydroxyethyl]amino]propyl]-1,1'-biphenyl-4-carboxylic acid
MS (m/z): 510 (M+H)

(2) 4'-[3-[N-(tert-Butoxycarbonyl)-N-[(2R)-2-(3-chlorophenyl)-2-hydroxyethyl]amino]propyl]-1,1'-biphenyl-3-carboxylic acid
MS (m/z): 510 (M+H)

(3) 4'-[3-[N-(tert-Butoxycarbonyl)-N-[(2R)-2-(3-chlorophenyl)-2-hydroxyethyl]amino]propyl]-3-fluoro-1,1'-biphenyl-4-carboxylic acid
MS (m/z): 528 (M+H)

(4) 4'-[3-[N-(tert-Butoxycarbonyl)-N-[(2R)-2-(3-chlorophenyl)-2-hydroxyethyl]amino]propyl]-3-methoxy-1,1'-biphenyl-4-carboxylic acid
MS (m/z): 540 (M+H)

(5) 4'-[3-[N-(tert-Butoxycarbonyl)-N-[(2R)-2-(3-chlorophenyl)-2-hydroxyethyl]amino]propyl]-3-chloro-1,1'-biphenyl-4-carboxylic acid
MS (m/z): 544 (M+H)

(6) 4'-[3-[N-(tert-Butoxycarbonyl)-N-[(2R)-2-(3-chlorophenyl)-2-hydroxyethyl]amino]propyl]-3-methyl-1,1'-biphenyl-4-carboxylic acid
MS (m/z): 524 (M+H)

(7) 3'-[3-[N-(tert-Butoxycarbonyl)-N-[(2R)-2-(3-chlorophenyl)-2-hydroxyethyl]amino]propyl]-1,1'-biphenyl-4-carboxylic acid
MS (m/z): 523 (M+H)

(8) 3'-[3-[N-(tert-Butoxycarbonyl)-N-[(2R)-2-(3-chlorophenyl)-2-hydroxyethyl]amino]propyl]-1,1'-biphenyl-3-carboxylic acid
MS (m/z): 510 (M+H)

(9) [4'-[(2R)-2-[N-(tert-Butoxycarbonyl)-N-[(2R)-2-(3-chlorophenyl)-2-hydroxyethyl]amino]propyl]-1,1'-biphenyl-4-yl]acetic acid
MS (m/z): 524 (M+H)

(10) 4'-[2-[N-(tert-Butoxycarbonyl)-N-[(2R)-2-(5-chloro-3-pyridyl)-2-hydroxyethyl]amino]ethyl]-1,1'-biphenyl-4-carboxylic acid
MS (m/z): 497 (M+H)

(11) [4'-[2-[N-(tert-Butoxycarbonyl)-N-[(2R)-2-(3-chlorophenyl)-2-hydroxyethyl]amino]ethyl]-1,1'-biphenyl-4-yl]acetic acid
MS (m/z): 510 (M+H)

(12) 4-[4-[N-(2R)-2-[N-(tert-Butoxycarbonyl)-N-[(2R)-2-(6-chloro-3-pyridyl)-2-hydroxyethyl]amino]propyl]phenyl]-1-naphthoic acid
MS (m/z): 561 (M+H)

EXAMPLE 35

The following compounds were obtained according to a similar manner to that of Example 27.

(1) 4'-[3-[[(2R)-2-(3-Chlorophenyl)-2-hydroxyethyl]amino]-propyl]-1,1'-biphenyl-4-carboxylic acid hydrochloride
NMR (DMSO-$d_6$, δ): 1.70-2.10(2H, m), 2.60-3.40(6H, m), 4.90-5.10(1H, m), 7.40-7.60(6H, m), 7.70-7.90(4H, m), 8.10 (1H, d, J=8 Hz) MS (m/z): 410 (M+H)

(2) 4'-[3-[[(2R)-2-(3-Chlorophenyl)-2-hydroxyethyl]-amino]propyl]-1,1'-biphenyl-3-carboxylic acid hydrochloride
NMR (DMSO-$d_6$, δ): 1.80-2.10(2H, m), 2.60-3.40(6H, m), 4.90-5.10(1H, m), 7.30-7.60(9H, m), 7.80-7.90(1H, m), 8.10 (1H, s) MS (m/z): 410 (M+H)

(3) 4'-[3-[[(2R)-2-(3-Chlorophenyl)-2-hydroxyethyl]amino]-propyl]-3-fluoro-1,1'-biphenyl-4-carboxylic acid hydrochloride
NMR (DMSO-$d_6$, δ): 1.80-2.10(2H, m), 2.60-3.40(6H, m), 4.90-5.10(1H, m), 7.30-7.80(10H, m), 8.00(1H, t, J=8 Hz) MS (m/z): 428 (M+H)

(4) 4'-[3-[[(2R)-2-(3-Chlorophenyl)-2-hydroxyethyl]amino]-propyl]-3-methoxy-1,1'-biphenyl-4-carboxylic acid hydrochloride
NMR (DMSO-$d_6$, δ): 1.80-2.10(2H, m), 2.60-3.40(0.6H, m), 4.00(3H, s), 4.90-5.10(1H, m), 7.30-7.50(8H, m), 7.70-7.80(3H, m) MS (m/z): 440 (M+H)

(5) 3-Chloro-4'-[3-[[(2R)-2-(3-chlorophenyl)-2-hydroxyethyl]amino]propyl]-1,1'-biphenyl-4-carboxylic acid hydrochloride
NMR (DMSO-$d_6$, δ): 1.80-2.10(2H, m), 2.60-3.40(6H, m), 4.90-5.10(1H, m), 7.30-7.60(6H, m), 7.70-7.90(5H, m) MS (m/z): 444 (M+H)

(6) 4'-[3-[[(2R)-2-(3-Chlorophenyl)-2-hydroxyethyl]amino]-propyl]-3-methyl-1,1'-biphenyl-4-carboxylic acid hydrochloride
NMR (DMSO-$d_6$, δ): 1.80-2.10(2H, m), 2.60(3H, s), 2.60-3.40(6H, m), 4.90-5.10(1H, m), 7.30-7.60(10H, m), 7.90(1H, s) MS (m/z): 424 (M+H)

(7) 3'-[3-[[(2R)-2-(3-Chlorophenyl)-2-hydroxyethyl]amino]-propyl]-1,1'-biphenyl-4-carboxylic acid hydrochloride
NMR (DMSO-$d_6$, δ): 1.80-2.10(2H, m), 2.60-3.40(6H, m), 4.90-5.10(1H, m), 7.30-7.60(8H, m), 7.80(2H, d, J=8 Hz), 8.10(2H, d, J=8 Hz) MS (m/z): 410 (M+H)

(8) 3'-[3-[[(2R)-2-(3-Chlorophenyl)-2-hydroxyethyl]amino]-propyl]-1,1'-biphenyl-3-carboxylic acid hydrochloride
NMR (DMSO-$d_6$, δ): 1.80-2.10(2H, m), 2.60-3.40(6H, m), 4.90-5.10(1H, m), 7.30-7.60(9H, m), 7.80-7.90(2H, m), 8.20 (1H, s) MS (m/z): 410 (M+H)

(9) [4'-[(2R)-2-[[(2R)-2-(3-Chlorophenyl)-2-hydroxyethyl]-amino]propyl]-1,1'-biphenyl-4-yl]acetic acid hydrochloride
NMR (DMSO-$d_6$, δ): 1.05(3H, d, J=6 Hz), 2.80-3.60(7H, m), 5.00-5.15(1H, m), 7.20-7.70(12H, m) MS (m/z): 424 (M+H)

(10) 4'-[2-[[(2R)-2-(5-Chloro-3-pyridyl)-2-hydroxyethyl]-amino]ethyl]-1,1'-biphenyl-4-carboxylic acid dihydrochloride
NMR (DMSO-$d_6$, δ): 3.10-3.40(6H, m), 5.00-5.10(1H, m), 7.40-8.10(9H, m), 7.70-7.80(2H, m) MS (m/z): 397 (M+H)

(11) 4'-[(2R)-2-[[(2R)-2-Hydroxy-2-(3-pyridyl)ethyl]-amino]propyl]-3-phenoxy-1,1'-biphenyl-4-carboxylic acid dihydrochloride NMR (DMSO-$d_6$, δ): 1.13(3H, d, J=6 Hz), 2.70-2.80(1H, m), 2.80-3.60(4H, m), 5.30-5.40(1H, m), 6.90-7.60(7H, m), 7.90-8.00(2H, m), 8.50-8.60(1H, m), 8.80-8.90(2H, m) MS (m/z): 469 (M+H)

(12) 4'-[2-[[(2R)-2-Hydroxy-2-(3-pyridyl)ethyl]amino]-ethyl]-3-phenoxy-1,1'-biphenyl-4-carboxylic acid dihydrochloride NMR (DMSO-$d_6$, δ): 3.00-3.50(6H, m), 5.20-5.30(1H, m), 7.00-7.70(7H, m), 7.90-8.00(2H, m), 8.40-8.50(1H, m), 8.80-8.90(2H, m) MS (m/z): 455 (M+H)

(13) [4'-[2-[[(2R)-2-(3-Chlorophenyl)-2-hydroxyethyl]amino]-ethyl]-1,1'-biphenyl-4-yl)acetic acid hydrochloride NMR (DMSO-$d_6$, δ): 2.90-3.40(6H, m), 3.62(2H, s), 4.90-5.10(1H, m), 7.30-7.70(12H, m) MS (m/z): 410 (M+H)

(14) N-Benzoyl-4'-[(2R)-2-[[(2R)-2-hydroxy-2-(3-pyridyl)-ethyl]amino]propyl]-1,1'-biphenyl-4-sulfonamide dihydrochloride NMR (DMSO-$d_6$, δ): 1.01(3H, d, J=6 Hz), 2.60-3.60(5H, m), 5.00-5.15(1H, m), 7.20-8.10(13H, m), 8.30-8.40(1H, m), 8.70-8.80(2H, m) MS (m/z): 516 (M+H)

(15) 4'-[2-[[(2R)-2-Hydroxy-2-phenylethyl]amino]ethyl]-3-(1-piperidinyl)-1,1'-biphenyl-4-carboxylic acid dihydrochloride NMR (DMSO-$d_6$, δ): 1.50-1.80(6H, d, m), 3.00-3.40(10H, m), 5.00-5.10(1H, m), 7.20-7.50(7H, m), 7.70-7.80(3H, m), 8.10-8.20(2H, m) MS (m/z): 445 (M+H)

EXAMPLE 36

The following compounds were obtained according to a similar manner to that of Example 21.
(1) Methyl 4'-[2-[[(2R)-2-(6-chloro-3-pyridyl)-2-hydroxyethyl]amino]ethyl]-1,1'-biphenyl-4-carboxylate
MS (m/z): 410 (M+H)
(2) Methyl [4'-[(2R)-2-[[(2R)-2-(3-chlorophenyl)-2-hydroxyethyl]amino]propyl]-1,1'-biphenyl-4-yl]acetate
MS (m/z) 438 (M+H)
(3) Ethyl 5-[4-[(2R)-2-[[(2R)-2-(6-chloro-3-pyridyl)-2-hydroxyethyl]amino]propyl]phenyl}-1-naphthoate
MS (m/z): 489 (M+H)
(4) Methyl 4'-[2-[[(2R)-2-(4-chlorophenyl)-2-hydroxyethyl]amino]ethyl]-1,1'-biphenyl-4-carboxylate
MS (m/z): 410 (M+H)
(5) Ethyl 6-[4-[2-[N-benzyl-N-[(2R)-2-(3-chlorophenyl)-2-hydroxyethyl]amino]ethyl]phenyl]nicotinate
(+)ESI-MS m/z: 515 (M+H)$^+$
(6) Methyl 4'-[2-[N-benzyl-N-[(2R)-2-(3-chlorophenyl)-2-hydroxyethyl]amino]ethyl]-2,6-dimethyl-1,1'-biphenyl-4-carboxylate
(+)ESI-MS m/z: 528(M+H)$^+$

EXAMPLE 37

Under nitrogen to a solution of methyl 4'-[2-[[(2R)-2-(6-chloro-3-pyridyl)-2-hydroxyethyl]amino]ethyl]-1,1'-biphenyl-4-carboxylate (110 mg) in tetrahydrofran (10 ml) was added 1M methylzinc chloride in tetrahydrofran (0.8 ml) and tetrakis(triphenylphosphine)palladium (15.5 mg) at room temperature. The mixture was stirred at 80° C. for 24 hours, and then poured into an aqueous solution (60 ml) of ethylenediaminetetraacetic acid (1 g). The resulting mixture was neutralized with saturated aqueous sodium bicarbonate and extracted with ethyl acetate. The organic layer was washed with brine, dried over anhydrous magnesium sulfate and evaporated under reduced pressure. The residue was purified by column chromatography on silica gel (chloroform:methanol=100:1) to give methyl 4'-[2-[[(2R)-2-hydroxy-2-(6-methyl-3-pyridyl)ethyl]amino]ethyl]-1,1'-biphenyl-4-carboxylate (41 mg) as a colorless oil.

MS (m/z): 391 (M+H)

EXAMPLE 38

The following compounds were obtained by alkaline hydrolysis of each ester thereof in a conventional manner.
(1) Sodium 4'-[2-[[(2R)-2-hydroxy-2-(6-methyl-3-pyridyl) ethyl]amino]ethyl]-1,1'-biphenyl-4-carboxylate NMR (DMSO-$d_6$, δ): 2.50(3H, s), 2.60-2.90(6H, m), 4.60-4.70(1H, m), 7.10-7.40(3H, m), 7.50-7.70(5H, m), 7.90(1H, d, J=8 Hz), 8.40(1H, s)
(2) Sodium 4'-[2-[[(2R)-2-(6-chloro-3-pyridyl)-2-hydroxyethyl]amino]ethyl]-1,1'-biphenyl-4-carboxylate NMR (DMSO-$d_6$, δ): 2.80-3.80(6H, m), 4.90(1H, t, J=6 Hz), 7.10-7.90(8H, m), 7.98(2H, d, J=8 Hz), 8.30(1H, d, J=2 Hz) MS (m/z): 397 (M+H)
(3) Sodium 4'-[2-[[(2R)-2-(4-chlorophenyl)-2-hydroxyethyl] amino]ethyl]-1,1'-biphenyl-4-carboxylate NMR (DMSO-$d_6$, δ): 2.70-3.50(6H, m), 4.50-4.60(1H, m), 7.10-7.60(8H, m), 7.94(2H, d, J=8 Hz) MS (m/z): 396 (M+H)

EXAMPLE 39

The following compounds were obtained according to a similar manner to that of Preparation 29.
(1) Methyl [4'-[(2R)-2-[N-(tert-butoxycarbonyl)-N-[(2R)-2—(3-chlorophenyl)-2-hydroxyethyl]amino]propyl]-1,1'-biphenyl-4-yl]acetate
MS (m/z): 538 (M+H)
(2) Ethyl 5-[4-[(2R)-2-[N-(tert-butoxycarbonyl)-N-[(2R)-2-(6-chloro-3-pyridyl)-2-hydroxyethyl]amino]propyl]-phenyl]-1-naphthoate
MS (m/z): 589 (M+H)

EXAMPLE 40

The following compounds were obtained according to a similar manner to that of Example 18.
(1) [4'-[2-[[(2R)-2-(3-Chlorophenyl)-2-hydroxyethyl] amino]-ethyl]-1,1'-biphenyl-3-yl]acetic acid hydrochloride NMR (DMSO-$d_6$, δ): 2.80-3.40(6H, m), 3.65(2H, s), 4.90-5.10(1H, m), 7.20-7.70(12H, m) MS (m/z): 408 (M−H)
(2) 4'-[2-[[(2R)-2-(3-Chlorophenyl)-2-hydroxyethyl] amino]-ethyl]-1,1'-biphenyl-3-carboxylic acid hydrochloride NMR (DMSO-$d_6$, δ): 3.01-3.29(6H, m), 4.97-5.02(1H, m), 6.34(1H, br), 6.90(1H, m), 7.71-7.48(9H, m), 7.89-7.95(2H, m), 8.18(1H, d, J=1.5 Hz), 8.96(1H, br) (−)ESI-MS m/z: 394 (M−HCl−H)$^-$
(3) 3-[2-[[(2R)-2-(3-Chlorophenyl)-2-hydroxyethyl]amino]-ethyl]-6H-benzo[c]chromene-8-carboxylic acid hydrochloride NMR (DMSO-$d_6$, δ): 3.00-3.28(6H, m), 4.96-5.01(1H, m), 5.20(2H, s), 6.34(1H, br), 6.94-7.03(2H, m), 7.34-7.47(4H, m), 7.86-7.94(4H, m), 8.94(1H, br) (−)ESI-MS m/z: 422 (M−HCl−H)$^-$ (4) 2-[2-[[(2R)-2-(3-Chlorophenyl)-2-hydroxyethyl]amino]-ethyl]-6H-benzo[c]chromene-8-carboxylic acid hydrochloride NMR (DMSO-$d_6$, δ): 3.00-3.26(6H, m), 5.03-5.07(1H, m), 5.19(2H, s), 6.38(1H, br), 6.99(1H, d, J=8.2 Hz), 7.20-7.25 (2H, m), 7.35-7.48(4H, m), 7.85-7.98(4H, m), 9.10(1H, br) (−)ESI-MS m/z: 422 (M−HCl−H)⁻

(5) 6-[4-[2-[[(2R)-2-(3-Chlorophenyl)-2-hydroxyethyl]-amino]ethyl]phenyl]nicotinic acid hydrochloride NMR (DMSO-$d_6$, δ): 3.08-3.24(6H, m), 5.00-5.07(1H, br), 7.34-7.47(6H, m), 8.09-8.17 (3H, m), 8.31-8.38(1H, m), 8.98(1H, br), 9.12-9.16(1H, m), 9.30(1H, br) (−)ESI-MS m/z: 395 (M−HCl−H)⁻

(6) 3'-[2-[[(2R)-2-(3-Chlorophenyl)-2-hydroxyethyl]amino]-ethyl]-1,1'-biphenyl-4-carboxylic acid hydrochloride NMR (DMSO-$d_6$, δ): 3.01-3.28(6H, m), 4.97-5.02(1H, m), 6.34(1H, br), 7.34-7.48(6H, m), 7.62-7.65(2H, m), 7.78-7.83 (2H, m), 8.01-8.05(2H, m), 8.96(1H, br) (−)ESI-MS m/z: 394 (M−HCl−H)⁻

(7) 4'-[2-[[(2R)-2-(3-Chlorophenyl)-2-hydroxyethyl]amino]-ethyl]-2-fluoro-1,1'-biphenyl-4-carboxylic acid hydrochloride NMR (DMSO-$d_6$, δ): 3.01-3.28(6H, m), 5.02-5.05(1H, m), 6.38(1H, br), 7.37-7.87(11H, m), 9.10(1H, br) (−)ESI-MS m/z: 412 (M−HCl−H)⁻

(8) 4'-[2-[[(2R)-2-(3-Chlorophenyl)-2-hydroxyethyl]amino]-ethyl]-2,6-dimethyl-1,1'-biphenyl-4-carboxylic acid hydrochloride NMR (DMSO-$d_6$, δ): 2.00(6H, m), 3.06-3.11(6H, m), 4.98-5.04(1H, m), 6.36-6.85(1H, br), 7.11-7.15(2H, m), 7.35-7.49(6H, m), 7.70-7.72(2H, m), 9.06(1H, br) (−)ESI-MS m/z: 422 (M−HCl−H)⁻

(9) 3-Chloro-4'-[2-[[(2R)-2-(3-chlorophenyl)-2-hydroxyethyl]amino]ethyl]-1,1'-biphenyl-4-carboxylic acid hydrochloride NMR (DMSO-$d_6$, δ): 3.01-3.28(6H, m), 5.00-5.04(1H, m), 6.36(1H, br), 7.35-7.47(6H, m), 7.70-7.91(5H, m), 9.07(1H, br) (−)ESI-MS m/z: 428 (M−HCl−H)⁻

(10) 4'-[2-[[(2R)-2-(3-Chlorophenyl)-2-hydroxyethyl]amino]-ethyl]-2'-methoxy-1,1'-biphenyl-4-carboxylic acid hydrochloride NMR (DMSO-$d_6$, δ): 3.03-3.27(6H, m), 3.80(3H, s), 5.03-5.07(1H, m), 6.38(1H, br), 6.96(1H, d, J=7.9 Hz), 7.06(1H, s), 7.29-7.48(5H, m), 7.58(1H, d, J=8.3 Hz), 7.96(1H, d, J=8.3 Hz), 9.13-9.18(1H, br) (−)ESI-MS m/z: 424 (M−HCl−H)⁻

(11) 2'-Chloro-4'-[2-[[(2R)-2-(3-chlorophenyl)-2-hydroxyethyl]amino]ethyl]-1,1'-biphenyl-4-carboxylic acid hydrochloride NMR (DMSO-$d_6$, δ): 3.00-3.27(6H, m), 5.01-5.07(1H, m), 6.37-6.39(1H, br), 6.96(1H, d, J=7.9 Hz), 7.34-7.57(9H, m), 8.04(2H, d, J=8.3 Hz), 9.04-9.30(1H, br) (−)ESI-MS m/z: 428 (M−HCl−H)⁻

(12) 4'-[2-[[(2R)-2-Hydroxy-2-phenylethyl]amino]ethyl]-3-(isopropylthio)-1,1'-biphenyl-4-carboxylic acid hydrochloride NMR (DMSO-$d_6$, δ): 1.31 (6H, d, J=6.5 Hz), 2.99-3.33 (6H, m), 3.69-3.82 (1H, m), 4.96-5.00 (1H, m), 6.22 (1H, m), 7.30-7.92 (12H, m) (−)ESI-MS m/z: 434 (M−HCl−H)⁻

(13) 4'-[2-[[(2R)-2-Hydroxy-2-phenylethyl]amino]ethyl]-3-(isopropylsulfonyl)-1,1'-biphenyl-4-carboxylic acid hydrochloride NMR (DMSO-$d_6$, δ): 1.25 (6H, d, J=6.8 Hz), 2.99-3.33 (6H, m), 3.94-4.08 (1H, m), 4.96-5.00 (1H, m), 6.22 (1H, m), 7.27-8.12 (12H, m) (−)ESI-MS m/z: 466 (M−HCl−H)⁻

EXAMPLE 41

The following compounds were obtained according to a similar manner to that of Example 14 followed by a similar manner to that of Example 18.

(1) 4'-[2-[[(2R)-2-Hydroxy-2-phenylethyl]amino]ethyl]-3-isobutyl-1,1'-biphenyl-4-carboxylic acid hydrochloride NMR (DMSO-$d_6$, δ): 0.89(6H, d, J=8 Hz), 1.80-2.00(1H, m), 2.90-3.40(8H, m), 4.90-5.10(1H, m), 7.30-7.80(12H, m) MS (m/z): 418 (M+H)

(2) 4'-[(2R)-2-[[(2R)-2-Hydroxy-2-phenylethyl]amino]-propyl]-3-isobutyl-1,1'-biphenyl-4-carboxylic acid hydrochloride NMR (DMSO-$d_6$, δ): 0.89(7H, d, J=6 Hz), 1.21(3H, d, J=6 Hz), 1.80-1.90(1H, m), 2.70-3.60(7H, m), 5.00-5.10(1H, m), 7.20-7.80(12H, m) MS (m/z): 432 (M+H)

(3) 4'-[2-[[(2R)-2-Hydroxy-2-phenylethyl]amino]ethyl]-3-isopropyl-1,1'-biphenyl-4-carboxylic acid hydrochloride NMR (DMSO-$d_6$, δ): 1.20(3H, d, J=7 Hz), 2.90-3.40(6H, m), 3.80-3.90(1H, m), 4.90-5.00(1H, m), 7.20-7.80(12H, m) MS (m/z): 404 (M+H)

(4) 4'-[2-[[(2R)-2-Hydroxy-2-phenylethyl]amino]ethyl]-3-phenyl-1,1'-biphenyl-4-carboxylic acid hydrochloride NMR (DMSO-$d_6$, δ): 2.90-3.40(6H, m), 4.95-5.10(1H, m), 7.30-7.80(17H, m) MS (m/z): 438 (M+H)

(5) 4'-[2-[[(2R)-2-Hydroxy-2-phenylethyl]amino]ethyl]-3-propyl-1,1'-biphenyl-4-carboxylic acid hydrochloride NMR (DMSO-$d_6$, δ): 0.90-1.05(3H, m), 1.50-1.70(2H, m), 2.80-3.40(8H, m), 4.90-5.05(1H, m), 7.20-7.80(12H, m) MS (m/z): 404 (M+H)

(6) 4'-[(2R)-2-[[(2R)-2-Hydroxy-2-phenylethyl]amino]-propyl]-3-propyl-1,1'-biphenyl-4-carboxylic acid hydrochloride NMR (DMSO-$d_6$, δ): 0.80-1.70(8H, m), 2.70-3.20(7H, m), 5.00-5.15(1H, m), 7.10-7.90(12H, m) MS (m/z): 418 (M+H)

(7) 4'-[(2R)-2-[[(2R)-2-Hydroxy-2-phenylethyl]amino]-propyl]-3-isopropyl-1,1'-biphenyl-4-carboxylic acid hydrochloride NMR (DMSO-$d_6$, δ): 1.05-1.10(9H, m), 2.05-2.15(1H, m), 2.80-3.60(5H, m), 5.00-5.15(1H, m), 7.20-7.80(12H, m) MS (m/z): 418 (M+H)

(8) 4'-[(2R)-2-[[(2R)-2-Hydroxy-2-(3-pyridyl)ethyl]-amino]propyl]-3-phenyl-1,1'-biphenyl-4-carboxylic acid dihydrochloride NMR (DMSO-$d_6$, δ): 1.15(3H, d, J=6 Hz), 2.80-2.90(1H, m), 3.20-3.60(4H, m), 5.10-5.20(1H, m), 7.30-7.90(13H, m), 8.30-8.40(1H, m), 8.70-8.90(2H, m) MS (m/z): 453 (M+H)

(9) 4'-[2-[[(2R)-2-Hydroxy-2-phenylethyl]amino]ethyl]-3-phenyl-1,1'-biphenyl-4-carboxylic acid hydrochloride NMR (DMSO-$d_6$, δ): 3.00-3.60(6H, m), 5.20-5.30(1H, m), 7.20-7.90(13H, m), 8.30-8.40(1H, m), 8.70-8.80(2H, m) MS (m/z): 439 (M+H)

EXAMPLE 42

The following compounds were obtained by conversion of an amino protective group from each corresponding amino protective group of benzyl in a conventional manner.

(1) Ethyl 6-[4-[2-[N-(tert-butoxycarbonyl)-N-[(2R)-2-(3-chlorophenyl)-2-hydroxyethyl]amino]ethyl]phenyl]-nicotinate (+)ESI-MS m/z: 547 (M+Na)⁺

(2) Methyl 4'-[2-[N-(tert-butoxycarbonyl)-N-[(2R)-2-(3-chlorophenyl)-2-hydroxyethyl]amino]ethyl]-2,6-dimethyl-1,1'-biphenyl-4-carboxylate (+)ESI-MS m/z: 560 (M+Na)⁺

EXAMPLE 43

The following compound was obtained according to a similar manner to that of Example 55.

tert-Butyl N-[(2R)-2-(3-chlorophenyl)-2-hydroxyethyl]-N-[2-(3'-hydroxy-1,1'-biphenyl-4-yl)ethyl]carbamate (+)ESI-MS m/z: 468 (M+H)$^+$

EXAMPLE 44

The following compound was obtained by a replacement reaction of the object compound of Example 43 with tert-butyl 2-bromoacetate in a conventional manner.

tert-Butyl [[4'-[2-[N-(tert-butoxycarbonyl)-N-[(2R)-2-(3-chlorophenyl)-2-hydroxyethyl]amino]ethyl]-1,1'-biphenyl-3-yl]oxy]acetate (+)ESI-MS m/z: 582 (M+H)$^+$

EXAMPLE 45

The following compound was obtained by elimination of two amino protective groups of the object compound of Example 44 in a conventional manner.

[[4'-[2-[[(2R)-2-(3-Chlorophenyl)-2-hydroxyethyl]-amino]ethyl]-1,1'-biphenyl-3-yl]oxy]acetic acid hydrochloride NMR (DMSO-d$_6$, δ): 3.00-3.27(6H, m), 4.76(2H, s), 5.01-5.05(1H, m), 6.36(1H, br), 6.90(1H, m), 7.15-7.48(9H, m), 7.64(2H, d, J=8.0 Hz), 9.09-9.21(1H, br) (−)ESI-MS m/z: 424 (M−HCl−H)$^−$

EXAMPLE 46

The following compound was obtained according to a similar manner to that of Preparation 61.

Methyl 4-bromo-3-[[4-[2-[N-(tert-butoxycarbonyl)-N-[(2R)-2-(3-chlorophenyl)-2-hydroxyethyl]amino]ethyl]-phenoxy]methyl]benzoate (+)ESI-MS m/z: 617, 619 (M+H)$^+$

EXAMPLE 47

The following compound was obtained according to a similar manner to that of Example 20.

tert-Butyl N-[(2R)-2-(3-chlorophenyl)-2-hydroxyethyl]-N-[2-[4'-formyl-3'-(1-piperidinyl)-1,1'-biphenyl-4-yl]ethyl]carbamate NMR (DMSO-d$_6$, δ): 1.71-2.00(6H, m), 3.09-3.20(6H, m), 3.47-3.59(4H, br), 5.06-5.10(1H, m), 7.28-7.48(6H, m), 7.82-7.89(3H, m), 8.12-8.21(2H, m) (−)ESI-MS m/z: 474 (M−HCl−H)$^−$

EXAMPLE 48

The following compound was obtained according to a similar manner to that of Preparation 28.

Methyl 3-[2-[N-(tert-butoxycarbonyl)-N-[(2R)-2-(3-chlorophenyl)-2-hydroxyethyl]amino]ethyl]-6H-benzo[c]chromene-8-carboxylate (+)ESI-MS m/z: 538 (M+H)$^+$

EXAMPLE 49

The following compound was obtained according to a similar manner to that of Preparation 62.

Methyl 2-[2-[N-(tert-butoxycarbonyl)-N-[(2R)-2-(3-chlorophenyl)-2-hydroxyethyl]amino]ethyl]-6H-benzo[c]chromene-8-carboxylate (+)ESI-MS m/z: 560 (M+Na)$^+$

EXAMPLE 50

The following compounds were obtained according to a similar manner to that of Example 1.

(1) 4'-[2-[N-(tert-Butoxycarbonyl)-N-[(2R)-2-hydroxy-2-(3-pyridyl)ethyl]amino]ethyl]-3-phenoxy-1,1'-biphenyl-4-carboxylic acid MS (m/z): 555 (M+H)

(2) 4'-[2-[N-(tert-Butoxycarbonyl)-N-[(2R)-2-hydroxy-2-phenylethyl]amino]ethyl]-3-(1-piperidinyl)-1,1'-biphenyl-4-carboxylic acid MS (m/z) 545 (M+H)

EXAMPLE 51

The following compound was obtained according to a similar manner to that of Example 1 followed by a similar manner to that of Example 25.

4'-[(2R)-2-[N-(tert-Butoxycarbonyl)-N-[(2R)-2-hydroxy-2-(3-pyridyl)ethyl]amino]propyl]-3-phenoxy-1,1'-biphenyl-4-carboxylic acid MS (m/z): 569 (M+H)

EXAMPLE 52

The following compound was obtained according to a similar manner to that of Example 25 followed by a similar manner to that of Example 18.

5-[4-[(2R)-2-[[(2R)-2-Hydroxy-2-(3-pyridyl)ethyl]-amino]propyl]phenyl]-1-naphthoic acid dihydrochloride MS (m/z): 426 (M+H)

EXAMPLE 53

The following compound was obtained according to a similar manner to that of Example 25 followed by a similar manner to that of Example 27.

4-[4-[(2R)-2-[[(2R)-2-Hydroxy-2-(3-pyridyl)ethyl]-amino]propyl]phenyl]-1-naphthoic acid dihydrochloride MS (m/z): 427 (M+H)

EXAMPLE 54

The following compound was obtained according to a similar manner to that of Example 25.

tert-Butyl N-[(1R)-2-[4'-[(benzoylamino)sulfonyl]-1,1'-biphenyl-4-yl]-1-methylethyl]-N-[(2R)-2-hydroxy-2-(3-pyridyl)ethyl]carbamate MS (m/z): 616 (M+H)

EXAMPLE 55

The following compound was obtained according to a similar manner to that of Example 7.

Methyl 4'-[2-[N-(tert-butoxycarbonyl)-N-[(2R)-2-hydroxy-2-pyenylethyl]amino]ethyl]-3-(isopropylthio)-1,1'-biphenyl-4-carboxylate (+)ESI-MS (m/z): 572 (M+Na)$^+$

EXAMPLE 56

To a solution of methyl 4'-[2-[N-(tert-butoxycarbonyl)-N-[(2R)-2-hydroxy-2-phenylethyl]amino]ethyl]-3-(isopropylthio)-1,1'-biphenyl-4-carboxylate (338 mg) in chloroform (8 ml) and N,N-dimethylformamide (4 ml) was added m-chloroperbenzoic acid (594 mg) at room temperature and the mixture was stirred at the same temperature for 1 hour. To the mixture was added water and extracted with dichloromethane. The organic layer was washed with brine, dried over magnesium sulfate and evaporated. The residue was purified by column chromatography on silica gel (hexane/ethyl acetate=2/1) to give methyl 4'-[2-[N-(tert-butoxycarbonyl)-N-[(2R)-2-hydroxy-2-phenylethyl]amino]-ethyl]-3-(isopropylsulfonyl)-1,1'-biphenyl-4-carboxylate (340 mg).

(+)ESI-MS m/z: 604 (M+Na)+

Preparation 71

To a solution of (2R)-N-benzyl-N-[2-(4-bromophenyl)-ethyl]-2-[[tert-butyl(dimethyl)silyl]oxy]-2-(3-chlorophenyl)ethanamine (2.1 g) in tetrahydrofuran (25 ml) was added a solution of butyllithium in hexane (1.59M, 2.83 ml) dropwise at −70° C. under nitrogen and the mixture was stirred at −70° C. for 30 minutes. To the reaction mixture was added 4-[[tert-butyl(dimethyl)silyl]oxy]benzaldehyde (977 mg) at −70° C., and the mixture was stirred at −70° C. for 1 hour. The mixture was allowed to warm to room temperature and partitioned between ethyl acetate and water. The organic layer was separated, washed with saturated sodium biscarbonate solution and brine, dried over magnesium sulfate and evaporated under reduced pressure. The residue was purified by column chromatography on silica gel (hexane/ethyl acetate=10/1) to give [4-[2-[N-benzyl-N-[(2R)-2-[[tert-butyl(dimethyl)silyl]oxy]-2-(3-chlorophenyl)-ethyl]amino]ethyl]phenyl][4-[[tert-butyl(dimethyl)silyl]-oxy]phenyl]methanol (1.1 g).

(+)ESI-MS m/z: 716 (M+H)+

Preparation 72

To a solution of (1R)-2-[[2-(4-bromophenyl)ethyl]-amino]-1-(3-chlorophenyl)ethanol (5.1 g) and imidazole (2.9 g) in N,N-dimethylformamide (30 ml) was added tert-butyl(dimethyl)silyl chloride (5.85 g) and the mixture was stirred at 40° C. for 24 hours. The mixture was partitioned between ethyl acetate and water. The organic layer was separated, washed with water, 5% acetic acid solution, saturated sodium biscarbonate solution and brine, dried over magnesium sulfate and evaporated under reduced pressure to give a crude product. To a solution of the product in tetrahydrofuran (80 ml) and triethylamine (2.0 ml) was added di-tert-butyl dicarbonate (3.14 g), and the mixture was stirred at room temperature for 3 hours. The mixture was partitioned between ethyl acetate and water. The organic layer was separated, washed with water and brine, dried over magnesium sulfate and evaporated under reduced pressure. The residue was purified by column chromatography on silica gel (hexane/ethyl acetate=20/1) to give tert-butyl N-[2-(4-bromophenyl)ethyl]-N-[(2R)-2-[[tert-butyl(dimethyl)silyl]oxy]-2-(3-chlorophenyl)ethyl]carbamate (5.0 g).

(+)ESI-MS m/z: 568 (M+H)+

Preparation 73

To a solution of tert-butyl N-[2-(4-bromophenyl)-ethyl]-N-[(2R)-2-[[tert-butyl(dimethyl)silyl]oxy]-2-(3-chlorophenyl)ethyl]carbamate (880 mg) in tetrahydrofuran (13 ml) was added a solution of butyllithium in hexane (1.59M, 1.07 ml) dropwise at −70° C. under nitrogen and the mixture was stirred at −70° C. for 30 minutes. To the reaction mixture was added 4-[[tert-butyl(dimethyl)silyl]oxy]-N-methoxy-N-methylbenzamide (480 mg) at −70° C., and the mixture was stirred at −70° C. for 1 hour. The mixture was allowed to warm to room temperature and partitioned between ethyl acetate and water. The organic layer was separated, washed with saturated sodium bicarbonate solution and brine, dried over magnesium sulfate and evaporated under reduced pressure. The residue was purified by column chromatography on silica gel (hexane/ethyl acetate=10/1) to give tert-butyl N-[2-[4-[4-[[tert-butyl(dimethyl)silyl]oxy]benzoyl]phenyl]ethyl]-N-[(2R)-2-[[tert-butyl(dimethyl)silyl]oxy]-2-(3-chlorophenyl)ethyl]carbamate (710 mg).

(+)ESI-MS m/z: 746 (M+Na)+

Preparation 74

Di-tert-butyl dicarbonate (2.18 g) was added to a solution of 2-(4-bromophenyl)ethanamine (2.0 g) in tetrahydrofuran (5 ml) under ice water cooling over 10 minutes and the mixture was stirred at room temperature for further 1 hour. The reaction mixture was evaporated in vacuo to give tert-butyl 2-(4-bromophenyl)ethylcarbamate (2.98 g) as a colorless foam.

NMR (CDCl$_3$, δ): 1.43 (9H, s), 2.75 (2H, t, J=8 Hz), 3.36 (2H, t, J=8 Hz), 7.00-7.10 (2H, m), 7.30-7.50 (2H, m)

Preparation 75

The following compound was obtained according to a similar manner to that of Preparation 3.

Methyl 4'-[2-[(tert-butoxycarbonyl)amino]ethyl]-1,1'-biphenyl-4-carboxylate

MS m/z: 356 (M+H)

Preparation 76

The following compound was obtained according to a similar manner to that of Example 4.

Methyl 4'-(2-aminoethyl)-1,1'-biphenyl-4-carboxylate hydrochloride

NMR (DMSO-d$_6$, δ): 2.80-3.10 (4H, m), 3.88 (3H, s), 7.40 (2H, d, J=8 Hz), 7.60-8.10 (6H, m)

Preparation 77

To a solution of methyl 4'-(2-aminoethyl)-1,1'-biphenyl-4-carboxylate hydrochloride (420 mg) and benzaldehyde (153 mg) in dichloromethane (5 ml) was stirred for 3 hours, and the mixture was evaporated in vacuo. To the residue in methanol (10 ml) was added sodium borohydride (65 mg) on ice cooling, and stirred at the same temperature for 1 hour. The resulting mixture was poured into saturated aqueous sodium bicarbonate solution, and extracted with ethyl acetate. The organic layer was washed with brine, dried over magnesium sulfate, and evaporated in vacuo. The residue was chromatographed (hexane-ethyl acetate) over silica gel to afford methyl 4'-[2-(benzylamino)ethyl]-1,1'-biphenyl-4-carboxylate (460 mg) as a colorless powder.

MS m/z: 346 (M+H)

Preparation 78

Under nitrogen at 4° C., to a solution of 2,2,2-trifluoro-N-[2-[4-[(4-methoxyphenyl)thio]phenyl]ethyl]-acetamide (1.5 g) in dichloromethane (15 ml) was added 1M boron tribromide in dichloromethane (10.5 ml), and the mixture was stirred at room temperature for 15 hours. The mixture was evaporated under reduced pressure. The residue was dissolved in a mixture of dichloromethane and saturated aqueous sodium bicarbonate. After separation, the organic layer was dried over magnesium sulfate and evaporated under reduced pressure to give 2,2,2-trifluoro-N-[2-[4-[(4-hydroxyphenyl)thio]phenyl]ethyl]acetamide (1.42 g).

(+)ESI-MS m/z: 364 (M+Na)+

Preparation 79

To a solution of 2,2,2-trifluoro-N-[2-[4-[(4-hydroxyphenyl)thio]phenyl]ethyl]acetamide (480 mg) in methanol (5.0 ml) was added 1N sodium hydroxide solution (2.8 ml). The mixture was refluxed for 12 hours. The mixture was evaporated under reduced pressure. The residue was dissolved in a mixture of dichloromethane (40 ml), 1N hydrochloric acid solution (2.0 ml) and water (15 ml). After separation, the organic layer was dried over magnesium sulfate and evaporated under reduced pressure to give 4-[[4-(2-aminoethyl)phenyl]thio]phenol (300 mg).

(−)ESI-MS m/z: 244 (M−H)⁻

Preparation 80

To a solution of (αS,βR)-4-hydroxynorephedrine (500 mg) and 4-bromophenylethyl bromide (500 mg) in N,N-dimethylformamide (5 ml) was added N,N-diiospropylethylamine (0.5 ml), and the mixture was stirred for 6 hours at 80° C. The mixture was partitioned between ethyl acetate and water. The organic layer was washed with brine, dried over magnesium sulfate, and concentrated in vacuo. The residual oil was diluted in tetrahydrofuran (10 ml). To the solution was added di-tert-butyl dicarbonate (1 g) at room temperature, and the mixture was stirred at the same temperature for 12 hours. The resulting mixture was evaporated under pressure and the residue was purified by column chromatography on silica gel to give 4-[2-[N-[(1S,2R)-2-hydroxy-2-(4-hydroxyphenyl)-1-methylethyl]-N-(tert-butyloxycarbonyl)amino]ethyl]phenyl bromide (520 mg).

MS m/z: 550 (M+H)

EXAMPLE 57

To a solution of (2R)-N-benzyl-N-[2-(4-bromophenyl)ethyl]-2-[[tert-butyl(dimethyl)silyl]oxy]-2-(3-chlorophenyl) ethanamine (850 mg) in 1,2-dimethoxyethane (9 ml) was added 4-[[tert-butyl(dimethyl)silyl]oxy]-phenylboronic acid (498 mg), tetrakis(triphenylphosphine)-palladium (88 mg) and aqueous solution of sodium carbonate (2M, 1.6 ml), and the mixture was stirred at 75° C. for 10 hours under nitrogen. The mixture was diluted with ethyl acetate and water. The organic layer was separated, washed with brine, dried over magnesium sulfate and evaporated. To a solution of the residue in tetrahydrofuran (10 ml) was added 1M tetrabutylammonium fluoride in tetrahydrofuran (3.6 ml), and the mixture was stirred at room temperature for 8 hours under nitrogen. The mixture was partitioned between ethyl acetate and water. The organic layer was separated, washed with water and brine, dried over magnesium sulfate and evaporated under reduced pressure. The residue was purified by column chromatography on silica gel (hexane/ethyl acetate=2/1) to give 4'-[2-[N-benzyl-N-[(2R)-2-(3-chlorophenyl)-2-hydroxyethyl]amino]ethyl]-1,1'-biphenyl-4-ol (540 mg).

(+)ESI-MS m/z: 458 (M+H)⁺

EXAMPLE 58

A mixture of 4'-[2-[N-benzyl-N-[(2R)-2-(3-chlorophenyl)-2-hydroxyethyl]amino]ethyl]-1,1'-biphenyl-4-ol (420 mg) in 4N hydrogen chloride in ethyl acetate (1.0 ml) was stirred for 5 minutes. The solvent was removed by evaporation. A suspension of the residue in ethanol (1.5 ml) and chlorobenzene (3.5 ml) was hydrogenated over palladium on carbon (10% w/w, 50% wet, 10 mg) under hydrogen atmosphere for 1 hour. The catalyst was filtered off, and the filtrate was evaporated. The residue was diluted with chloroform (40 ml) and methanol (5 ml). The organic layer was washed with saturated sodium biscarbonate solution and brine, dried over magnesium sulfate and evaporated under reduced pressure. To the residue was added tetrahydrofuran (3 ml) and di-tert-butyl dicarbonate (220 mg), and the mixture was stirred at room temperature for 12 hours. The mixture was partitioned between ethyl acetate and water. The organic layer was separated, washed with water and brine, dried over magnesium sulfate and evaporated under reduced pressure. The residue was purified by column chromatography on silica gel (hexane/ethyl acetate=2/1) to give tert-butyl (2R)-N-[2-(3-chlorophenyl)-2-hydroxyethyl]-N-[2-(4'-hydroxy-1,1'-biphenyl-4-yl)ethyl]carbamate (245 mg).

(+)ESI-MS m/z: 490 (M+Na)⁺

EXAMPLE 59

To a solution of tert-butyl (2R)-N-[2-(3-chlorophenyl)-2-hydroxyethyl]-N-[2-(4'-hydroxy-1,1'-biphenyl-4-yl)ethyl]carbamate (240 mg) and potassium carbonate (78 mg) in N,N-dimethylformamide (4 ml) was added tert-butyl bromoacetate (110 mg), and the mixture was stirred at room temperature for 3 hours. The mixture was partitioned between ethyl acetate and water. The organic layer was separated, washed with water and brine, dried over magnesium sulfate and evaporated under reduced pressure. The residue was purified by column chromatography on silica gel (hexane/ethyl acetate=3/1) to give tert-butyl [[4'-[2-[N-(tert-butoxycarbonyl)-N-[(2R)-2-(3-chlorophenyl)-2-hydroxyethyl]amino]ethyl]-1,1'-biphenyl-4-yl]oxy]acetate (245 mg).

(+)ESI-MS m/z: 582 (M+H)⁺

EXAMPLE 60

The following compounds were obtained according to a similar manner to that of Example 4.

(1) [[4'-[2-[[(2R)-2-(3-Chlorophenyl)-2-hydroxyethyl]amino]ethyl]-1,1'-biphenyl-4-yl]oxy]acetic acid hydrochloride NMR (DMSO-d₆, δ): 3.02-3.35 (6H, m), 4.72 (2H, s), 5.00-5.05 (1H, m), 6.37 (1H, br), 6.99 (2H, d, J=8.7 Hz), 7.30-7.61 (10H, m), 9.04 (1H, br), 13.03 (1H, br) (−)ESI-MS m/z: 424 (M−HCl−H)⁻

(2) [4-[4-[2-[[(2R)-2-(3-Chlorophenyl)-2-hydroxyethyl]amino]ethyl]benzoyl]phenoxy]acetic acid hydrochloride NMR (DMSO-d₆, δ): 3.01-3.32 (6H, m), 4.81 (2H, s), 4.96-5.00 (1H, m), 6.35 (1H, br), 7.07 (2H, d, J=8.8 Hz), 7.35-7.47 (6H, m), 7.66-7.75 (4H, m), 8.99 (1H, br) (−)ESI-MS m/z: 452 (M−HCl−H)⁻

EXAMPLE 61

To a solution of tert-butyl N-[2-(4-bromophenyl)ethyl]-N-[(2R)-2-(3-chlorophenyl)-2-hydroxyethyl]carbamate (435 mg) in 1,2-dimethoxyethane (6 ml) were added 4-methoxycarbonyl-phenyl boronic acid (224 mg), tetrakis(triphenylphosphine)-palladium (55 mg) and aqueous solution of sodium carbonate (2M, 1.0 ml), and the mixture was stirred at 80° C. for 2 hours under nitrogen. The mixture was diluted with ethyl acetate and water. The organic layer was separated, washed with brine, dried over magnesium sulfate and evaporated under reduced pressure. The residue was purified by column chromatography on silica gel (hexane/ethyl acetate=3/1) to give methyl 4'-[2-[N-(tert-butoxycarbonyl)-N-[(2R)-2-(3-chlorophenyl)-2-hydroxyethyl]amino]ethyl]-1,1'-biphenyl-4-carboxylate (400 mg).

(+)ESI-MS m/z: 510 (M+H)⁺

EXAMPLE 62

The following compound was obtained according to a similar manner to that of Example 6.

4'-[2-[[(2R)-2-(3-Chlorophenyl)-2-hydroxyethyl]amino]-ethyl]-1,1'-biphenyl-4-carboxylic acid hydrochloride NMR (DMSO-$d_6$, δ): 3.01-3.27 (6H, m), 5.01-5.06 (1H, m), 6.36 (1H, br), 7.34-7.48 (6H, m), 7.70-7.81 (6H, m), 8.02 (2H, d, J=8.4 Hz), 9.11 (1H, br) (−)ESI-MS m/z: 394 (M−HCl−H)$^-$

EXAMPLE 63

To a solution of [4-[2-[N-benzyl-N-[(2R)-2-[[tert-butyl(dimethyl)silyl]oxy]-2-(3-chlorophenyl)ethyl]amino]-ethyl]phenyl][4-[[tert-butyl(dimethyl)silyl]oxy]phenyl]-methanol (1.1 g) in tetrahydrofuran (15 ml) was added 1M tetrabutylammonium fluoride in tetrahydrofuran (5.0 ml) at 0° C., and the mixture was stirred at room temperature for 24 hours under nitrogen. The mixture was partitioned between ethyl acetate and water. The organic layer was separated, washed with water and brine, dried over magnesium sulfate and evaporated under reduced pressure. The residue was purified by column chromatography on silica gel (hexane/ethyl acetate=2/1) to give 4-[[4-[2-[N-benzyl-N-[(2R)-2-(3-chlorophenyl)-2-hydroxyethyl]amino]ethyl]-phenyl](hydroxy)methyl]phenol (550 mg).

(+)ESI-MS m/z: 486 (M−H)$^-$

EXAMPLE 64

A mixture of 4-[[4-[2-[N-benzyl-N-[(2R)-2-(3-chlorophenyl)-2-hydroxyethyl]amino]ethyl]phenyl](hydroxy)-methyl]phenol (545 mg) in 4N hydrogen chloride in 1,4-dioxane (1.0 ml) was stirred for 5 minutes. The solvent was removed by evaporation. A suspension of the residue in ethanol (2.2 ml) and chlorobenzene (5.2 ml) was hydrogenated over palladium on carbon (10% w/w, 50% wet, 55 mg) under hydrogen atmosphere for 2 hours. The catalyst was filtered off, and the filtrate was evaporated. The residue was diluted with ethyl acetate and saturated sodium biscarbonate solution. The organic layer was separated, washed with brine, dried over magnesium sulfate and evaporated under reduced pressure to give 4-[4-[2-[[(2R)-2-(3-chlorophenyl)-2-hydroxyethyl]amino]ethyl]benzyl]phenol (395 mg).

(+)ESI-MS m/z: 382 (M+H)$^+$

EXAMPLE 65

To a solution of 4-[4-[2-[[(2R)-2-(3-chlorophenyl)-2-hydroxyethyl]amino]ethyl]benzyl]phenol (390 mg) in tetrahydrofuran (3.5 ml) and water (3.5 ml) was added di-tert-butyl dicarbonate (223 mg), and the mixture was stirred at room temperature for 30 minutes. The mixture was partitioned between ethyl acetate and water. The organic layer was separated, washed with brine, dried over magnesium sulfate and evaporated under reduced pressure to give tert-butyl (2R)-N-[2-(3-chlorophenyl)-2-hydroxyethyl]-N-[2-[4-(4-hydroxybenzyl)phenyl]ethyl]carbamate (480 mg).

(+)ESI-MS m/z: 482 (M+H)$^+$

EXAMPLE 66

The following compounds were obtained according to a similar manner to that of Example 57.
(1) tert-Butyl [4-[4-[2-[N-(tert-butoxycarbonyl)-N-[(2R)-2-(3-chlorophenyl)-2-hydroxyethyl]amino]ethyl]benzyl]-phenoxy]acetate (+)ESI-MS m/z: 598 (M+H)$^+$ (2) tert-Butyl [4-[4-[2-[N-(tert-butoxycarbonyl)-N-[(2R)-2-(3-chlorophenyl)-2-hydroxyethyl]amino]ethyl]benzoyl]-phenoxy]acetate (+)ESI-MS m/z: 610 (M+H)$^+$

EXAMPLE 67

A solution of tert-butyl [4-[4-[2-[N-(tert-butoxycarbonyl)-N-[(2R)-2-(3-chlorophenyl)-2-hydroxyethyl]-amino]ethyl]benzyl]phenoxy]acetate (240 mg) and 4N hydrochloride in 1,4-dioxane (3.0 ml) was stirred at room temperature for 24 hours. The mixture was evaporated under reduced pressure. The residue was purified by column chromatography on silica gel (methanol/acetic acid/chloroform=10/1/100) to give a product. To a tetrahydrofuran (2.0 ml) solution of the product, 4N hydrogen chloride in 1,4-dioxane (1.0 ml) was added. The mixture was stirred for 5 minutes and evaporated under reduced pressure to give [4-[4-[2-[[(2R)-2-(3-chlorophenyl)-2-hydroxyethyl]amino]ethyl]benzyl]phenoxy]acetic acid hydrochloride (72 mg).

NMR (DMSO-$d_6$, δ): 2.91-3.24 (6H, m), 3.84 (2H, s), 4.61 (2H, s), 4.94-4.99 (1H, m), 6.32 (1H, br), 6.80 (2H, d, J=8.7 Hz), 7.10-7.21 (6H, m), 7.29-7.46 (4H, m), 8.89 (1H, br) (−)ESI-MS m/z: 438 (M−HCl−H)$^-$

EXAMPLE 68

The following compound was obtained according to a similar manner to that of Example 61.
tert-Butyl N-[(2R)-2-(3-chlorophenyl)-2-hydroxyethyl]-N-[2-[4-(4-hydroxybenzoyl)phenyl]ethyl]carbamate (+)ESI-MS m/z: 496 (M+H)$^+$

EXAMPLE 69

A solution of methyl 4'-[2-(benzylamino)ethyl]-1,1'-biphenyl-4-carboxylate (460 mg), and 2-chloro-5-[(2R)-2-oxiranyl]pyridine (207 mg) in ethanol (10 ml) was refluxed for 18 hours. The mixture was evaporated in vacuo. The residue was purified by column chromatography on silica gel (chlorofor:methanol=100:1) to give methyl 4'-[2-[N-benzyl-N-[(2R)-2-(6-chloro-3-pyridyl)-2-hydroxyethyl]amino]ethyl]-1,1'-biphenyl-4-carboxylate (470 mg) as a colorless foam.

MS m/z: 501 (M+H)

EXAMPLE 70

Methyl 4'-[2-[N-benzyl-N-[(2R)-2-(6-chloro-3-pyridyl)-2-hydroxyethyl]amino]ethyl]-1,1'-biphenyl-4-carboxylate (470 mg), ammonium formate (296 mg) and palladium on carbon powder (100 mg) in methanol (10 ml) and water (1.0 ml) was refluxed for 30 minutes. The reaction mixture was filtrated and poured into water and extracted with ethyl acetate. The organic layer was washed with brine, dried over magnesium sulfate, and evaporated in vacuo. A mixture of the residue was chromatographed (chloroform-methanol) over silica gel to give methyl 4'-[2-[[(2R)-2-hydroxy-2-(3-pyridyl)ethyl]-amino]ethyl]-1,1'-biphenyl-4-carboxylate (326 mg) as a colorless foam.

MS m/z: 377 (M+H)

EXAMPLE 71

At room temperature, to a solution of methyl 4'-[2-[[(2R)-2-hydroxy-2-(3-pyridyl)ethyl]amino]ethyl]-1,1'-biphenyl-4-carboxylate (326 mg) in methanol was added 1N sodium hydride (0.87 ml), and the mixture was stirred at the same temperature for 3 hours. The resulting mixture was evaporated under reduced pressure and dried to give sodium 4-[4-

[2-[[(2R)-2-hydroxy-2-(3-pyridyl)ethyl]amino]-ethyl]]-1,1'-biphenyl-4-carboxylate (220 mg) as a colorless powder.

NMR (DMSO-d$_6$, δ): 2.50-2.80 (6H, m), 4.70 (1H, t, J=6 Hz), 7.10-7.40 (3H, m), 7.50-7.70 (5H, m), 7.90-8.00 (1H, m), 8.40-8.50 (2H, m) MS m/z: 361 (M−H)

EXAMPLE 72

4-[[4-(2-Aminoethyl)phenyl]thio]phenol (295 mg) and (2R)-2-(3-chlorophenyl)oxirane (186 mg) in ethanol (3.5 ml) was refluxed for 6 hours. The mixture was evaporated. The residue was purified by column chromatography on silica gel (chloroform/methanol=100/3) to give 4-[[4-[2-[[(2R)-2-(3-chlorophenyl)-2-hydroxyethyl]amino]ethyl]phenyl]thio]phenol (155 mg).

(+)ESI-MS m/z: 400 (M+H)$^+$

EXAMPLE 73

To a solution of tert-butyl N-[(2R)-2-(3-chlorophenyl)-2-hydroxyethyl]-N-[2-[4-[(4-hydroxyphenyl)thio]phenyl]-ethyl]carbamate (195 mg) and potassium carbonate (59 mg) in N,N-dimethylformamide (3 ml) was added tert-butyl bromoacetate (84 mg), and the mixture was stirred at room temperature for 3 hours. The mixture was partitioned between ethyl acetate and water. The organic layer was separated, washed with water and brine, dried over magnesium sulfate and evaporated under reduced pressure. The residue was purified by column chromatography on silica gel (hexane/ethyl acetate=3/1) to give tert-butyl [4-[[4-[2-[N-(tert-butoxycarbonyl)-N-[(2R)-2-(3-chlorophenyl)-2-hydroxyethyl]amino]ethyl]phenyl]thio]phenoxy]acetate (168 mg).

(+)ESI-MS m/z: 636 (M+Na)

The invention claimed is:

1. A compound of the formula [I], or a salt thereof:

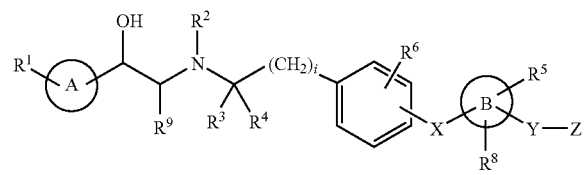
[I]

wherein

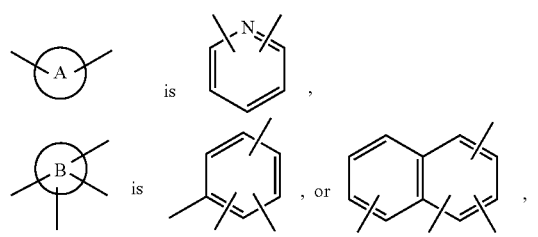

X is bond, —CH$_2$—,

—O—, —OCH$_2$—, —CH$_2$O—, —S— or

wherein R$^7$ is hydrogen or lower alkyl,

Y is bond, —O—(CH$_2$)$_n$— wherein n is 1, 2, 3 or 4, —(CH$_2$)$_m$— wherein m is 1, 2, 3 or 4,

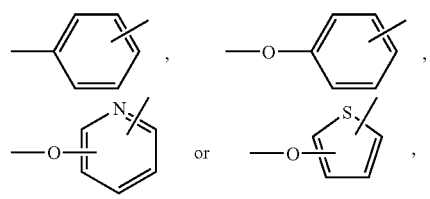

Z is cyano, tetrazolyl, (benzylsulfonyl)carbamoyl, benzoylsulfamoyl, formyl, carboxy or protected carboxy, R$^1$ is hydrogen, lower alkyl or halogen, R$^2$ is hydrogen or an amino protective group, R$^3$ is hydrogen or lower alkyl, R$^4$ is hydrogen or lower alkyl, R$^5$ and R$^8$ are each independently hydrogen, halogen, hydroxy, lower alkyl, lower alkenyl, lower alkoxy, hydroxy(lower)alkoxy, mono-halo(lower)alkoxy, di-halo(lower)alkoxy, tri-halo(lower)alkoxy, lower alkoxy(lower)alkoxy, lower alkenyloxy, cyclo(lower)alkyloxy, cyclo(lower)alkyl(lower)alkoxy, benzyloxy, phenoxy, lower alkylthio, cyclo(lower)alkylthio, lower alkylsulfonyl, cyclo(lower)alkylsulfonyl, amino, mono-(lower)alkylamino di-(lower)alkylamino, mono-halo(lower)alkyl, di-halo(lower)alkyl, tri-halo(lower)alkyl cyano, piperidinyl or phenyl, R$^6$ is hydrogen, lower alkyl or halogen, R$^9$ is hydrogen or lower alkyl, and i is 1 or 2, provided that (1) when X is bond, —CH$_2$—,

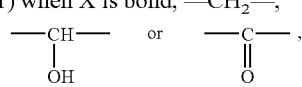

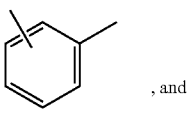 is 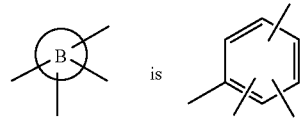, and then R$^5$ is not hydrogen, or (2) when i is 1, then

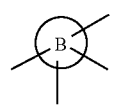

is not

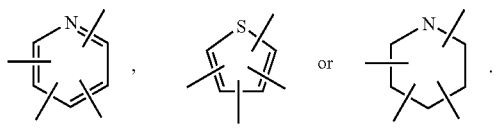

2. The compound of formula [I] as defined in claim 1,

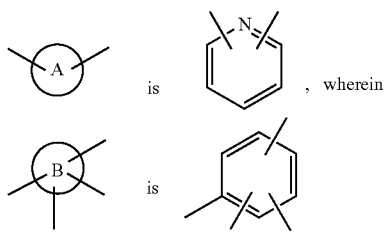
wherein

X is bond, —O—, —OCH$_2$—, —S— or

wherein R$^7$ is hydrogen or lower alkyl,
Y is bond, —O—(CH$_2$)$_n$— wherein n is 1, 2, 3 or 4, —(CH$_2$)$_m$— wherein m is 1, 2, 3 or 4,

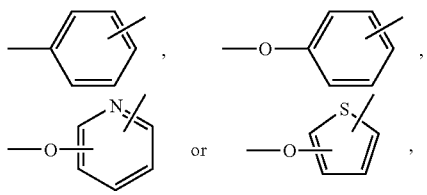

Z is carboxy or lower alkoxycarbonyl,
R$^1$ is hydrogen or halogen,
R$^2$ is hydrogen,
R$^3$ is hydrogen or lower alkyl,
R$^4$ is hydrogen,
R$^5$ is halogen, hydroxy, lower alkyl, lower alkoxy, hydroxy (lower)alkoxy, mono-halo(lower)alkoxy, di-halo (lower)alkoxy, tri-halo(lower)alkoxy, lower alkoxy (lower)alkoxy, lower alkenyloxy, cyclo(lower)alkyloxy, phenoxy or phenyl,
R$^6$ is hydrogen,
R$^8$ is hydrogen or lower alkyl,
R$^9$ is hydrogen or lower alkyl, and
i is 1 or 2.

3. The compound of formula [I] as defined in claim 2, wherein

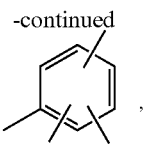
is

X is bond, —O—, —OCH$_2$—, —S— or

wherein R$^7$ is hydrogen or lower alkyl,
Y is bond, —O—(CH$_2$)$_n$— wherein n is 1 or 2 or —(CH$_2$)$_m$— wherein m is 1 or 2,
Z is carboxy or lower alkoxycarbonyl,
R$^1$ is hydrogen or halogen,
R$^2$ is hydrogen,
R$^3$ is hydrogen or lower alkyl,
R$^4$ is hydrogen,
R$^5$ is halogen, hydroxy, lower alkyl or lower alkoxy,
R$^6$ is hydrogen,
R$^8$ is hydrogen or lower alkyl,
R$^9$ is hydrogen or lower alkyl, and
i is 1.

4. The compound of formula [I], as defined in claim 3, wherein

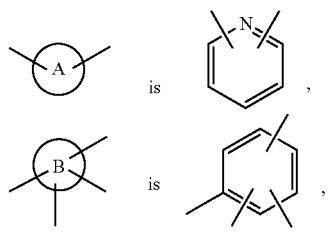

X is bond,
Y is bond,
Z is carboxy or lower alkoxycarbonyl,
R$^1$ is hydrogen or halogen,
R$^2$ is hydrogen,
R$^3$ is hydrogen or lower alkyl,
R$^4$ is hydrogen,
R$^5$ is halogen, hydroxy, lower alkyl or lower alkoxy,
R$^6$ is hydrogen,
R$^8$ is hydrogen or lower alkyl,
R$^9$ is hydrogen or lower alkyl, and
i is 1.

5. The compound of formula [I] as defined in claim 4, which is selected from the group consisting of
4'-[2-[[(2R)-2-Hydroxy-2-(3-pyridyl)ethyl]amino]-ethyl]-2-methyl-1,1'-biphenyl-4-carboxylic acid, and
4'-[(2R)-2-[[(Tt.)-2-Hydroxy-2-(3-pyridyl)ethyl]-amino] propyl]-3-methoxy-1,1'-biphenyl-4-carboxylic acid,
or a pharmaceutically acceptable salt thereof.

6. A process for preparing a compound of formula [I] as defined in claim 1, or a salt thereof, which comprises, (i) reacting a compound [II] of the formula:

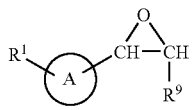

[II]

wherein $R^1$, $R^9$ and

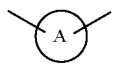

are each as defined in claim 1, with a compound [III] of the formula:

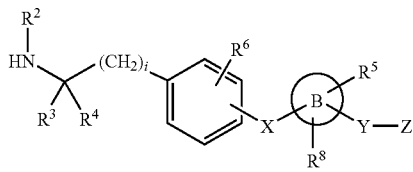

[III]

wherein

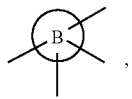

,

X, Y, Z, $R^2$, $R^3$, $R^4$, $R^5$ $R^6$, $R^8$ and i are each as defined in claim 1,
or a salt thereof, to give a compound [I] of the formula:

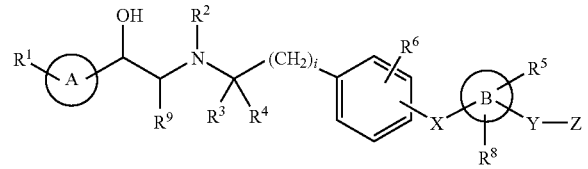

[I]

wherein

,

X, Y, Z, $R^1$, $R^2$, $R^3$, $R^4$, $R^5$, $R^6$, $R^8$, $R^9$ and i are each as defined in claim 1,
or a salt thereof, (ii) subjecting a compound [Ia] of the formula:

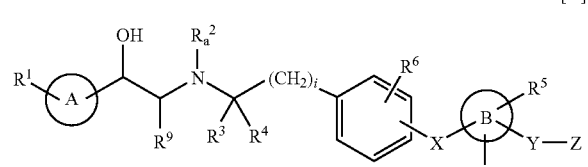

[Ia]

wherein

,

X, Y, Z, $R^1$, $R^3$, $R^4$, $R^5$, $R^6$, $R^8$, $R^9$ and i are each as defined in claim 1, and $R_a^2$ is an amino protective group,
or a salt thereof, to elimination reaction of the amino protective group, to give a compound [Ib] of the formula:

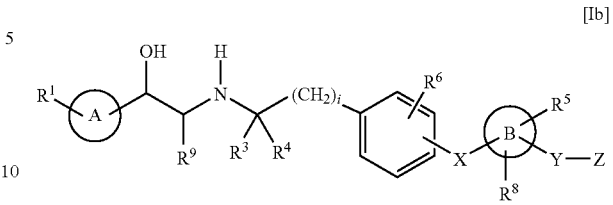

[Ib]

wherein

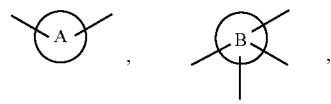

X, Y, Z, $R^1$, $R^3$, $R^4$, $R^5$, $R^6$, $R^8$, $R^9$ and i are each as defined in claim 1,
or a salt thereof, (iii) reacting a compound [IV] of the formula:

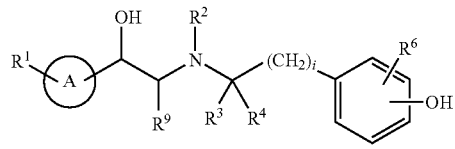

[IV]

wherein

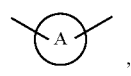

, $R^1$, $R^2$, $R^3$, $R^4$, $R^6$, $R^9$ and i are each as defined in claim 1,
or a salt thereof, with a compound [V] of the formula:

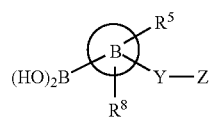

[V]

wherein

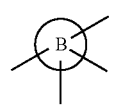

,

Y, Z, $R^5$ and $R^8$ are each as defined in claim 1,
or a salt thereof, to give a compound [Ic] of the formula:

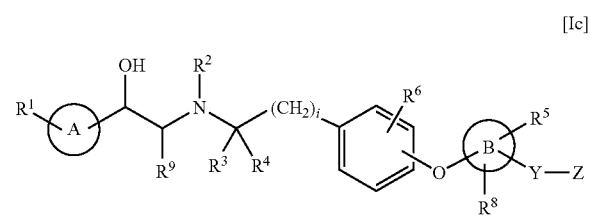

[Ic]

wherein

Y, Z, $R^1$, $R^2$, $R^3$, $R^4$, $R^5$, $R^6$, $R^8$ and i are each as defined in claim 1, or a salt thereof, (iv) reacting a compound [IV] of the formula:

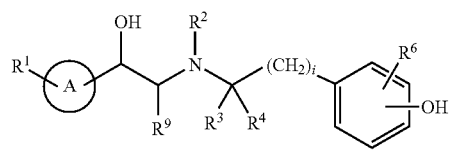

[IV]

wherein

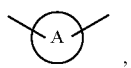

$R^1$, $R^2$, $R^3$, $R^4$, $R^6$, $R^9$ and i are each as defined in claim 1, or a salt thereof, with a compound [VI] of the formula:

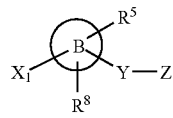

[VI]

wherein

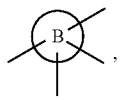

Y, Z, $R^5$ and $R^8$ are each as defined in claim 1, and $X_1$ is a leaving group, or a salt thereof, to give a compound [Ic] of the formula:

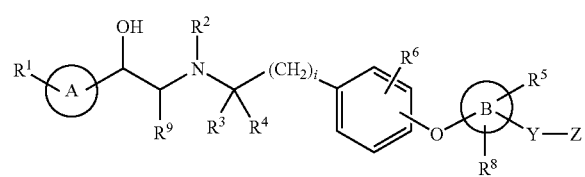

[Ic]

wherein

Y, Z, $R^1$, $R^2$, $R^3$, $R^4$, $R^5$, $R^6$, $R^8$, $R^9$ and i are each as defined in claim 1, or a salt thereof, (v) reacting a compound [VII] of the formula:

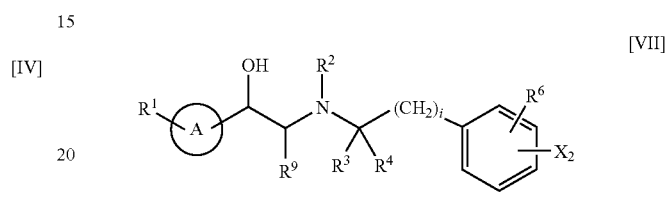

[VII]

wherein

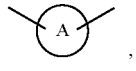

$R^1$, $R^2$, $R^3$, $R^4$, $R^6$, $R^9$ and i are each as defined in claim 1, $X_2$ is a leaving group, or a salt thereof, with a compound [V] of the formula:

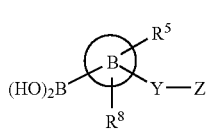

[V]

wherein

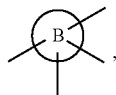

Y, Z, $R^5$ and $R^8$ are each as defined in claim 1, or a salt thereof, to give a compound [Id] of the formula:

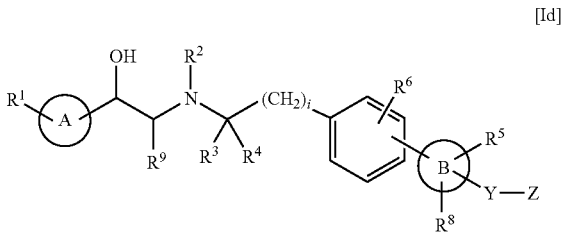

[Id]

wherein

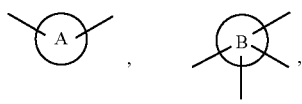

Y, Z, R¹, R², R³, R⁴, R⁵, R⁶, R⁸, R⁹ and i are each as defined in claim 1,
or a salt thereof, and
(vi) subjecting a compound [Ie] of the formula:

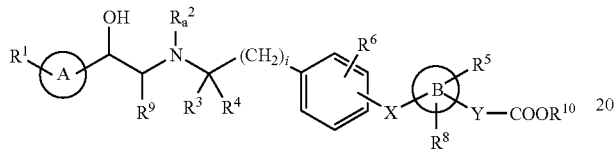

[Ie]

wherein

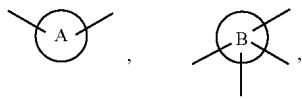

X, Y, R¹, R³, R⁴, R⁵, R⁶, R⁸, R⁹ and i are each as defined in claim 1,
R¹⁰ is lower alkyl, and
$R_a^2$ is an amino protective group,
or a salt thereof, to deesterification reaction, to give a compound [If] of the formula:

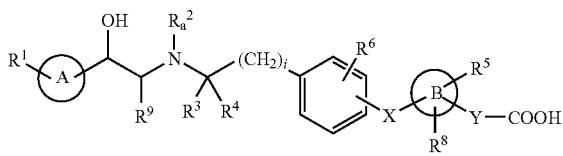

[If]

wherein

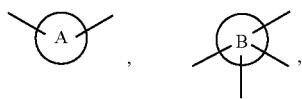

X, Y, R¹, R³, R⁴, R⁵, R⁶, R⁸, R⁹ and i are each as defined in claim 1,
$R_a^2$ is defined above, or a salt thereof, and then subjecting the compound [If] above to elimination reaction of amino protective group, to give a compound [Ig] of the formula:

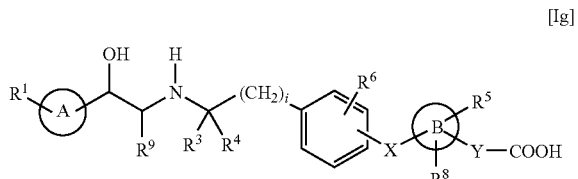

[Ig]

wherein

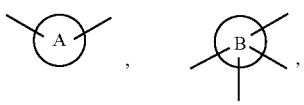

X, Y, R¹, R³, R⁴, R⁵, R⁶, R⁸, R⁹ and i are each as defined in claim 1,
or a salt thereof.

7. A pharmaceutical composition which comprises a therapeutically effective amount of a compound of formula [I] as defined in claim 1 or a pharmaceutically acceptable salt thereof in admixture with pharmaceutically acceptable carriers or excipients.

8. A method of agonizing $\beta_3$ adrenergic receptor comprising administering an effective amount of a compound of formula [I] as defined in claim 1 or a pharmaceutically acceptable salt thereof to a subject in need thereof.

9. A method for treating pollakiuria in a human in need thereof which comprises administering a therapeutically effective amount of a compound of formula [I] as defined in claim 1 or a pharmaceutically acceptable salt thereof.

10. A method for treating pollakiuria in an animal in need thereof which comprises administering a therapeutically effective amount of a compound of formula [I] as defined in claim 1 or a pharmaceutically acceptable salt thereof.

11. A method for treating urinary incontinence in a human in need thereof which comprises administering a therapeutically effective amount of a compound of formula [I] as defined in claim 1 or a pharmaceutically acceptable salt thereof.

12. A method for treating urinary incontinence in an animal in need thereof which comprises administering a therapeutically effective amount of a compound of formula [I] as defined in claim 1 or a pharmaceutically acceptable salt thereof.

* * * * *